US008034603B2

(12) United States Patent
Ball et al.

(10) Patent No.: US 8,034,603 B2
(45) Date of Patent: Oct. 11, 2011

(54) NUCLEIC ACID MOLECULE

(76) Inventors: Andrew Ball, Bedford Park (AU);
Robert Moore, Bedford Park (AU);
Gregory Knowles, Bedford Park (AU);
Jian Qin, Bedford Park (AU)

( * ) Notice: Subject to any disclaimer, the term of this patent is extended or adjusted under 35 U.S.C. 154(b) by 0 days.

(21) Appl. No.: 12/882,927

(22) Filed: Sep. 15, 2010

(65) Prior Publication Data

US 2011/0190484 A1    Aug. 4, 2011

(30) Foreign Application Priority Data

Sep. 15, 2009  (AU) ................ 2009904482
Nov. 4, 2009   (AU) ................ 2009905381
Feb. 24, 2010  (AU) ................ 2010900782

(51) Int. Cl.
*C12N 1/20*   (2006.01)
*C07H 21/04*  (2006.01)

(52) U.S. Cl. ............ 435/252.3; 435/183; 435/320.1; 536/23.2

(58) Field of Classification Search .......... 435/183; 536/23.2
See application file for complete search history.

(56) References Cited

U.S. PATENT DOCUMENTS 7,232,679 B2    6/2007  Berry et al.
2010/0041120 A1 2/2010  Chappell et al.

FOREIGN PATENT DOCUMENTS

WO    WO 2006/121950   11/2006
WO    WO 2009/158433   12/2009

OTHER PUBLICATIONS

Auffray, "Protection Against Singlet Oxygen, the Main Actor of Sebum Squalene Peroxidation During Sun Exposure, Using *Commiphora myrrha* Essential Oil," *Int. J. Cosmet. Sci.* 29: 23-29 (2007).
Catchpole et al., "Extraction of Squalene from Shark Liver Oil in a Packed Column Using Supercritical Carbon Dioxide," *Ind. Eng. Chem. Res.* 36: 4318-4324 (1997).
Colombo et al., "Use of the Bleomycin Resistance Gene to Generate Tagged Insertional Mutants of *Chlamydomonas reinhardtii* That Require Elevated CO2 for Optimal Growth," *Funct. Plant Biol.*, 29: 231-241 (2002).
Copping et al., "Techno-Economic Feasibility Analysis of Offshore Seaweed Farming for Bioenergy and Biobased Products," *Independent Research and Development Report*, Battelle Pacific Northwest Division (2008).
Cox and Coulter, "Adjuvants—A Classification and Review of Their Modes of Action," *Vaccine* 15:248-256 (1997).
Day et al., "Studies on the Maintenance and Expression of Cloned DNA Fragments in the Nuclear Genome of the Green Alga *Chlamydomonas reinhardtii*," *Physiologia plantarum* 78:254-260 (1990).
Fischer and Rochaix, "The Flanking Regions of PsaD Drive Efficient Gene Expression in the Nucleus of the Green Alga *Chlamydomonas reinhardtii*," *Mol. Genet. Genomics* 265:888-894 (2001).
Fox, "Squalene Emulsions for Parenteral Vaccine and Drug Delivery," *Molecules* 14:3286-3312 (2009).

Gapor et al., "Squalene in Oils and Fats," *Palm Oil Developments*. 32: 36-40 (1985).
Gorman and Levine, "Cytochrome F and Plastrocyanin: Their Sequence in the Photosynthetic Electron Transport Chain of *Chlamydomonas reinhardi*," *Proc. Natl. Acad. Sci. U.S.A.* 54:1665-1669 (1965).
Gu et al., "Function-Structure Studies and Identification of Three Enzyme Domains Involved in the Catalytic Activity in Rat Hepatic Squalene Synthase," *J. Biol. Chem.* 273: 12515-12525 (1998).
He et al., "Extraction and Purification of Squalene from *Amaranthus* Grain," *J. Agric. Food Chem.* 50, 368-372 (2002).
Hillen et al., "Hydrocracking of the Oils of *Botryococcus braunii* to Transport Fuels," *Biotechnol. and Bioeng.* 24:193-205 (1982).
Huang et al., "Biological and Pharmacological Activities of Squalene and Related Compounds: Potential Uses in Cosmetic Dermatology," *Molecules.* 14: 540-554 (2009).
Jang et al., "High Level Production of Bovine Angiogenin in *E. coli* by an Efficient Refolding Procedure," *Biotechnol. Lett.* 26: 1501-1504 (2004).
Kucho et al., "Cis-Acting Elements and DNA-Binding Proteins Involved in $CO_2$—Responsive Transcriptional Activation of Cah1 Encoding a Periplasmic Carbonic Anhydrase in *Chlamydomonas reinhadtii*," *Plant Physiology* 133:783-793 (2003).
Lumbreras et al., "Efficient Foreign Gene Expression in *Chlamydomonas reinhardtii* Mediated by an Endogenous Intron," *Plant J.* 14, 441-447 (1998).
Metzger et al., "*Botryococcus braunii*: A Rich Source for Hydrocarbons and Related Ether Lipids," *Appl. Microbiol. Biotechnol.* 66: 486-496 (2005).
Metzger et al., "Botryococcene Distribution in Strains of the Green Alga *Botryococcus braunii*," *Phytochemistry*. 27: 1383-1388 (1988).
Newmark, "Squalene, Olive Oil and Cancer Risk: A Review and Hypothesis," *Cancer Epidemiol. Biomarkers Prev.* 6: 1101-1103 (1997).
Okada et al., "Molecular Characterization of Squalene Synthase from the Green Microalga *Botryococcus braunii* Race B," *Arch. Biochem. Biophys.* 373(2): 307-317 (2000).
Okada et al., "Characterization of Botryococcene Synthase Enzyme Activity, a Squalene Synthase-Like Activity From the Green Microalga *Botryococcus braunii*, Race B," *Arch. Biochem. Biophys.* 422: 100-118 (2004).
Pandit et al., "Crystal Structure of Human Squalene Synthase," *J. Biol. Chem.* 275: 30610-30617 (2000).
Rustam'yan et al., "Penetration of Cow Milk Angiogenin Into the Blood of Mice After Peroral Introduction," *Biology Bulletin.* 29(2): 165-167 (2002).
Schroda et al., "The HSP70A Promoter as a Tool for the Improved Expression of Transgenes in *Chlamydomonas*," *Plant J.* 21(2): 121-131 (2000).

(Continued)

*Primary Examiner* — Tekchand Saidha
(74) *Attorney, Agent, or Firm* — Clark & Elbing LLP

(57) ABSTRACT

The invention relates to an isolated nucleic acid molecule encoding a polypeptide capable of producing a triterpenoid hydrocarbon. The invention also relates to the encoded polypeptide, a vector comprising the nucleic acid molecule, a recombinant non-human organism comprising the nucleic acid molecule, and to methods of producing a triterpenoid hydrocarbon or an intermediate of biofuel using the nucleic acid molecule, polypeptide or recombinant organism.

18 Claims, 23 Drawing Sheets

OTHER PUBLICATIONS

Schroda et al., "Sequence Elements Within an HSP70 Promoter Counteract Transcriptional Transgene Silencing in *Chlamydomonas,*" *Plant J.* 31(4): 445-455 (2002).

Schroepfer, "Sterol Biosynthesis," *Ann. Rev. Biochemistry.* 50: 585-621 (1981).

Okada et al., "Trial Use of *Botryococcus braunii* As Energy Resources," 183-198, Chem Abstr., 2006-542348 (Abstract only) (2005).

Tran et al., "Catalytic Upgrading of Biofinery Oil From Micro-Algae," *Fuel.* 89: 265-274 (2010).

Wu et al., "Efficient Expression of Green Fluorescent Protein (GFP) Mediated by a Chimeric Promoter in *Chlamydomonas reinhardtii,*" *Chinese Journal of Oceanology and Limnology.* 26(3): 242-247 (2008.).

Figure 1 (SEQ ID NO: 1; encoded by Exon 2.1).

QVPEVVHRLPLELQDPICIFYLLLRALDTVEDDMNLPSKVKVDLLREFHEHCKDRC

Figure 2 (SEQ ID NO: 2; encoded by Exon 4.1).

EQVFVENVKYMGNGMADFIDKEILTVDEYDLYCHYVAGSCGIA

Figure 3 (SEQ ID NO: 3; encoded by Exon 5.3).

QFNLATPEADSMEFSNSLGLLLQKANIITDYNEDINEEPRPR

Figure 4 (SEQ ID NO: 4; encoded by Exon 6.1).

MFWPQEIWANYSEKLADFNEPANLEKAMKCLNHMVTDALRHIEPSLKGI

Figure 5 (SEQ ID NO: 5; encoded by Exon 9.2).

RCLEETKNDPSVATTIKRLQSIQATCREG

Figure 6 (Exon 2.1, SEQ ID NO: 6).

GTGGCTGTCCCTACCTGATGGGTTTCTCTGTGTCTGCAGGTTCCCGAGGTTTGTTCACAGGCTTCCTCTGGAACT
CCAGGATCCAATCTGCATTTTTTATCTCCTGCTGCGTGCACTAGATACAGTGGAGGATGATATGAACCTCCCAAG
TAAGGTGAAGGTAGATCTGTTGCGCGAGTTTCATGAGCATTGTAAAGACAGGTGCGTCCCTTGTTCTCATGGAAC
TAGATAACAGCAAATGCACATATTCTACAGAGGAGTGTTTTTCTGTGTGTCTGTGTTACTGCGCTGACACGCACT
TGACCCCTCCCCGTTCTTCGCTCCAGTTTGCTTCCCTCTTTTCCGCTTCTTCTGCTTCTGACCCTACCTAACACT
CCA

Figure 7 (Exons 3.11 and 4.1 with intervening intron, SEQ ID NO: 7).

GTATCTGCCTACAGTTTCTACTCCATTTCGAGATGTGCTAAGTTCACAAACGAGTTCCTTGTATGCAGGAACTGG
AGCATGAAAAGTGATTATGGCATCTATGCAGACTTGATGGAAAGGTTTCCTCTGGTGATTTCCGTCCTGGAAAAG
CTTCCTAAGCCCACACAGGAGGTAGGAAAGAAGCTGTAGCCCAAGCTTTTTGAGCGAGCTTATCTGAGTGCTCGA
ACGGGTACTCAGCTTGGGTCCTTCCTACATGTGGCTGGCGAGAACACTAACAGTTGCAATGAAGAGTTCTTCAGG
AGGATTGCTGGCTGCCATGTCTTGTTTTGTTGTCCAGAGGAGTTTTCAGCTACGTTTGAAATGCTACTGTTGTAC
CTAAAGTGGAGAATGTAGGGAAAGTCAGTTGTCGTCCCCCTCTTTTTTCTGTTTGAGTTGTGTTCCCATTATTCA
ATAGCATTTCCTGATGGTTGTATGGTGGATGTCTTGCATCCCAGATACAAATACAAGCCAATTTTGCAGGAGAGC
ACTCCTGAAGATGGTGTCCTTCCACTGTTGTCACGGACGAGGGGTGCTGAATGTTGTGGGCACAAACAGCAGTGC
ATCCCATACATGGAATGTTGTTGTCTACACGTTGACACGTTCCAAGCATCACTAGCTGCCCTCCTGATACTCTTC
TCGGTCATCTAAGCTCACGCATCCGAACATGGCACTTTACAAAAAGAAACAGTGTTTTTGACGTTGAACAGGTT
TTTGTGGAGAATGTCAAATATATGGGCAATGGCATGGCAGACTTTATTGATAAGGAGATCTTGACTGTGGATGAG
TACGATCTGTACTGCCACTATGTGGCTGGTAGTTGTGGCATTGCTGTTGTCAAGGKACGTACTCTCTAACATAGT
CTGGTACCCCCAGTTTTGCCTCTGCAGATGTTATTGCAAGTGGCTTCCACGAACACCATGGGCTCCTGGTGCAGT
CCAACTTGCGAGGTCATGGGCTTGAAGTCGCCCTGTCTACGGAACACCCGATTCATGACCAAGGTTACATAATAT
CGTTGTTCCTTAATTCGGAATACTAAAGTTAAGGTTTCGGAACGTCTACCCTAAGCCCTAGAACACCGCCAATTG
GCCTGGGAGACATTTCTAGTGTGTTTTCTGGTCTTGCGAGGAT

Figure 8 (Exons 5.3 and 6.1 with intervening intron, SEQ ID NO: 8).

GTTATTGTCCAATTTAACCTTGCCACGCCGGAAGCTGACTCGATGGAGTTTTCCAACAGCCTAGGATTGTTGCTT
CAGAAAGCCAACATCATTACTGACTACAATGAGGACATTAACGAAGAACCCAGACCCCGGTATGCCACTAGCATA
TTCAGAGACANCATGGCTCTGTACACAATCTTACTGTAAAAATGACTGAAAGGAGTGGCTGCAATGTTTTGTCTG

Figure 8 continued

```
TCAAACCTATCAGGGCAAGTCGACTTGAAGGTCTGGTTCGCAATATGGGTTTTGCATGGTCACGTTTAGAGTATG
TGGTAACGATTGATATCTCCTCTGAAGTGCCATTTGCTGTATGTATGGAGTGGCCGTCAGAAGTCCCAGGATAAG
AGCAACTGGTTATTGTCAAAAACTTTGACTGGGTACATTGGGAGTTCCTGCAGGATGTTCTGGCCCCAAGAGATC
TGGGCCAATTACTCGGAAAAGTTAGCTGACTTTAATGAACCCGCCAACCTTGAAAAAGCTATGAAGTGCTTGAAC
CACATGGTCACAGATGCCCTGCGCCACATTGAGCCATCTCTTAAGGGCATGGG
```

Figure 9 (Exon 9.2, SEQ ID NO: 9).

```
AGGTGTCTGGAGGAGACAAAGAATGATCCCTCTGTGGCCACAACCATCAAGCGGCTGCAGTCAATCCAGGCCACG
TGCAGAGAAGGCC
```

Figure 10 (gi|6636500|gb|AAF20201.1|AF205791_1 squalene synthase [*Botryococcus braunii*], SEQ ID NO: 10).

```
MGMLRWGVESLQNPDELIPVLRMIYADKFGKIKPKDEDRGFCYEILNLVSRSFAIVIQQLPAQLRDPVCI
FYLVLRALDTVEDDMKIAATTKIPLLRDFYEKISDRSFRMTAGDQKDYIRLLDQYPKVTSVFLKLTPREQ
EIIADITKRMGNGMADFVHKGVPDTVGDYDLYCHYVAGVVGLGLSQLFVASGLQSPSLTRSEDLSNHMGL
FLQKTNIIRDYFEDINELPAPRMFWPREIWGKYANNLAEFKDPANKAAAMCCLNEMVTDALRHAVYCLQY
MSMIEDPQIFNFCAIPQTMAFGTLSLCYNNYTIFTGPKAAVKLRRGTTAKLMYTSNNMFAMYRHFLNFAE
KLEVRCNTETSEDPSVTTTLEHLHKIKAACKAGLARTKDDTFDELRSRLLALTGGSFYLAWTYNFLDLRG
PGDLPTFLSVTQHWWSILIFLISIAVFFIPSRPSPRPTLSA
```

Figure 11 (gi|6636499|gb|AF205791.1|AF205791 *Botryococcus braunii* squalene synthase mRNA, complete cds, SEQ ID NO: 11).

```
AACAGCAACAAGTCCTCTGCGTCAGGCAAAACGTCCGTTTGTATGGCTTGGCGCTTGAAAGCTGGTGGGG
ATAAACGTCAAAAGAAAGAAGCTCTGTTCGGGTTCACGGGTGTCGTTTAGTACTTTCCCCTACGACATTG
TCAGCCTTGGCTCATCGCAATCCAACCAAATATGGGGATGCTTCGCTGGGGAGTGGAGTCTTTGCAGAAT
CCAGATGAATTAATCCCGGTCTTGAGGATGATTTATGCTGATAAGTTTGGAAAGATCAAGCCAAAGGACG
AAGACCGGGGCTTCTGCTATGAAATTTTAAACCTTGTTTCAAGAAGTTTTGCAATCGTCATCCAACAGCT
CCCTGCACAGCTGAGGGACCCAGTCTGCATATTTTACCTTGTACTACGCGCCCTGGACACAGTCGAAGAT
GATATGAAAATTGCAGCAACCACCAAGATTCCCTTGCTGCGTGACTTTTATGAGAAAATTTCTGACAGGT
CATTCCGCATGACGGCCGGAGATCAAAAAGACTACATCAGGCTGTTGGATCAGTACCCCAAAGTGACAAG
CGTTTTCTTGAAATTGACCCCCCGTGAACAAGAGATAATTGCAGACATTACAAAGCGGATGGGGAATGGA
ATGGCTGACTTCGTGCATAAGGGTGTTCCCGACACAGTGGGGGACTACGACCTTTACTGCCACTATGTTG
CTGGGGTGGTGGGTCTCGGGCTTTCCCAGTTGTTCGTTGCGAGTGGACTACAGTCACCCTCTTTGACCCG
CAGTGAAGACCTTTCCAATCACATGGGCCTCTTCCTTCAGAAGACCAACATCATCCGCGACTACTTTGAG
GACATCAATGAGCTGCCTGCCCCCCGGATGTTCTGGCCCAGAGAGATCTGGGGCAAGTATGCGAACAACC
TCGCTGAGTTCAAAGACCCGGCCAACAAGGCGGCTGCAATGTGCTGCCTCAACGAGATGGTCACAGATGC
ATTGAGGCACGCGGTGTACTGCCTGCAGTACATGTCCATGATTGAGGATCCGCAGATCTTCAACTTCTGT
GCCATCCCTCAGACCATGGCCTTCGGCACCCTGTCTTTGTTACAACAACTACACTATCTTCACAGGGC
CCAAAGCGGCTGTGAAGCTGCGTAGGGGCACCACTGCCAAGCTGATGTACACCTCTAACAATATGTTTGC
GATGTACCGTCATTTCCTCAACTTCGCAGAGAAGCTGGAAGTCAGATGCAACACCGAGACCAGCGAGGAT
CCCAGCGTGACCACCACTCTGGAACACCTGCATAAGATCAAAGCTGCCTGCAAGGCTGGGCTGGCACGCA
CAAAAGATGACACCTTTGACGAATTGAGGAGCAGGTTGTTAGCGCTGACGGGAGGCAGCTTCTACCTCGC
CTGGACCTACAATTTCCTAGACCTTCGAGGCCCGGGAGACCTGCCCACCTTCTTATCTGTAACCCAACAT
TGGTGGTCTATTCTGATCTTCCTCATTTCGATTGCCGTCTTCTTTATTCCGTCGAGGCCCTCACCTAGAC
CCACACTCAGCGCCTAATCCTTTGGCTCTCGTCAATTCCGGAGTCCCCATTGTTGTCAGCACTTGGGGA
ATTTCGTGGTCTTCTTGACCACACTCTTGTCTCTGGCAGAGGTCAAGGACACTGTCAGGGACAAGTGAGT
ATTCTGACCCCCCCCCCCCCCCCTCTGCTCCTTTCACCACCCCTCCCTATCATCTGGGGCAAAGCTTG
GGAATGGGCCCGTCCCCCTGTTGTCCCGCTCAGATGCAAAGTTTGGGTTATGTAACTGGGTTGAACGGCT
CGGGGCGGTTTGAAGCTGTCCCTTGTTGGAGATGGAAAATTGCAGGGCCCGGGGGGTTAACTGGACACG
CTCTTCCGTCCCGCAGTGTCCTTCTGGCTTTATTCTGCCGTGGATGCTGTGAACCCGCCCCCTCTCTGGG
CCGGCTCAATATACAAGTATTAGTTTCGGTGTTTGTGTCAATCCTTTCTCACAACTTCCCTGTTCGTTGG
```

Figure 11 continued

```
ACTGGAGACGCACCCTTAGGTCCTTTGATTGGGAATGCGGCCCCTTTGGGTCTTTAGGCTCTCGGGTAGT
CTAGTTTGCAATTGTTGCATGGGCGCGGCTTTGCACAGACGCCTGGACCTTCATTGAGACACGTTTCGGA
AAACTCGACAGTTTTGAGGTAACCTGCTCGTGGGCCTCGGTGTGTCTGGAGGTGTCAGGGGCCTGTGCTC
CCTGCTGGGATGTTCCCGCTTTGCTGTAAAAAGTCGGACGTTTGTTATCCTTTGCGGGGGTTCATCTTTG
AGTGGGCCCTGCTTCTCTGCCCGTGTGATGTAATGGTTTGTATTGGATAGGTATGTTGCCTTATCTCGTG
TATGGAATTCGTATGGTACTTGCAGTATTCAGGAGACTTGAGTAACGACATCGAGGACAGGTAACAAGCG
CTCCGATTATGTGCTCTGTTACACCCGACTTCCAAAGATTTATGCGAGGTCCTGGGGAACGCAGATTTGA
CATTGGAGAGCCCCAATTGGCCGTGGCAATCTGTAGAATGTCAAAAGAGAAAACAGGAAATCAGGTTTTA
AAGTCCGTGCCTATCAGCATCCTGTGAAAGCTGATGCGGTTACGGGATGAATGTCAGGAATACTCGCTCC
AGTATTAACGTGCGCAGATTCCGACTGAAGCAAATCGATGAAATTTGGGGAGGTGTCGTTTTTAGACCTT
GACAACGGCCATGGGTCGTACCTTTTGCAAAGTATATATTTATTTGCACTAACTCATTAGGCACGTTGG
TTTTTTTTGTCCCCCTCGGAACGCCTTTTAAGATAGTTAACTAGTTTGGTCAGGGTATTCGTCAGAAGC
ACGAAGCACAGAAGGTTTCTTTTGAGATGGCGGCGATTGTTTTCCACGAGAGCAGAGTCAATCTCACGCG
TACTCGAGCAAACATCGTTGGTCAGGACATGGTGTTGTCTCTTGGCCGGCCCTGTAACTTTGATGCCCCC
AAAAAAAAAAAAAAAAAAAAAAAAAAAAAAAAAAAAAAAAAAAAAAAAAAAAAAAAAAAAAAAAAAA
```

Figure 12 (gi|7532841|gb|AAF63255.1| squalene synthase [*Botryococcus braunii*], SEQ ID NO: 12).

```
YCHYVAGVVGLGLSQLFVASGLQSPSLTRSEDLSNHMGLFLQKTNIIRDYFEDINELPAPRMFWPREIWG
KYANNLAEFKDPANKAAAMCCLNEMVTDALRHAVYCLQYMSMIEDPQIFNFCAIPQ
```

Figure 13 (gi|7532838|gb|AH009227.1|SEG_AF205789S *Botryococcus braunii* squalene synthase gene, partial cds, SEQ ID NO: 13).

```
TACTGCCACTACGTCGCTGGGGTGGTGGGTCTCGGGCTTTCCCAGGTGGGTCTTCTGTGTGTGCCCATGC
TGTCATACCCTAGATGAACTCATTGACCTAACCTTTGCCCACACGCTTCTTGCACATACGTTAACTCGTT
GACCTAACTCGTCCGCTTGGCAACCCTACACTTCTGCATGAGGCGTAACCCATGTCCGCAACAGTTCCAA
GAATTAAGCTCTAAAGGGGGATGGGCAAAGTTGCGTGCAAGTGAGAACTGTTGCGGTTGTCGGTGCCTTG
CTTGGCCGCCAACGCTACTTGTAGCGACATAACCAGCACCCAGACCCTTCTGGTGCATACATAAAAATTT
CGCTGCATGTGCCTGGTCATGCATTCTTTACAATTTCTTCTAAGTCATCTGCAACTCCAAATGCAAGGA
TTTTTTCACATCGAGCATGGTTTGGGTGGGGCCCCATCAAGCTCCTGGGGGGCTGTTGAGAGGGTTGTCC
AGAGTTCAGTTTGGTGCGGGCATGTTCAAATTTTGGTGTCCCCCCCCCCTCCCTCTTCTATGTCTGTGT
CATTTTTGGGGGGGGGGGGGGGGGGGGCATCAAGACTTGAACATGCCCGCACCAAACTGGACTCTGG
ACAACACTCTGGACAAAACCCAAAGCTTGATGGGGCCCACCCCACAAAACTATGCTCGTGTGGAAAAATC
CTTTGCATGTGCAGTATTGATGTCTTAAAAGAAAGAATTTTGGACATGGGTTACGCCTCATGCAGAAGTG
TAGGGTTGCCAAGCGGACGAGTTAGGTCGATGAGTTAACGTATGTGCAAGAAGCGTGTGGGCAAGGGTAA
GGTCAATGAGTTCATCTAGGGTAAGAAATGTTTACATGGAAAGGCAAACGCTGCAGCTATCTGACAGTTT
CTGTGTGTAAATGCTGGCTTCATGCATTTGTGGGGCGAGTCAAAATGATGTGCAGTCCACCTATTGGAT
CCCATCACCTCAATGGTACTACTGGATAAATTCATCTGCATACTACACCCTAGAAAGTCGTAGAGCAGGA
AAGACAAGAGCCCATACATTAAGTCAAGTGCTCTGTAACTGAAATGCAAGTTTCTAATCTGTTTGTCTTG
GGGTGGGTGGGTAGTTGTTCGTTGCGAGTGGACTACAGTCACCCTCTTTGACCCGCAGTGAAGACCTTTC
CAATCACATGGGCCTCTTCCTTCAGAAGACCAACATCATCCGCGACTACTTTGAGGACATCAATGAGCTG
CCTGCCCCCGGTGTGCAACTTGCATATGCTCTGTATTCGTGCGTATGTTGTTGGTTTGATAATGGCTAT
GCAAATGCCAGGTCAGTAATGTTGTGGTGTTCCGATAATAGATAGTGGACATTCGGAGAAAGGAGACTTT
CATTAGGGACTGAGTGGTTCAAATAATATGTGGGCTGCGCCCTGCTTTCTAGACGGCACAAATAGTGGAT
ACGTGTTATTTTGTTGAAATGATGGATGCAATGACATATTTGAACGCCTGACAGCTAATGGAAATGGGGT
TCTTGACAGGGTAGGTTACAATGCCTCCATCAACCCTCGTAAATGATGTAAGTACATTTTGCTCTATATT
TTGCTGACAAACATGTCATCTTTACTCTTCACCCCCTTCATCTCTGTGTGTGTGTGTGTGTGTGTGTGT
TGTGTGTGTTCTGGGGAAGTTGGGGAGGGGGAGACACTTGTGCTCTGGGAGCTAGGAGAATAGGTAGA
CTTGCCTTTCCACTTGAAAGGCTCTTCAACTGCAGAGTCAAACCTACCCTGCCTGGGTGTGAGAGTGTGC
ATACAAGGACACCATGCTCGATGGATAGGCCTCGAGTGTAGGCAGGTACCTCCCAGAAAACTGAGCTTGC
CAGGGAAGATGTGTGTGTGTGGGGGGCGGAGGGGTCATAGGAATATCACTTACAGGACTGTCCAAAACCG
GGCGTAAATGGGCATGGAACATGCTCATCCAGGATCCTGAGGGTACCGGTGGGGTTTGTCCTCGCAGGAT
```

Figure 13 continued

```
GTTCTGGCCCAGAGAGATCTGGGGCAAGTATGCGAACAACCTCGCTGAGTTCAAAGACCCGGCCAACAAG
GCGGCTGCAATGTGCTGCCTCAACGAGATGGTCACAGATGCATTGAGGCACGCGGTGTACTGCCTGCAGT
ACATGTCCATGATTGAGGATCCGCAGATCTTCAACTTCTGTGCCATCCCTCAG
```

Figure 14

```
                                   10        20        30        40        50        60        70
                              ....|....|....|....|....|....|....|....|....|....|....|....|....|....|
B. braunii_Berkeley SQS       MGMLRWGVESLQNPDELIPVLRMIYADKFGKIKPKDEDRGFCYEILNLVSRSFAIVIQQLPAQLRDPVCI
Exon_1                        -----------------------------------------------------
Exon_2                                                                             -------------------

80        90        100       110       120       130       140
                              ....|....|....|....|....|....|....|....|....|....|....|....|....|....|
B. braunii_Berkeley SQS       FYLVLRALDTVEDDMKIAATTKIPLLRDFYEKISDRSFRMTAGDQKDYIRLLDQYPKVTSVFLKLTPREQ
Exon_2                        -------------------------------------
Exon_3                                                              --------------------------------

150       160       170       180       190       200       210
                              ....|....|....|....|....|....|....|....|....|....|....|....|....|....|
B. braunii_Berkeley SQS       EIIADITKRMGNGMADFVHKGVPDTVGDYDLYCHYVAGVVGLGLSQLFVASGLQSPSLTRSEDLSNHMGL
Exon_4                        -------------------------------------------
Exon_5                                                                    ----------------------------

220       230       240       250       260       270       280
                              ....|....|....|....|....|....|....|....|....|....|....|....|....|....|
B. braunii_Berkeley SQS       FLQKTNIIRDYFEDINELPAPRMFWPREIWGKYANNLAEFKDPANKAAAMCCLNEMVTDALRHAVYCLQY
Exon_5                        ----------------------
Exon_6                                               -----------------------------------------------

290       300       310       320       330       340       350
                              ....|....|....|....|....|....|....|....|....|....|....|....|....|....|
B. braunii_Berkeley SQS       MSMIEDPQIFNFCAIPQTMAFGTLSLCYNNYTIFTGPKAAVKLRRGTTAKLMYTSNNMFAMYRHFLNFAE
Exon_6                        ----------------------------------------
Putative exons_7&8                                                    ------------------------------

360       370       380       390       400       410       420
                              ....|....|....|....|....|....|....|....|....|....|....|....|....|....|
B. braunii_Berkeley SQS       KLEVRCNTETSEDPSVTTTLEHLHKIKAACKAGLARTKDDTFDELRSRLLALTGGSFYLAWTYNFLDLRG
Putative exons_7&8            ----
Exon_9                             ----------------------------------
Exon_10                                                              ---------------------------------

430       440       450       460
                              ....|....|....|....|....|..|
B. braunii_Berkeley SQS       PGDLPTFLSVTQHWWSTLTFLTSTAVFFTPSRPSPRPTLSA*
Exon_10                       ........................................
```

Figure 15 (B. braunii Berkeley strain squalene synthase pSP124S construct, complete sequence, SEQ ID NO: 15). Lowercase nucleotides are the vector pSP124S, while uppercase nucleotides are the inserted synthesised Berkeley strain squalene synthase gene with inserted regulatory elements.

```
Gcacttttcggggaaatgtgcgcggaaccccctatttgtttatttttctaaatacattcaaatatgtatccgctcatgagacaat
aaccctgataaatgcttcaataatattgaaaaaggaagagtatgagtattcaacattccgtgtcgcccttattccctttttg
cgcatttgccttcctgttttttgctcacccagaaacgctggtgaaagtaaaagatgctgaagatcagttgggtgcacgagtgg
gttacatcgaactggatctcaacagcggtaagatccttgagagttttcgccccgaagaacgttttccaatgatgagcacttta
aagttctgctatgtggcgcggtattatcccgtattgacgccgggcaagagcaactcggtcgccgcatacactattctcagaatg
acttggttgagtactcaccagtcacagaaaagcatcttacggatgtgatgacagtaagagaattatgcagtgctgccataacca
tgagtgataacactgcggccaacttacttctgacaacgatcggaggaccgaaggagctaaccgcttttttgcacaacatggggg
atcatgtaactcgccttgatcgttgggaaccggagctgaatgaagccataccaaacgacgagcgtgacaccacgatgcctgtag
caatggcaacaacgttgcgcaaactattaactggcgaactacttactctagcttcccggcaacaattaatagactggatggagg
cggataaagttgcaggaccacttctgcgctcggcccttccggctggctcgtttattgctgataaatctggagccggtgagcgtg
ggtctcgcggtatcattgcagcactggggccagatggtaagccctcccgtatcgtagttatctacacgacggggagtcaggcaa
ctatggatgaacgaaatagacagatcgctgagataggtgcctcactgattaagcattggtaactgtcagaccaagtttactcat
atatactttagattgatttaaaacttcatttttaatttaaaaggatctaggtgaagatccttttttgataatctcatgaccaaaa
```

Figure 15 continued

```
tcccttaacgtgagttttcgttccactgagcgtcagaccccgtagaaaagatcaaaggatcttcttgagatccttttttttctgc
gcgtaatctgctgcttgcaaacaaaaaaaccaccgctaccagcggtggtttgtttgccggatcaagagctaccaactcttttttc
cgaaggtaactggcttcagcagagcgcagataccaaatactgtccttctagtgtagccgtagttaggccaccacttcaagaact
ctgtagcaccgcctacatacctcgctctgctaatcctgttaccagtggctgctgccagtggcgataagtcgtgtcttaccgggt
tggactcaagacgatagttaccggataaggcgcagcggtcgggctgaacgcgggggttcgtgcacacagcccagcttggagcgaa
cgacctacaccgaactgagatacctacagcgtgagctatgagaaagcgccacgcttcccgaagggagaaagcggacaggtatc
cggtaagcggcagggtcggaacaggagagcgcacgagggagcttccagggggaaacgcctggtatctttatagtcctgtcgggt
ttcgccacctctgacttgagcgtcgatttttgtgatgctcgtcaggggggcggagcctatggaaaaacgccagcaacgcggcct
ttttacggttcctggccttttgctggccttttgctcacatgttcttcctcgcgttatcccctgattctgtggataaccgtatta
ccgcctttgagtgagctgataccgctcgccgcagccgaacgaccgagcgcagcgagtcagtgagcgaggaagcggaagagcgcc
caatacgcaaaccgcctctccccgcgcgttggccgattcattaatgcagctggcacgacaggtttcccgactggaaagcgggca
gtgagcgcaacgcaattaatgtgagttagctcactcattaggcaccccaggctttacactttatgcttccggctcgtatgttgt
gtggaattgtgagcggataacaatttcacacaggaaacagctatgaccatgattacgccaagctcgaaattaaccctcactaaa
gggaacaaaagctgGAGCTCcagcttttgttccccttgatggggtatttgagcacttgcaacccttatccggaagcccctggcc
cacaaaggctaggcgccaatgcaagcagttcgcatgcagccccctggagcgctgccctcctgataaaccggccagggggcctatg
ttctttacttttttttacaagagaagtcactcaacatcttaaaATGGGtgactcgacgagcaagcccggcggatcaggcagcgtg
cttgcagatttgacttgcaacgcccgcattgtgtcgacgaaggcttttggctcctctgtcgctgtctcaagcagcatctaaccc
tgcgtcgccgtttccatttgcagGATGCTTCGCTGGGGAGTGGAGTCTTTGCAGAATCCAGATGAATTAATCCCGGTCTTGAGG
TGAGTCGACGAGCAAGCCCGGCGGATCAGGCAGCGTGCTTGCAGATTTGACTTGCAACGCCCGCATTGTGTCGACGAAGGCTTT
TGGCTCCTCTGTCGCTGTCTCAAGCAGCATCTAACCCTGCGTCGCCGTTTCCATTTGCAGGATGATTATGCTGATAAGTTTGG
AAAGATCAAGCCAAAGGACGAAGACCGGGGCTTCTGCTATGAAATTTTAAACCTTGTTTCAAGAAGTTTTGCAATCGTCATCCA
ACAGCTCCCTGCACAGCTGAGGGACCCAGTCTGCATATTTTACCTTGTACTACGCGCCCTGGACACAGTCGAAGATGATATGAA
AATTGCAGCAACCACCAAGATTCCCTTGCTGCGTGACTTTTATGAGAAAATTTCTGACAGGTCATTCCGCATGACGGCCGGAGA
TCAAAAAGACTACATCAGGCTGTTGGATCAGTACCCCAAAGTGACAAGCGTTTTCTTGAAATTGACCCCCCGTGAACAAGAGAT
AATTGCAGACATTACAAAGCGGATGGGGAATGGAATGGCTGACTTCGTGCATAAGGGTGTTCCCGACAGTGGGGGACTACGA
CCTTTACTGCCACTATGTTGCTGGGGTGGTGGGTCTCGGGCTTTCCCAGTTGTTCGTTGCGAGTGGACTACAGTCACCCTCTTT
GACCCGCAGTGAAGACCTTTCCAATCACATGGGCCTCTTCCTTCAGAAGACCAACATCATCCGCGACTACTTTGAGGACATCAA
TGAGCTGCCTGCCCCCCGGATGTTCTGGCCCAGAGAGATCTGGGGCAAGTATGCGAACAACCTCGCTGAGTTCAAAGACCCGGC
CAACAAGGCGGCTGCAATGTGCTGCCTCAACGAGATGGTCACAGATGCATTGAGGCACGCGGTGTACTGCCTGCAGTACATGTC
CATGATTGAGGATCCGCAGATCTTCAACTTCTGTGCCATCCCTCAGACCATGGCCTTCGGCACCCTGTCTTTGTGTTACAACAA
CTACACTATCTTCACAGGGCCCAAAGCGGCTGTGAAGCTGCGTAGGGGCACCACTGCCAAGCTGATGTACACCTCTAACAATAT
GTTTGCGATGTACCGTCATTTCCTCAACTTCGCAGAGAAGCTGGAAGTCAGATGCAACACCGAGACCAGCGAGGATCCCAGCGT
GACCACCACTCTGGAACACCTGCATAAGATCAAAGCTGCCTGCAAGGCTGGGCTGGCACGCACAAAAGATGACACCTTTGACGA
ATTGAGGAGCAGGTTGTTAGCGCTGACGGGAGGCAGCTTCTACCTCGCCTGGACCTACAATTTCCTAGACCTTCGAGGCCCGGG
AGACCTGCCCACCTTCTTATCTGTAACCCAACATTGGTGGTCTATTCTGATCTTCCTCATTTCGATTGCCGTCTTCTTTATTCC
GTCGAGGCCCTCACCTAGACCCACACTCAGCGCCTAAccgacgtcgacccactctagaggatcgatccccgctccgtgtaaatg
gaggcgctcgttgatctgagccttgccccctgacgaacggcggtggatggaagatactgctctcaagtgctgaagcggtagctt
agctccccgtttcgtgctgatcagtcttttttcaacacgtaaaaagcggaggagttttgcaattttgttggttgtaacgatcctc
cgttgattttggcctcttttctccatgggcgggctgggcgtatttgaagcccactagttctagaGCGGCCGCtctagaactagtg
gatccccccgggctgcaggaattcgatatcaagcttatcgataccgtcgacctcgagatttaaatgccagaaggagcgcagccaa
accaggatgatgtttgatggggtatttgagcacttgcaacccttatccggaagcccctggcccacaaaggctaggcgccaatg
caagcagttcgcatgcagcccctggagcggtgccctcctgataaaccggccagggggcctatgttctttacttttttttacaagag
aagtcactcaacatcttaaaATGGCCAGtgagtcgacgagcaagcccggcggatcaggcagcgtgcttgcagatttgacttgc
aacgcccgcattgtgtcgacgaaggcttttggctcctctgtcgctgtctcaagcagcatctaaccctgcgtcgccgtttccatt
tgcagGATGGCCAAGCTGACCAGCGCCGTTCCGGTGCTCACCGCGCGCGACGTCGCCGGAGCGGTCGAGTTCTGGACCGACCGG
CTCGGGTTCTCCCGGGACTTCGTGGAGGACGACTTCGCCGGTGTGTCCGGGACGACGTGACCCTGTTCATCAGCGCGGTCCAG
GACCAGgtgagtcgacgagcaagcccggcggatcaggcagcgtgcttgcagatttgacttgcaacgcccgcattgtgtcgacga
aggcttttggctcctctgtcgctgtctcaagcagcatctaaccctgcgtcgccgtttccatttgcagGACCAGGTGGTGCCGGA
CAACACCCTGGCCTGGGTGTGGGTGCGCGGCCTGGACGAGCTGTACGCCGAGTGGTCGGAGGTCGTGTCCACGAACTTCCGGGA
CGCCTCCGGGCCGGCCATGACCGAGATCGGCGAGCAGCCGTGGGGCGGGAGTTCGCCCTGCGCGACCCGGCCGGCAACTGCGT
GCACTTCGTGGCCGAGGAGCAGGACTAAccgacgtcgacccactctagagcatcgatccccgctccgtgtaaatggaggcgctc
gttgatctgagccttgcccctgacgaacggcggtggatggaagatactgctctcaagtgctgaagcggtagcttagctccccg
tttcgtgctgatcagtcttttttcaacacgtaaaaagcggaggagttttgcaattttgttggttgtaacgatcctccgttgattt
tggcctcttttctccatgggcgggctgggcgtatttgaagcttaattaactcgagggggggcccGGTACCcaattcgccctatag
tgagtcgtattacaattcactggccgtcgttttacaacgtcgtgactgggaaaaccctggcgttacccaacttaatcgccttgc
agcacatccccctttcgccagctggcgtaatagcgaagaggcccgcaccgatcgcccttcccaacagttgcgcagcctgaatgg
cgaatggaaattgtaagcgttaattattttgttaaaattcgcgttaaatttttgttaaatcagctcatttttttaaccaataggcc
gaaatcggcaaaatcccttataaatcaaaagaatagaccgagatagggttgagtgttgttccagtttggaacaagagtccacta
ttaaagaacgtggactccaacgtcaaagggcgaaaaaccgtctatcagggcgatgccccactacgtgaaccatcaccctaatca
agttttttggggtcgaggtgccgtaaagcactaaatcggaaccctaaaggagcccccgatttagagcttgacggggaaagccg
gcgaacgtggcgagaaaggaagggaagaaagcgaaaggagcgggcgctagggcgctggcaagtgtagcggtcacgctgcgcgta
accaccacacccgccgcgcttaatgcgccgctacagggcgcgtcaggtg
```

Figure 16 (primer pair 1, primer 1, SEQ ID NO: 16).

CCTTGATGGGGTATTTGAGCAC

Figure 17 (primer pair 1, primer 2, SEQ ID NO: 17).

GGAATTCGGTTAGGCGCTGAGTGTGGGTCTAGG

Figure 18 (primer pair 2, primer 1, SEQ ID NO: 18).

TGAGCACTTGCAACCCTTATCCG

Figure 19 (primer pair 2, primer 2, SEQ ID NO: 19).

GGAATTCGGTTAGGCGCTGAGTGTGGGTCTAGG

Figure 20 (SEQ ID NO: 20; encoded by Exon 7.7).

ILEGLTEKVRQRKGRIARLVMSSRNVPGLFRTCLKLAKNFEA

Figure 21 (SEQ ID NO: 21; encoded by Exon 1.7).

MSMHQDKGVAKDLLRHPGEFPYLLQLAATTYGTPAAPIPKEPDRAFCYNTLHAVSK

Figure 22 (SEQ ID NO: 22; encoded by Exon 2.1).

FPRFVHRLPLELQDPICIFYLLLRALDTVEDDMNLPSKVKVDLLREFHEHCKD

Figure 23 (SEQ ID NO: 23; encoded by Exon 3.11).

NWSMKSDYGIYADLMERFPLVISVLEKLPKPTQE

Figure 24 (SEQ ID NO: 24; encoded by Exon 4.1).

VFVENVKYMGNGMADFIDKEILTVDEYDLYCHYVAGSCGIAVVK

Figure 25 (SEQ ID NO: 25; encoded by Exon 5.3).

VIVQFNLATPEADSMEFSNSLGLLLQKANIITDYNEDINEEPRP

Figure 26 (SEQ ID NO: 26; encoded by Exon 6.1).

MFWPQEIWANYSEKLADFNEPANLEKAMKCLNHMVTDALRHIEPSLKGMVYFTDGTVFRA
LALLLVTAFGHLSTLYNNPNVFR

Figure 27 (SEQ ID NO: 27; encoded by Exon 7.10).

KVRQRKGRIARLVMSSRNVPGLFRTCLKLAKNFEA

Figure 28 (SEQ ID NO: 28; encoded by Exon 9.2).

CLEETKNDPSVATTIKRLQSIQATCREGLEKYETPSGLRALCAAPSPTK*

Figure 29 (SEQ ID NO: 29; ATB1 triterpenoid hydrocarbon synthetic polypeptide sequence).

MSMHQDKGVAKDLLRHPGEFPYLLQLAATTYGTPAAPIPKEPDRAFCYNTLHAVSKGFPR
FVHRLPLELQDPICIFYLLLRALDTVEDDMNLPSKVKVDLLREFHEHCKDRNWSMKSDYG
IYADLMERFPLVISVLEKLPKPTQEVFVENVKYMGNGMADFIDKEILTVDEYDLYCHYVA
GSCGIAVVKVIVQFNLATPEADSMEFSNSLGLLLQKANIITDYNEDINEEPRPRMFWPQE
IWANYSEKLADFNEPANLEKAMKCLNHMVTDALRHIEPSLKGMVYFTDGTVFRALALLLV
TAFGHLSTLYNNPNVFREKVRQRKGRIARLVMSSRNVPGLFRTCLKLAKNFEARCLEETK
NDPSVATTIKRLQSIQATCREGLEKYETPSGLRALCAAPSPTK*

Figure 30 (SEQ ID NO: 30; *ATB1* triterpenoid hydrocarbon synthetic nucleic acid sequence (cDNA)).

ATGAGTATGCACCAAGACAAGGGGGTTGCTAAGGATCTTTTAAGGCATCCAGGGGAATTCCCCTATTTGCTCCAG
CTAGCCGCTACAACTTACGGCACACCGGCGGCCCCGATCCCAAAGGAACCCGACCGAGCGTTCTGCTATAACACT
CTTCACGCTGTTTCTAAAGGGTTCCCGAGGTTTGTTCACAGGCTTCCTCTGGAACTCCAGGATCCAATCTGCATT
TTTTATCTCCTGCTGCGTGCACTAGATACAGTGGAGGATGATATGAACCTCCCAAGTAAGGTGAAGGTAGATCTG
TTGCGCGAGTTTCATGAGCATTGTAAAGACAGGAACTGGAGCATGAAAAGTGATTATGGCATCTATGCAGACTTG
ATGGAAAGGTTTCCTCTGGTGATTTCCGTCCTGGAAAAGCTTCCTAAGCCCACACAGGAGGTTTTTGTGGAGAAT
GTCAAATATATGGGCAATGGCATGGCAGACTTTATTGATAAGGAGATCTTGACTGTGGATGAGTACGATCTGTAC
TGCCACTATGTGGCTGGTAGTTGTGGCATTGCTGTTGTCAAGGTTATTGTCCAATTTAACCTTGCCACGCCGGAA
GCTGACTCGATGGAGTTTTCCAACAGCCTAGGATTGTTGCTTCAGAAAGCCAACATCATTACTGACTACAATGAG
GACATTAACGAAGAACCCAGACCCCGGATGTTCTGGCCCCAAGAGATCTGGGCCAATTACTCGGAAAAGTTAGCT
GACTTTAATGAACCCGCCAACCTTGAAAAAGCTATGAAGTGCTTGAACCACATGGTCACAGATGCCCTGCGCCAC
ATTGAGCCATCTCTTAAGGGCATGGTTTATTTCACAGACGGGACAGTCTTCCGCGCTCTTGCTCTTCTGCTGGTC
ACAGCTTTTGGTCACTTGTCGACTTTGTACAATAACCCAAATGTTTTCCGAGAGAAGGTGAGGCAGCGGAAGGGA
AGGATTGCCCGGCTAGTGATGTCATCCAGAAACGTACCAGGCCTCTTCCGCACCTGCCTAAAACTTGCAAAGAAC
TTTGAAGCCAGGTGTCTGGAGGAGACAAAGAATGATCCCTCTGTGGCCACAACCATCAAGCGGCTGCAGTCAATC
CAGGCCACGTGCAGAGAAGGCCTGGAAAAATATGAGACACCATCTGGGCTGAGGGCGCTCTGTGCTGCTCCAAGC
CCTACAAAGTGA

Figure 31 (SEQ ID NO: 31; *ATB1* triterpenoid hydrocarbon synthetic nucleic acid sequence (genomic)).

GCGCGCGCGCGTGTCTGTGCGAGTAATCTCCGCCTCCACATTTCCCCCTTCTAGTGTAAGAAGGATTCCATGA
GCTTTGGGGTTCAAGGAAAATGAAGTGCATTTCACCCAGATCGTTTGGGACTAGTAGGGTGTTACCCATACTTCT
GTTAAGAATTCCTCACCAACAAGATCTTCTAAATGTTTGGCCATCTGAATTCATATTCTCATAAAACCCAGGGCA
GGCTTGGAAGTATGAAAGAACAGAGAAGGTACATCCGGGGAGCCACTGAAGCCTGGGGGATGGAGCGACTCCCAT
ATCGACCGACATGTGAGTGCAAGGAAGAAAGTCTTGACACCCTCGGAGCTTGGTATATTTTTTTTTTGTATCTA
AAAGTCTTTTTTCTCTGAGTAGATATAAACGAAGAAATGAAGCATATATATCCAGGTCGTAGCATGAGGGCGATA
TATTTCACTCTCGTTAGGTAAGATACTTTTATTGCGGGGATAGGTTTTACTGCGTAATTGACAGCCCGATCACC
TGATCGGGCGTAAAACCTAACAGAAGCCCCGCTGAGCCTCACGTCATCATCATCATTCTTGCTGCTGTGAAGCAT
GCTGGCCTCACGTTGACTAGGGTTGAATAAATTTTAACAAGAGGGACTAGAAGGTGAGGCCGAGACAACAGCAGC
GTGTAACGGGGGACAACGCAAAACCTTGGTATGTAGTCTGGGGGGTCGGCATTGTGGACATTTTGAAGAGCTCA
CGGGCCAGATGCTAGATAAATCTTGTGTCAAGTGTAGGCAAAAAGATGCAGGAATTCTTGTGTCACGAATAGGGG
AAAGCAATGCAGGGATTTGAGATTGCGAGAAATGAGTAACCCAAAATTCGTGCTGCGTTTAGCGCGTAAGAATTA
TCAGTCAGCTTCCCTGCATCAATTGATGTAGGGCCTAGGCAGGCGATGATGACATTGAAAGTTGTCGTCAGATGG
ACTGACTGATCGTCCATAAACCAGCCGCTGAAATCCATCTCCGTCTCCAGCCGTTAAACCCCGCCCCGATGGTTG
GCCGAAATTGGGTCAGCGTCCCCGCGTCGGCCCGTGTCGTCCTAGCGAGAGCAATCGTCCTTGGACAACGGCAAC

Figure 31 continued

```
CGTTTTCGAATTGGTGTGCATGCTGCCAGCCATATGAGGAAACAGCAAGCCTAAGGTTGTTACTCTTAGGCCTCA
TAAAGTAGGAGTATAGCGATCCCCCGTCTGCAGGCCGGCGAAGACTCCGCGAGATCCGGAGGAGAGAAATAGGCC
ACAATGAGTATGCACCAAGACAAGGGGGTTGCTAAGGATCTTTTAAGGCATCCAGGGGAATTCCCCTATTTGCTC
CAGCTAGCCGCTACAACTTACGGCACACCGGCGGCCCCGATCCCAAAGGAACCCGACCGAGCGTTCTGCTATAAC
ACTCTTCACGCTGTTTCTAAAGGGTGAGATATTGCTGAATTGCTTTCACTTACTTCCAATTCAACTGGCAAACTG
TGGAATTGGAAAAGAGTGGCGTTCTGGAACGTGAAGGCTACGAGTTATCGAGACAGAAGTTGTTTAACTTGACCG
CAATCTTCCAGCGGTTCCTCTTCTGTTTCTCTTTTAAATAGGGCCCATAGGATCCCGTTTCTCTTTTTATGTTA
ATTCCGGGGATCTCATTTGTACATCTGTGTCTGTTTGTTCGCACGGGTATATACTCTCTTTCGGGGTTGAGTGTT
ACCTCTATGTTTTGTGTGGATTTCAATCTAGATTTTAGTGATGTTGACGATCTGTTTGAAATTGCATCAGCTCAT
CCCCTGTAAGAGCAGGGTGGCTGTCCCTACTGATGGGTTTCTCTGGTGTCTGCAGGTTCCCGAGGTTTGTTCACA
GGCTTCCTCTGGAACTCCAGGATCCAATCTGCATTTTTTATCTCCTGCTGCGTGCACTAGATACAGTGGAGGATG
ATATGAACCTCCCAAGTAAGGTGAAGGTAGATCTGTTGCGCGAGTTTCATGAGCAGTTGTAAAGACAGGTGCGTCC
CTTGTTCTCATGGAACTAGATAACAGCAAATGCACATATTCTACAGAGGAGTGTTTTTCTGTGTGTCTGTGTTAC
TGCGCTGACACGCACTTGACCCCTCCCCGTTCTTCGCTCCAGTTTGCTTCCCTCTTTTCCGCTTCTTCTGCTTCT
GACCCTACCTAACACTCCAAATCCAACCCCCTCCCCCCCCCCCAAAAAAAAAAAAAAAAGAAGGGACTACTGTGT
GTGAACGTTCACCATCCTCGCCTCTGCTGGGAGTGGGATTCTGGTTTCTGACACACACACACACAGCCAAGAAGA
GCAAGAAGGACGAAGGGACTACTGTGTGTGAAGGGTCAACATCCTCGACTCTGATGGTTGTGGGATGATGGTTTC
TGACTTTTTGACTCATTGTGAGCATAATCTGGGGGTAATTCAACTTTTTTTCTTGCTCTAGGACTTTGTAAATAC
CCTGACAATGTATCTGCCTACAGTTTCTACTCCATTTCGAGATGTGCTAAGTTCACAAACGAGTTCCTTGTATGC
AGGAACTGGAGCATGAAAAGTGATTATGGCATCTATGCAGACTTGATGGAAAGGTTTCCTCTGGTGATTTCCGTC
CTGGAAAAGCTTCCTAAGCCCACACAGGAGGTAGGAAAGAAGCTGTAGCCCAAGCTTTTTGAGCGAGCTTATCTG
AGTGCTCGAACGGGTACTCAGCTTGGGTCCTTCCTACATGTGGCTGGCGAGAACACTAACAGTTGCAATGAAGAG
TTCTTCAGGAGGATTGCTGGCTGCCATGTCTTGTTTTGTTGTCCAGAGGAGTTTTCAGCTACGTTTGAAATGCTA
CTGTTGTACCTAAAGTGGAGAATGTAGGGAAAGTCAGTTGTCGTCCCCCTCTTTTTTCTGTTTGAGTTGTGTTCC
CATTATTCAATAGCATTTCCTGATGGTTGTATGGTGGATGTCTTGCATCCCAGATACAAATACAAGCCAATTTTG
CAGGAGAGCACTCCTGAAGATGGTGTCCTTCCACTGTTGTCACGGACGAGGGGTGCTGAATGTTGTGGGCACAAA
CAGCAGTGCATCCCATACATGGAATGTTGTTGTCTACACGTTGACACGTTCCAAGCATCACTAGCTGCCCTCCTG
ATACTCTTCTCGGTCATCTAAGCTCACGCATCCGAACATGGCACTTTACAAAAGAAACAGTGTTTTTTGACGTT
GAACAGGTTTTTGTGGAGAATGTCAAATATATGGGCAATGGCATGGCAGACTTTATTGATAAGGAGATCTTGACT
GTGGATGAGTACGATCTGTACTGCCACTATGTGGCTGGTAGTTGTGGCATTGCTGTTGTCAAGGTACGTACTCTC
TAACATAGTCTGGTACCCCAGTTTTGCCTCTGCAGATGTTATTGCAAGTGGCTTCCACGAACACCATGGGCTCC
TGGTGCAGTCCAACTTGCGAGGTCATGGGCTTGAAGTCGCCCTGTCTACGGAACACCCGATTCATGACCAAGGTT
ACATAATATCGTTGTTCCTTAATTCGGAATACTAAAGTTAAGGTTTCGGAACGTCTACCCTAAGCCCTAGAACAC
CGCCAATTGGCCTGGGAGACATTTCTAGTGTGTTTTCTGGTCTTGCGAGGATGTTTCCAGAGCCTTTCCGATCTA
CCAATGGTACAGTTTACGTAATGCTTCAGGTGAACTGTAGACTGTGGGGGGTGGAAGTGGAGTGGTGTCCAATGT
TGTAATGCACTTTGTAATCTGAGAGCCAGGTTCTGGCTCCTGTATTGTGGGGGCTGCTCTGTTGTCTATTACACA
ACTAGAGTTGTATGTAGCCAGTGGCAGTTGTGAGTTGGATGGGACTGTGGGACCAGGTTATTGTCCAATTTAACC
TTGCCACGCCGGAAGCTGACTCGATGGAGTTTTCCAACAGCCTAGGATTGTGCTTCAGAAAGCCAACATCATTA
CTGACTACAATGAGGACATTAACGAAGAACCCAGACCCCGGTATGCCACTAGCATATTCAGAGACACATGGCTCT
GTACACAATCTTACTGTAAAAATGACTGAAAGGAGTGGCTGCAATGTTTTGTCTGTCAAACCTATCAGGGCAAGT
CGACTTGAAGGTCTGGTTCGCAATATGGGTTTTGCATGGTCACGTTTAGAGTATGTGGTAACGATTGATATCTCC
TCTGAAGTGCCATTTGCTGTATGTATGGAGTGGCCGTCAGAAGTCCCAGGATAAGAGCAACTGGTTATTGTCAAA
AACTTTGACTGGGTACATTGGGAGTTCCTGCAGGATGTTCTGGCCCCAAGAGATCTGGGCCAATTACTCGGAAAA
GTTAGCTGACTTTAATGAACCCGCCAACCTTGAAAAAGCTATGAAGTGCTTGAACCACATGGTCACAGATGCCCT
GCGCCACATTGAGCCATCTCTTAAGGGCATGGTTTATTTCACAGACGGGACAGTCTTCCGCGCTCTTGCTCTTCT
GCTGGTCACAGCTTTTGGTCACTTGTCGACTTTGTACAATAACCCAAATGTTTTCCGAGGTATAATATCTTTGCC
GTGTCTGGTGCTCGCACTCACAAGGGTGTCATAATAATCTAGCTTTCCCTGTCAGAATGAAGTCCAGATACTCTT
GGGACATCTGTGCCTCCAATCTTGGTTGTAGGGTGTGAATGCTGTTTCCGGCTCTGATGGATGCGCTAACATAGT
TTTGAGCTAGTGTACTTGCTTCCACATGGGGTTCTAACCTGACTCTTCTTCAAGCAGTGTGTACATGTTTTGTTG
GAGGCTTTGGTGGACATTGTGCCTATGACAGAAAGTCAAAGGTCGCTGGCCAGTTAAGTGCAGAAGGTGCTTAGA
GTCACTCTTAAATCAGGGAATGTGAGCGAACAACATGCACACCGATCATGATTAAGGGCCACGGATGATGTCTTT
GGTAAAGCAAGTACGCGTATTTAGAATGTGTCTGCAAAAAACTTGTTTTCCTGTGTTTAAGTGCCTTTGAAGCC
GTCCGTCACAGGGATTGTAGTAATTCTGTGAATTGGAAGGATTTAAACCCATTGTAAATTGTTTTTTTCTGCCGG
CCAGTCCAGCTTGACTGCTGAGACACACATCACATGTTAACAGGTACATTACCATGCAGAACATTTTATGTGGGG
ACCGCATAATCAGCAATTACGTTTTATATGGAACAGTTTGTACAACTGGCAGTTTCCAATCTCACCCACACTTTG
CTCCTCAACACTCACGTCGACTTAAATGCTGTGGAGACCAAAAACATCGATGGCATTCTGAGTCTTCCCTTTACA
ATGTCCACAGTGATGTAGTCAATTGAGGGAGGGGTACAGGAGACTCTGTAGATCTTGTATCCACTCCCCACAGCA
CTTGAAACCGTTGTTTGGAAGCTGATTTGAGCTTTTTAGGCATGTGAGCTAGTCTCTCAAGGTGGTTCCTGATGA
```

Figure 31 continued

```
TTGAATGCATTTTGGAGGGTTTGACAGAGAAGGTGAGGCAGCGGAAGGGAAGGATTGCCCGGCTAGTGATGTCAT
CCAGAAACGTACCAGGCCTCTTCCGCACCTGCCTAAAACTTGCAAAGAACTTTGAAGCCAGGTATATGCCCCTCT
GCCTTTGGAACAAACCCTGACGGTTGATTTACTGTAAAGAATAGCAGTCCTGTGTGTCATTTGTCTCTTGTGGGG
CCAAAGTTCCCTTGTGTAAGAATGGCAGTCTGGCACAGCTTGAGATTTATATCTTGTCTGAGTATCAGCTTTAAG
TATACTTCAGTGCTCCACATTGGTACCCCATCTACATTCTCCAGCATCCTGTAGGGCTTGATACATGGAAGGAGA
TACTTCCCACATGTCTCTCCCCTTTTCTCAAGAGAGGCAGCCATCTTTGGAGTTATGAGTTACAATCAGGCTCCA
ACTTGGACCTCTCAATGGAATCTTGCATGCACAGGAGCATATAGCTTGCCTCAAATATAGAGATAACTCAGTTTA
GCCCTGGCTGTCTGATTTTCTGCCCCGAACGGGAGGGTCTCCAACGCAGATGGCGGAGAACCACCGGAAATGTGA
TTTCTCCAAGTAATCTTTGTGTTTGACAAAGTGGTTCGGCCGGACATACATTCGGTCACTGTATGACATGAGATG
CGCTGCAGGTGTCTGGAGGAGACAAAGAATGATCCCTCTGTGGCCACAACCATCAAGCGGCTGCAGTCAATCCAG
GCCACGTGCAGAGAAGGCCTGGAAAAATATGAGACACCATCTGGGCTGAGGGCGCTCTGTGCTGCTCCAAGCCCT
ACAAAGTGAGGTCAATAGAAATATGGTAAGTTTTAACTCTTGCTCCACGTGCAAGACGCTGCAATCCTAGTACTC
CGTGCTGTACCATGTGATAGGAACTTCAAATGGCAGGCAATTGCAGTGGTTGCTGGGTCTGGGGACACATTCGGC
TCCCCTCTATCTATGCTTTACTTGCTGTGTCCTTTCAATTCCCTGATGCATTCAGTATCCCTTCTTCAAACAATT
AGTATGATGGTATTCCAAAGCTCGATGATTGCACATGTTATGCATGCACACATTAATGGTAAGTTTAAAGTGCAC
AGATGGTTGCAGGCTGTGTGGGCCAGTTTGTGCTTTTGCTTAGAACTAATCCATTGTACGTCCCCACCCCTAC
```

Figure 32 (SEQ ID NO: 32; ATB1 triterpenoid hydrocarbon synthetic nucleic acid sequence (synthetic gene for cloning)).

```
CACCACATGCATATGAGTATGCACCAAGACAAGGGGGTTGCTAAGGATCTTTTAAGGCATCCAGGGGAATTCCCC
TATTTGCTCCAGCTAGCCGCTACAACTTACGGCACACCGGCGGCCCCGATCCCAAAGGAACCCGACCGAGCGTTC
TGCTATAACACTCTTCACGCTGTTTCTAAAGGGTTCCCGAGGTTTGTTCACAGGCTTCCTCTGGAACTCCAGGAT
CCAATCTGCATTTTTTATCTCCTGCTGCGTGCACTAGATACAGTGGAGGATGATATGAACCTCCCAAGTAAGGTG
AAGGTAGATCTGTTGCGCGAGTTTCATGAGCATTGTAAAGACAGGAACTGGAGCATGAAAAGTGATTATGGCATC
TATGCAGACTTGATGGAAAGGTTTCCTCTGGTGATTTCCGTCCTGGAAAAGCTTCCTAAGCCCACACAGGAGGTT
TTTGTGGAGAATGTCAAATATATGGGCAATGGCATGGCAGACTTTATTGATAAGGAGATCTTGACTGTGGATGAG
TACGATCTGTACTGCCACTATGTGGCTGGTAGTTGTGGCATTGCTGTTGTCAAGGTTATTGTCCAATTTAACCTT
GCCACGCCGGAAGCTGACTCGATGGAGTTTTCCAACAGCCTAGGATTGTTGCTTCAGAAAGCCAACATCATTACT
GACTACAATGAGGACATTAACGAAGAACCCAGACCCCGGATGTTCTGGCCCCAAGAGATCTGGGCCAATTACTCG
GAAAAGTTAGCTGACTTTAATGAACCCGCCAACCTTGAAAAAGCTATGAAGTGCTTGAACCACATGGTCACAGAT
GCCCTGCGCCACATTGAGCCATCTCTTAAGGGCATGGTTTATTTCACAGACGGGACAGTCTTCCGCGCTCTTGCT
CTTCTGCTGGTCACAGCTTTTGGTCACTTGTCGACTTTGTACAATAACCCAAATGTTTTCCGAGAGAAGGTGAGG
CAGCGGAAGGGAAGGATTGCCCGGCTAGTGATGTCATCCAGAAACGTACCAGGCCTCTTCCGCACCTGCCTAAAA
CTTGCAAAGAACTTTGAAGCCAGGTGTCTGGAGGAGACAAAGAATGATCCCTCTGTGGCCACAACCATCAAGCGG
CTGCAGTCAATCCAGGCCACGTGCAGAGAAGGCCTGGAAAAATATGAGACACCATCTGGGCTGAGGGCGCTCTGT
GCTGCTCCAAGCCCTACAAAGATGCATTGATCACTCGAGCCCGGG
```

5' Key (upstream of start codon):
2xHis = double underscore i.e. CACCAC
NsiI = single underscore i.e. ATGCAT
NdeI = italic i.e. *CATATG*
NATIVE START = bold italic i.e. *ATG*

3' Key (sequences flanking stop codon):
NsiI = single underscore i.e. ATGCAT
STOP = bold italic i.e. *TGA*
BclI = italic i.e. *TGATCA*
XhoI = double underscore i.e. CTCGAG
SmaI = broken underscore i.e. CCCGGG Figure 33 (PCR products of untransformed (lane 1) and transformed (lanes 4-23) Chlamydomonas cells).
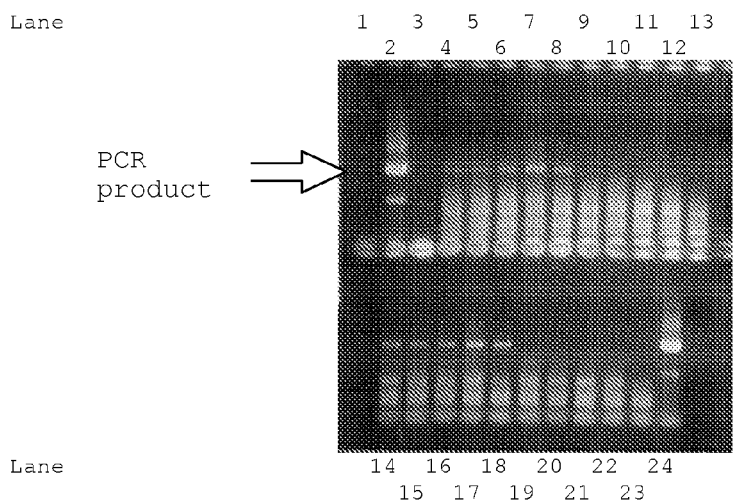
Figure 34 (Restriction digests of constructs 2, 3 and 4 showing expected fragment sizes).
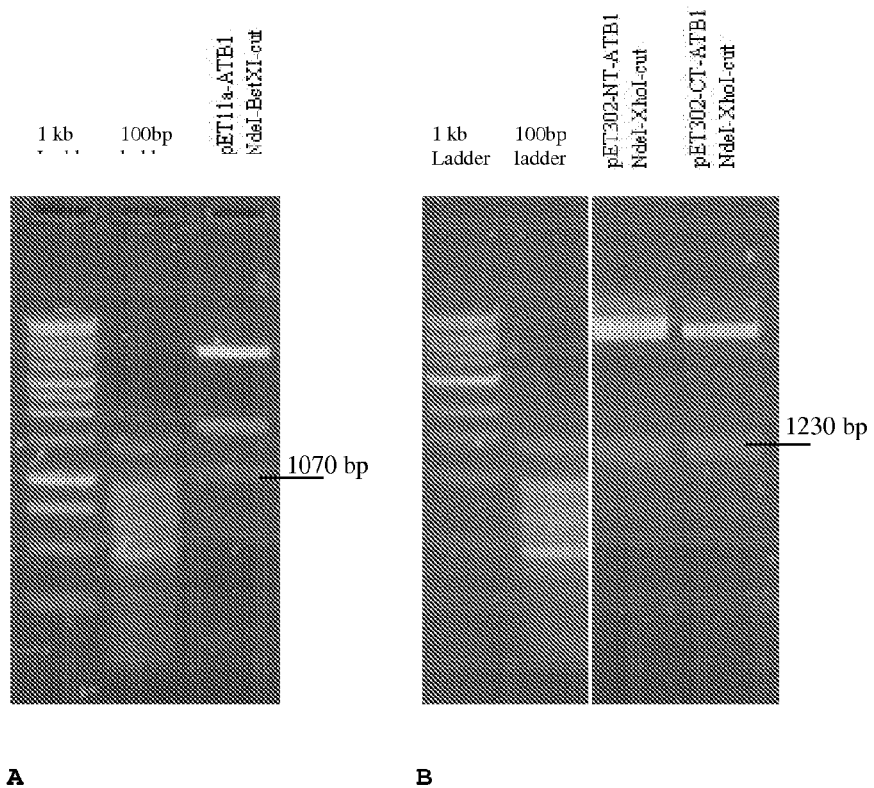

Figure 35. SDS-PAGE of Coomassie visualised proteins of whole untransformed (U) E. coli and whole E. coli transformed (T) with construct 2 (Lanes 1 to 6) and supernatant of a cell lysate of E. coli transformed (T) with construct 2 (Lanes 8 and 9). E. coli were induced with IPTG (1 mM) for 0 h (Lanes 1 and 2), 2 h (Lanes 3 and 4) or 4 h (Lanes 5, 6, 8 and 9). Arrows lane 7: prestained molecular weight markers (top to bottom kDa 175, 80, 58, 46, 30, 25, 17, 7) upper arrow 46 kDa, lower arrow 30 kDa. Arrow lane 9: soluble ATB1 protein.

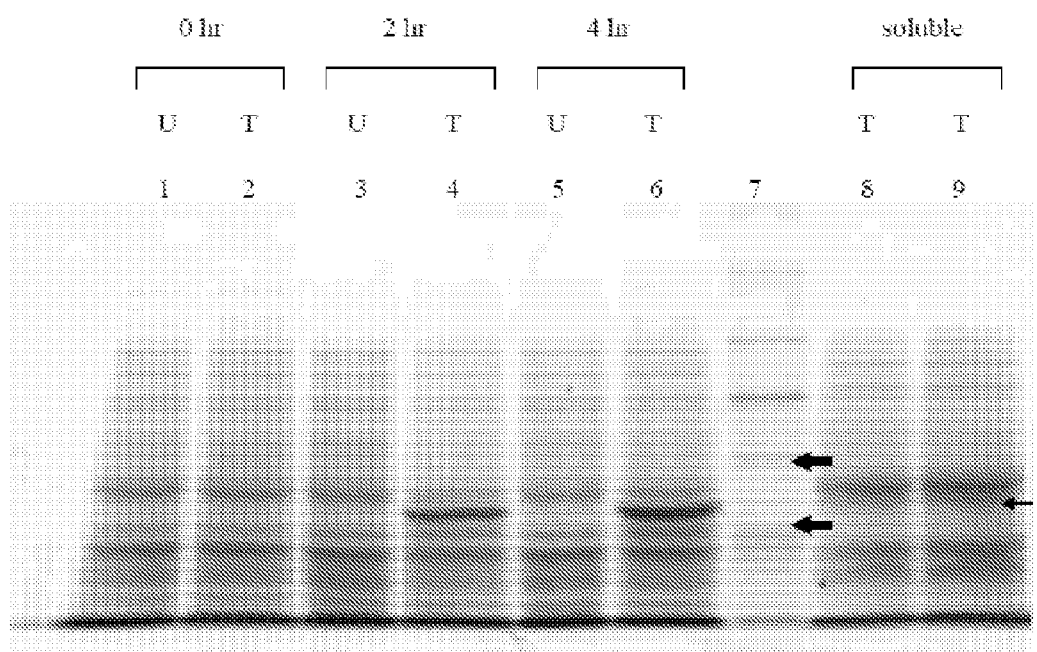

Figure 36. Conversion of two farnesyl pyrophosphate $C_{15}$ units to the squalene $C_{30}$ unit by the enzyme squalene synthase, or to the botryococcene $C_{30}$ unit by the enzyme botryococcene synthase, each with NADPH cofactor.
A.
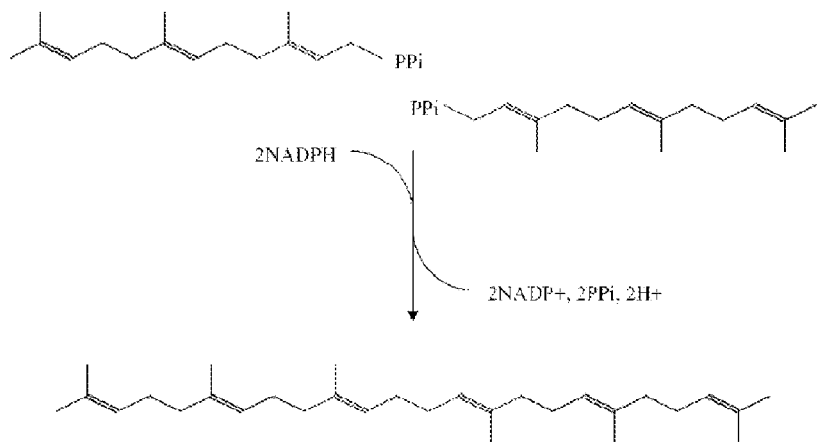
B.
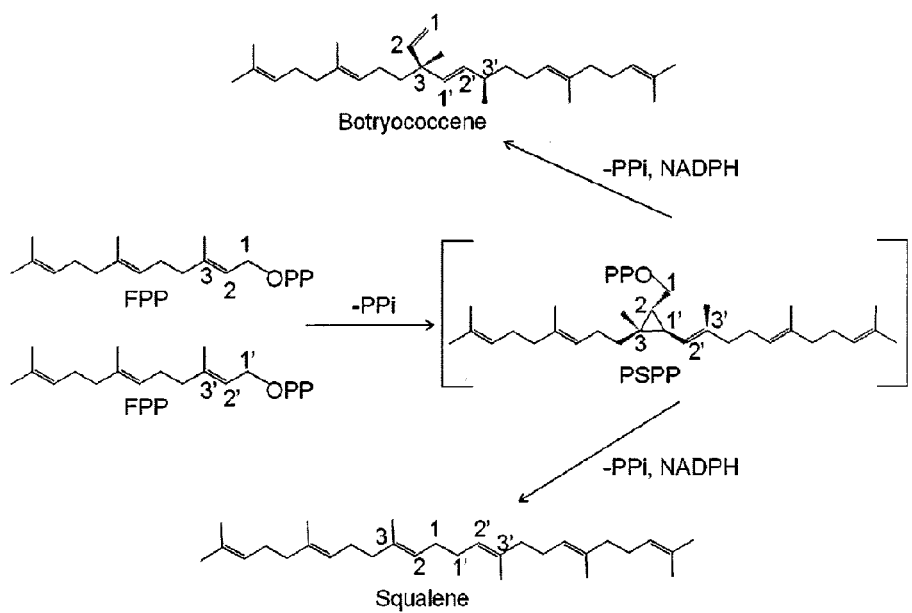

Figure 37. GC-MS of authentic squalene.
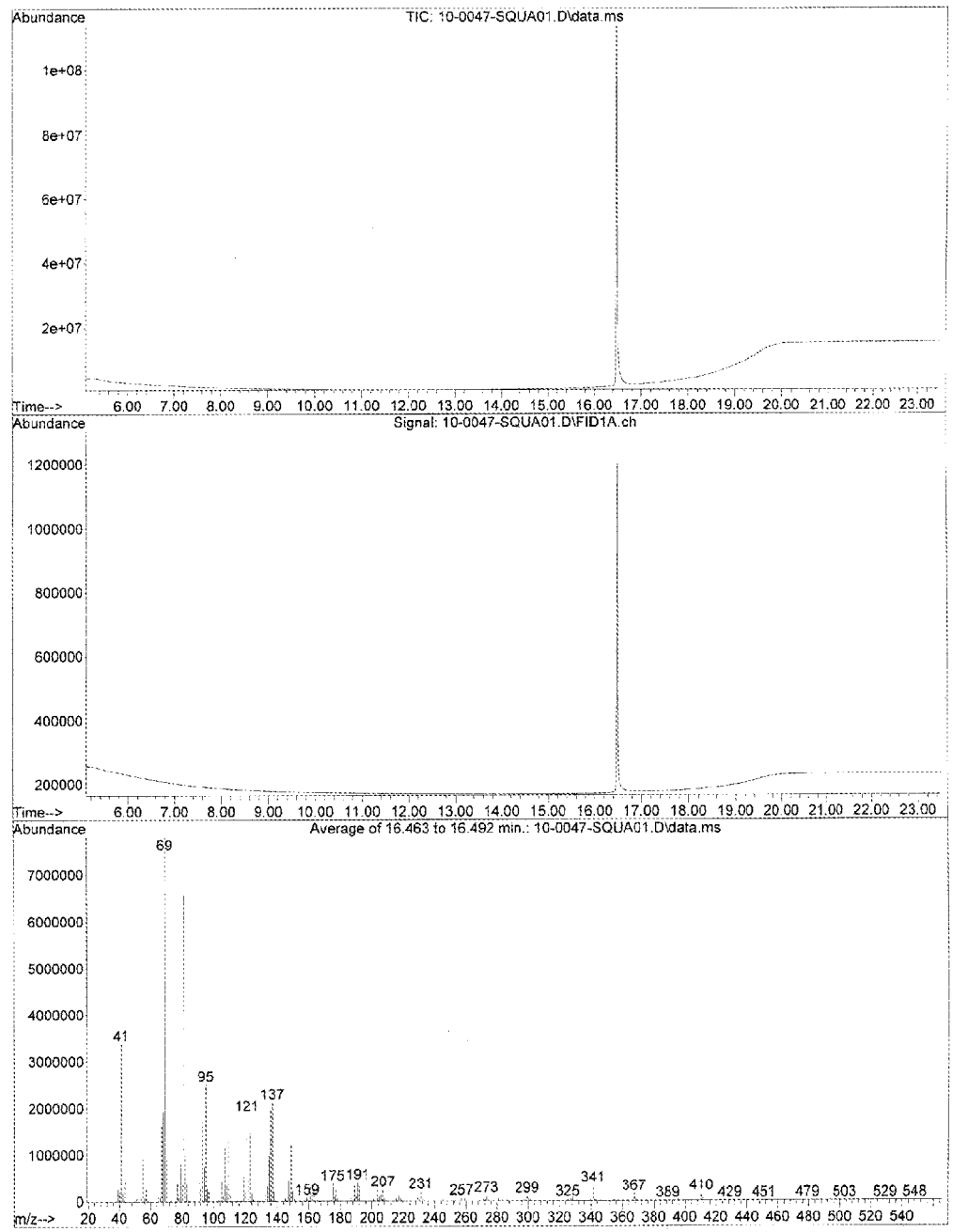

Figure 38. GC-MS of authentic C30 botryococcene.
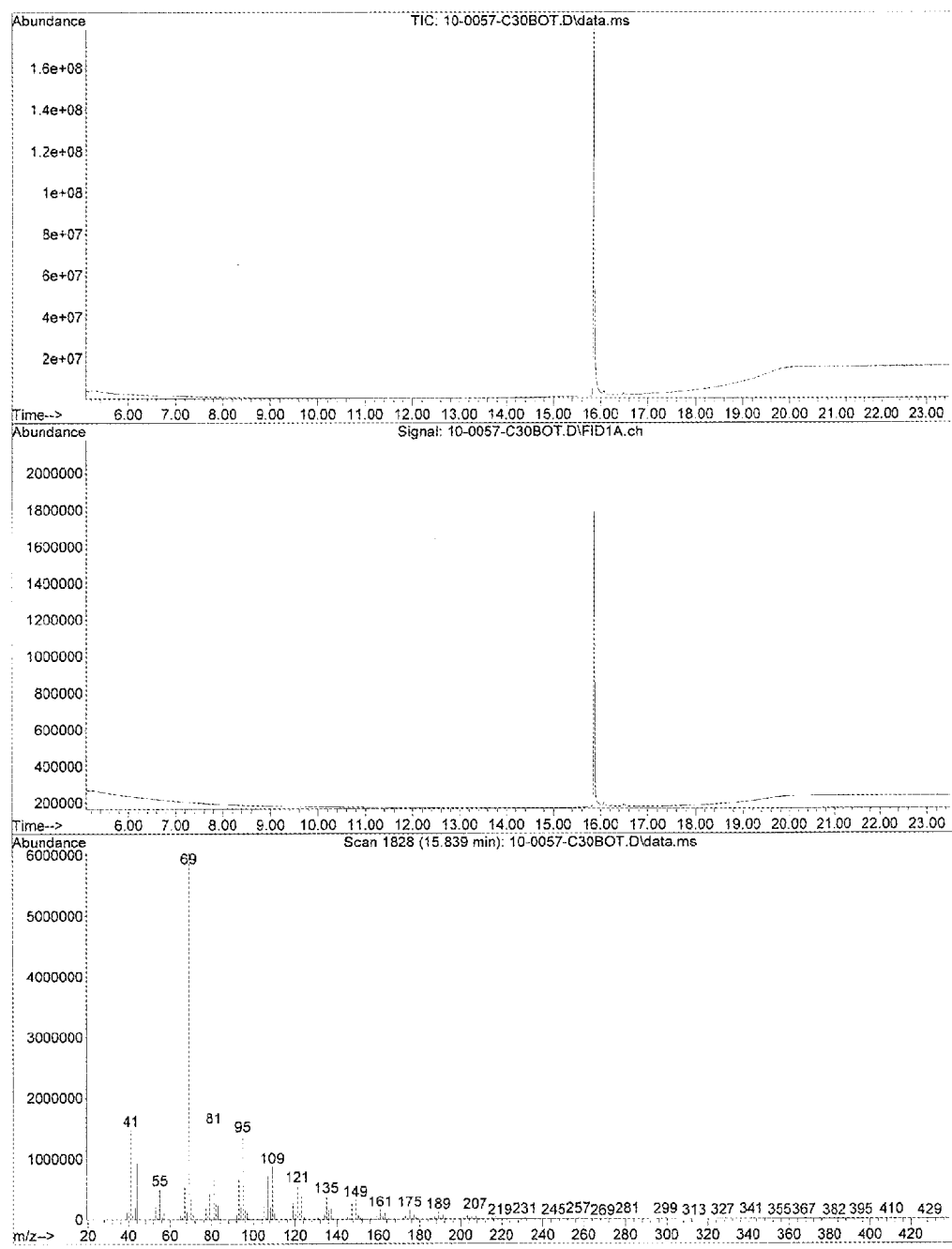

Figure 39. GC-MS of untransformed E. coli induced with IPTG for 16 h.
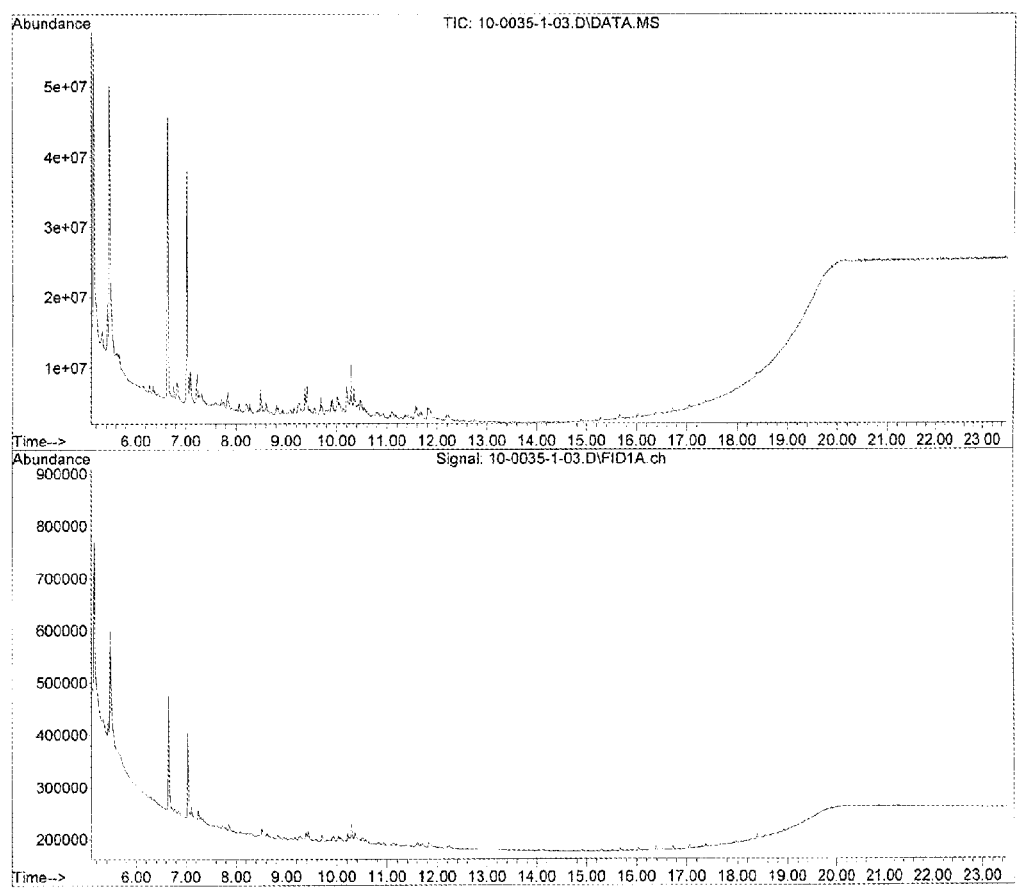

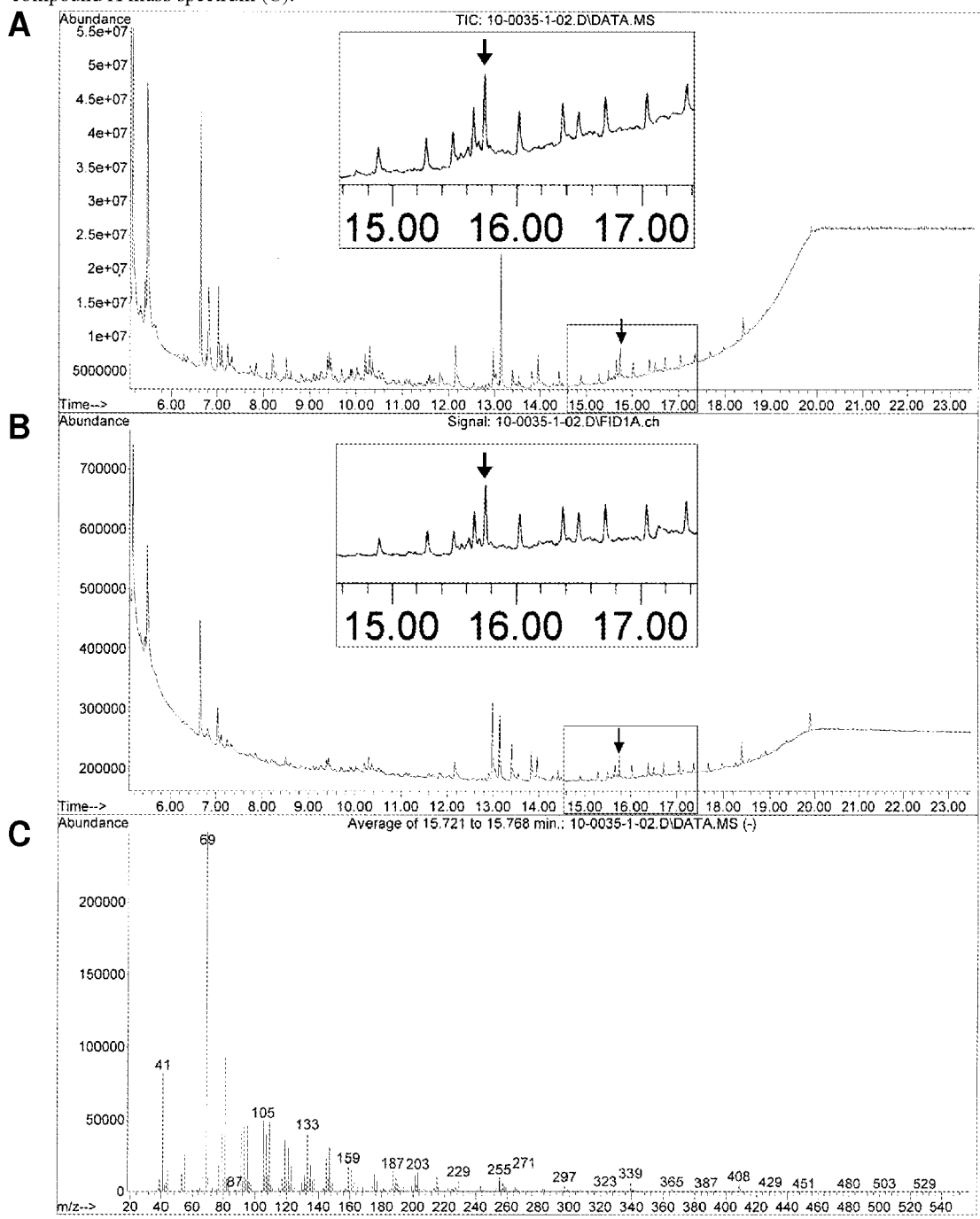
Figure 40. GC-MS E. Coli transformed with pET11a/ATB1 (construct 2) and induced with IPTG for 16 h, compiound X elution profile(A-log, B-Linear), compound X mass spectrum (C).

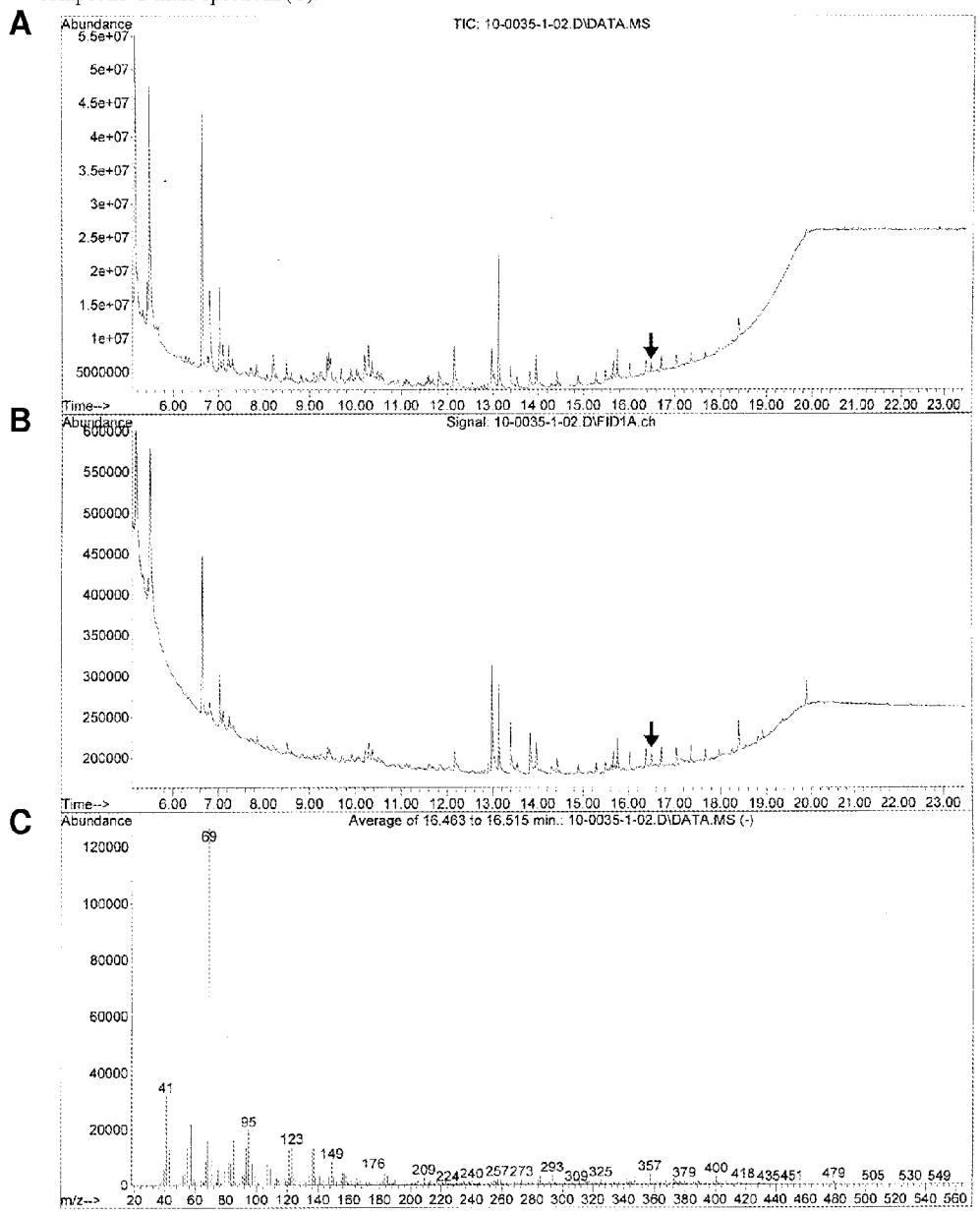
Figure 41. GC-MS E. coli, transformed with pET11a/ATB1 (construct 2) and induced with IPTG for 16 h, compound Y elution profile (A-log, B-linear), compound Y mass spectrum (C).

Figure 42. GC-MS of lysates, derived from E. coli transformed with CT-His-ATB1/pET302 (construct 4), grown to log phase and subsequently induced with IPTG for 2 h, then lysed and the lysate incubated for 30 min with an excess both of FPP and NADPH, before heptane extraction.
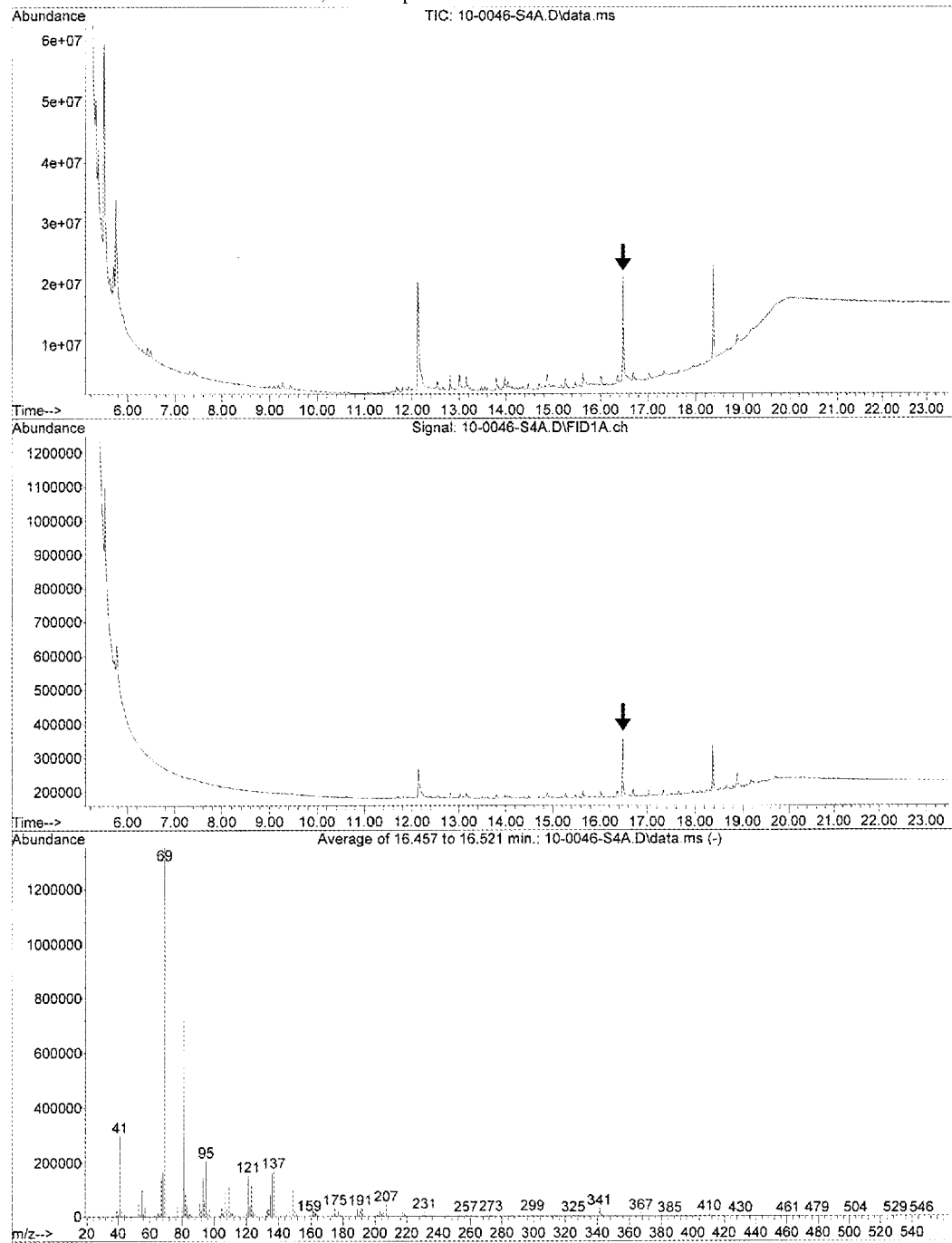

Figure 43 (SEQ ID NO: 33).

CACCACATGCAT

Figure 44 (SEQ ID NO: 34).

ATGCAT

Figure 45 (SEQ ID NO: 35).

CATATG

Figure 46 (SEQ ID NO: 36; ATB1-MH polypeptide sequence).

MSMHQDKGVAKDLLRHPGEFPYLLQLAATTYGTPAAPIPKEPDRAFCYNTLHAVSKGFPR
FVHRLPLELQDPICIFYLLLRALDTVEDDMNLPSKVKVDLLREFHEHCKDRNWSMKSDYG
IYADLMERFPLVISVLEKLPKPTQEVFVENVKYMGNGMADFIDKEILTVDEYDLYCHYVA
GSCGIAVVKVIVQFNLATPEADSMEFSNSLGLLLQKANIITDYNEDINEEPRPRMFWPQE
IWANYSEKLADFNEPANLEKAMKCLNHMVTDALRHIEPSLKGMVYFTDGTVFRALALLLV
TAFGHLSTLYNNPNVFREKVRQRKGRIARLVMSSRNVPGLFRTCLKLAKNFEARCLE
ETKNDPSVATTIKRLQSIQATCREGLEKYETPSGLRALCAAPSPTKMH*

Figure 47 (SEQ ID NO: 37).

TCACTCGAGCCCGGG

Figure 48 (SEQ ID NO: 38; MHHHHHHHHMH-ATB1-MH polypeptide sequence).

MHHHHHHHHMHMSMHQDKGVAKDLLRHPGEFPYLLQLAATTYGTPAAPIPKEPDRAFCYN
TLHAVSKGFPRFVHRLPLELQDPICIFYLLLRALDTVEDDMNLPSKVKVDLLREFHEHCK
DRNWSMKSDYGIYADLMERFPLVISVLEKLPKPTQEVFVENVKYMGNGMADFIDKEILTV
DEYDLYCHYVAGSCGIAVVKVIVQFNLATPEADSMEFSNSLGLLLQKANIITDYNEDINE
EPRPRMFWPQEIWANYSEKLADFNEPANLEKAMKCLNHMVTDALRHIEPSLKGMVYFTDG
TVFRALALLLVTAFGHLSTLYNNPNVFREKVRQRKGRIARLVMSSRNVPGLFRTCLKLAK
NFEARCLEETKNDPSVATTIKRLQSIQATCREGLEKYETPSGLRALCAAPSPTKMH*

Figure 49 (SEQ ID NO: 39; MH-ATB1-MH-HHHHHVNSLEIDDIRA polypeptide sequence).

MHMSMHQDKGVAKDLLRHPGEFPYLLQLAATTYGTPAAPIPKEPDRAFCYNTLHAVSKGF
PRFVHRLPLELQDPICIFYLLLRALDTVEDDMNLPSKVKVDLLREFHEHCKDRNWSMKSD
YGIYADLMERFPLVISVLEKLPKPTQEVFVENVKYMGNGMADFIDKEILTVDEYDLYCHY
VAGSCGIAVVKVIVQFNLATPEADSMEFSNSLGLLLQKANIITDYNEDINEEPRPRMFWP
QEIWANYSEKLADFNEPANLEKAMKCLNHMVTDALRHIEPSLKGMVYFTDGTVFRALALL
LVTAFGHLSTLYNNPNVFREKVRQRKGRIARLVMSSRNVPGLFRTCLKLAKNFEARCLEE
TKNDPSVATTIKRLQSIQATCREGLEKYETPSGLRALCAAPSPTKMHHHHHHVNSLEIDD
IRA*

Figure 50 (SEQ ID NO: 40).

CCANNNNNNTGG

Figure 51 (SEQ ID NO: 41).

CTCGAG

Figure 52 (SEQ ID NO: 42; SEQ ID NO: 2 of US 2010/0041120).

MTMHQDHGVMKDLVKHPNEFPYLLQLAATYGSPAAPIPKEPDRAFCYNTLHTVSKGFPFV
MRLPQELQDPICIFYLLLRALDTVEDDMNLKSETKISLLRVFHEHCSDRNWSMKSDYGIY
ADLMERFPLVVSVLEKLPPATQQTFRENVKYMGNGMADFIDKQILTVDEYDLYCHYVAGS
CGIAVTKVIVQFNLATPEADSYDFSNSLGLLLQKANIITDYNEDINEEPRPRMFWPQEIW
GKYAEKLADFNEPENIDTAVKCLNHMVTDAMRHIEPSLKGMVYFTDKTVFRALALLLVTA
FGHLSTLYNNPNVFKEKVRQRKGRIARLVMSSRNVPGLFRTCLKLANNFESRCKQETAND
PTVAMTIKRLQSIQATCRDGLAKYDTPSGLKSFCAAPTPTK

Figure 53.

```
SEQIDNC29    MSMHQDKGVAKDLLRHPGEFPYLLQLAATTYGTPAAPIPKEPDRAFCYNTLHAVSKGFPR  60
SEQIDNC42    MTMHQDHGVMKDLVKHPNEFPYLLQLAAT-YGSPAAPIPKEPDRAFCYNTLHTVSKGFP-  58
SEQIDNC12    MGMLR-WGVES--LQNPDELIPVLRMIYA--DKFGKIKPKDEDRGFCYEILNLVSRSFAI  55
              * *  :   **  .    :::*.*:  :*::  :  ... .   **: **.***: *: **:.*.

SEQIDNC29    FVHRLPLELQDPICIFYLLLRALDTVEDDMNLPSKVKVDLLREFHEHCKDRNWSMKS-DY 119
SEQIDNC42    FVMRLPQELQDPICIFYLLLRALDTVEDDMNLKSETKISLLRVFHEHCSDRNWSMKS-DY 117
SEQIDNC12    VIQQLPAQLRDPVCIFYLVLRALDTVEDDMKIAATTKEPLLRDFYEKISDRSFRMTAGDQ 115
              .: :** :*:**:*****:********** :     :  .*:  *** *:*: .**.: *.: *
                  I                II

SEQIDNC29    GIYADLMERFPLVISVLEKLPKPTQEVFVENVKYMGNGMADFIDKEIL-TVDEYDLYCHY 178
SEQIDNC42    GIYADLMERFPLVVSVLEKLPPATQQTFRENVKYMGNGMADFIDKQIL-TVDEYDLYCHY 176
SEQIDNC12    KDYIRLLDQYPKVTSVFLKLTPREQEIIADITKRMGNGMADFVHKGVPDTVGDYDLYCHY 175
              * *::::*  *  ** :**. . *:  :  . * ********:.* :  **.:******
                                                                       III

SEQIDNC29    VAGSCGIAVVKVIVQFNLATPEAD-SMEFSNSLGLLLQKANIITDYNEDINEEPRPRMFW 237
SEQIDNC42    VAGSCGIAVTKVIVQFNLATPEAD-SYDFSNSLGLLLQKANIITDYNEDINEEPRPRMFW 235
SEQIDNC12    VAGVVGLGLSQLFVASGLQSPSLTRSEDLSNHMGLFLQKTNIIRDYFEDINELPAPRMFW 235
              ***  *:.. :::*  .*  :*.    *  ::**  **:***:*** ** ****  * *****
                   III                                IV

SEQIDNC29    PQEIWANYSEKLADFNEPANLEKAMKCLNHMVTDALRHIEPSLKGMVYFTDGTVFRALAL 297
SEQIDNC42    PQEIWGKYAEKLADFNEPENIDTAVKCLNHMVTDAMRHIEPSLKGMVYFTDKTVFRALAL 295
SEQIDNC12    PREIWGKYANNLAEFKDPANKAAAMCCLNEMVTDALRHAVYCLQYMSMIEDPQIFNFCAI 295
              *:***.:*:::**:*:*:* *  *: ***.*****.:*  :  * :* .*:*  *:
                                                                        V

SEQIDNC29    LLVTAFGHLSTLYNNPNVFR---EKVRQRKGRIARLVMSSRNVPGLFRTCLKLAKNFEAR 354
SEQIDNC42    LLVTAFGHLSTLYNNPNVFK---EKVRQRKGRIARLVMSSRNVPGLFRTCLKLANNFESR 352
SEQIDNC12    PQTMAFGTLSLCYNNYIFTGPKAAVKLRRGTTAKLMYISNNMFAMYRHFLNFAEKLEVR  355
              . ***.**  ***  .:*       *: *:* *:*: :*. .* .:*   *:::*::::*  *
                 V

SEQIDNC29    CLEETKNDPSVATTIKRLQSIQATCREGLE--KYETPSCLRALCAAPS------------ 400
SEQIDNC42    CKQETANDPTVAMTIKRLQSIQATCRDGLA--KYDTPSGLKSFCAAPT------------ 398
SEQIDNC12    CNTETSEDPSVTTTLEHLHKIKAACKAGLARTKDDTFDELRSLLALTGGSFYLAWTYNF  415
              *   ** :**:*: *:::*  .*:*:*: ** . * * . *::    * :

SEQIDNC29    ---------------------------------PTK--------- 403
SEQIDNC42    ---------------------------------PTK--------- 401
SEQIDNC12    LDLRGPGDLPTFLSVIQHWWSILIFLISIAVFFIPSRPSPRPTLSA 461
                                              *::
```

Figure 54. Expression construct pCE3-ATB1 that us used for transformation
of Chlamydomonas reinhardtii strain CC503 to obtain transgenic alga for
triterpenoid production (SEQ ID NO: 43).

GCACTTTTCGGGGAAATGTGCGCGGAACCCCTATTTGTTTATTTTTCTAAATACATTCAAATATGTATCCGCTCA
TGAGACAATAACCCTGATAAATGCTTCAATAATATTGAAAAAGGAAGAGTATGAGTATTCAACATTTCCGTGTCG
CCCTTATTCCCTTTTTTGCGGCATTTTGCCTTCCTGTTTTTGCTCACCCAGAAACGCTGGTGAAAGTAAAAGATG
CTGAAGATCAGTTGGGTGCACGAGTGGGTTACATCGAACTGGATCTCAACAGCGGTAAGATCCTTGAGAGTTTTC
GCCCCGAAGAACGTTTTCCAATGATGAGCACTTTTAAAGTTCTGCTATGTGGCGCGGTATTATCCCGTATTGACG
CCGGGCAAGAGCAACTCGGTCGCCGCATACACTATTCTCAGAATGACTTGGTTGAGTACTCACCAGTCACAGAAA
AGCATCTTACGGATGGCATGACAGTAAGAGAATTATGCAGTGCTGCCATAACCATGAGTGATAACACTGCGGCCA
ACTTACTTCTGACAACGATCGGAGGACCGAAGGAGCTAACCGCTTTTTTGCACAACATGGGGGATCATGTAACTC
GCCTTGATCGTTGGGAACCGGAGCTGAATGAAGCCATACCAAACGACGAGCGTGACACCACGATGCCTGTAGCAA
TGGCAACAACGTTGCGCAAACTATTAACTGGCGAACTACTTACTCTAGCTTCCCGGCAACAATTAATAGACTGGA
TGGAGGCGGATAAAGTTGCAGGACCACTTCTGCGCTCGGCCCTTCCGGCTGGCTGGTTTATTGCTGATAAATCTG
GAGCCGGTGAGCGTGGGTCTCGCGGTATCATTGCAGCACTGGGGCAGATGGTAAGCCCTCCCGTATCGTAGTTA
TCTACACGACGGGGAGTCAGGCAACTATGGATGAACGAAATAGACAGATCGCTGAGATAGGTGCCTCACTGATTA
AGCATTGGTAACTGTCAGACCAAGTTTACTCATATATACTTTAGATTGATTTAAAACTTCATTTTTAATTTAAAA
GGATCTAGGTGAAGATCCTTTTTGATAATCTCATGACCAAAATCCCTTAACGTGAGTTTTCGTTCCACTGAGCGT
CAGACCCCGTAGAAAAGATCAAAGGATCTTCTTGAGATCCTTTTTTTCTGCGCGTAATCTGCTGCTTGCAAACAA
AAAAACCACCGCTACCAGCGGTGGTTTGTTTGCCGGATCAAGAGCTACCAACTCTTTTTCCGAAGGTAACTGGCT
TCAGCAGAGCGCAGATACCAAATACTGTCCTTCTAGTGTAGCCGTAGTTAGGCCACCACTTCAAGAACTCTGTAG
CACCGCCTACATACCTCGCTCTGCTAATCCTGTTACCAGTGGCTGCTGCCAGTGGCGATAAGTCGTGTCTTACCG
GGTTGGACTCAAGACGATAGTTACCGGATAAGGCGCAGCGGTCGGGCTGAACGGGGGGTTCGTGCACACAGCCCA
GCTTGGAGCGAACGACCTACACCGAACTGAGATACCTACAGCGTGAGCTATGAGAAAGCGCCACGCTTCCCGAAG
GGAGAAAGGCGGACAGGTATCCGGTAAGCGGCAGGGTCGGAACAGGAGAGCGCACGAGGGAGCTTCCAGGGGGAA
ACGCCTGGTATCTTTATAGTCCTGTCGGGTTTCGCCACCTCTGACTTGAGCGTCGATTTTTGTGATGCTCGTCAG
GGGGGCGGAGCCTATGGAAAAACGCCAGCAACGCGGCCTTTTTACGGTTCCTGGCCTTTTGCTGGCCTTTTGCTC
ACATGTTCTTTCCTGCGTTATCCCCTGATTCTGTGGATAACCGTATTACCGCCTTTGAGTGAGCTGATACCGCTC
GCCGCAGCCGAACGACCGAGCGCAGCGAGTCAGTGAGCGAGGAAGCGGAAGAGCGCCCAATACGCAAACCGCCTC
TCCCCGCGCGTTGGCCGATTCATTAATGCAGCTGGCACGACAGGTTTCCCGACTGGAAAGCGGGCAGTGAGCGCA
ACGCAATTAATGTGAGTTAGCTCACTCATTAGGCACCCCAGGCTTTACACTTTATGCTTCCGGCTCGTATGTTGT
GTGGAATTGTGAGCGGATAACAATTTCACACAGGAAACAGCTATGACCATGATTACGCCAAGCTCGAAATTAACC
CTCACTAAAGGGAACAAAAGCTGGAGCTCTAAATGCCAGAAGGAGCGCAGCCAAACCAGGATGATGTTTGATGGG
GTATTTGAGCACTTGCAACCCTTATCCGGAAGCCCCCTGGCCCACAAAGGCTAGGCGCCAATGCAAGCAGTTCGC
ATGCAGCCCCTGGAGCGGTGCCCTCCTGATAAACCGGCCAGGGGGCCTATGTTCTTTACTTTTTTACAAGAGAAG
TCACTCAACATCTTAAAGCGGCCGCAAAATGAGTATGCACCAAGACAAGGGGGTTGCTAAGGATCTTTAAGGCA
TCCAGGGGAATTCCCCTATTTGCTCCAGCTAGCCGCTACAACTTACGGCACACCGGCGGCCCCGATCCCAAAGGA
ACCCGACCGAGCGTTCTGCTATAACACTCTTCACGCTGTTTCTAAAGGGTTCCCGAGGTTTGTTCACAGGCTTCC
TCTGGAACTCCAGGATCCAATCTGCATTTTTTATCTCCTGCTGCGTGCACTAGATACAGTGGAGGATGATATGAA
CCTCCCAAGTAAGGTGAAGGTAGATCTGTTGCGCGAGTTTCATGAGCATTGTAAAGACAGGAACTGGAGCATGAA
AAGTGATTATGGCATCTATGCAGACTTGATGGAAAGGTTTCCTCTGGTGATTTCCGTCCTGGAAAAGCTTCCTAA
GCCCACACAGGAGGTTTTTGTGGAGAATGTCAAATATATGGGCAATGGCATGGCAGACTTTATTGATAAGGAGAT
CTTGACTGTGGATGAGTACGATCTGTACTGCCACTATGTGGCTGGTAGTTGTGGCATTGCTGTTGTCAAGGTTAT
TGTCCAATTTAACCTTGCCACGCCGGAAGCTGACTCGATGGAGTTTTCCAACAGCCTAGGATTGTTGCTTCAGAA
AGCCAACATCATTACTGACTACAATGAGGACATTAACGAAGAACCCAGACCCCGGATGTTCTGGCCCCAAGAGAT
CTGGGCCAATTACTCGGAAAAGTTAGCTGACTTTAATGAACCCGCCAACCTTGAAAAAGCTATGAAGTGCTTGAA
CCACATGGTCACAGATGCCCTGCGCCACATTGAGCCATCTCTTAAGGGCATGGTTTATTTCACAGACGGGACAGT
CTTCCGCGCTCTTGCTCTTCTGCTGGTCACAGCTTTTGGTCACTTGTCGACTTTGTACAATAACCCAAATGTTTT
CCGAGAGAAGGTGAGGCAGCGGAAGGGAAGGATTGCCCGGCTAGTGATGTCATCCAGAAACGTACCAGGCCTCTT
CCGCACCTGCCTAAAACTTGCAAAGAACTTTGAAGCCAGGTGTCTGGAGGAGACAAAGAATGATCCCTCTGTGGC
CACAACCATCAAGCGGCTGCAGTCAATCCAGGCCACGTGCAGAGAAGGCCTGGAAAAAATATGAGACACCATCTGG
GCTGAGGGCGCTCTGTGCTGCTCCAAGCCCTACAAAGTGACGCGGCCGCCCCGCTCCGTGTAAATGGAGGCGCTC
GTTGATCTGAGCCTTGCCCCCTGACGAACGGCGGTGGATGGAAGATACTGCTCTCAAGTGCTGAAGCGGTAGCTT
AGCTCCCCGTTTCGTGCTGATCAGTCTTTTTCAACACGTAAAAAGCGGAGGAGTTTTGCAATTTTGTTGGTTGTA
ACGATCCTCCGTTGATTTTGGCCTCTTTCTCCATGGGCGGGCTGGGCGTATTTGAAGCGAATTCGATATCAAGCT
TATCGATACCGTCGACCTCGAGATTTAAATGCCAGAAGGAGCGCAGCCAAACCAGGATGATGTTTGATGGGTAT
TTGAGCACTTGCAACCCTTATCCGGAAGCCCCCTGGCCCACAAAGGCTAGGCGCCAATGCAAGCAGTTCGCATGC
AGCCCCTGGAGCGGTGCCCTCCTGATAAACCGGCCAGGGGGCCTATGTTCTTTACTTTTTTACAAGAGAAGTCAC
TCAACATCTTAAAATGGCCAGGTGAGTCGACGAGCAAGCCCGGCGGATCAGGCAGCGTGCTTGCAGATTTGACTT

Figure 54. continued

```
GCAACGCCCGCATTGTGTCGACGAAGGCTTTTGGCTCCTCTGTCGCTGTCTCAAGCAGCATCTAACCCTGCGTCG
CCGTTTCCATTTGCAGGATGGCCAAGCTGACCAGCGCCGTTCCGGTGCTCACCGCGCGCGACGTCGCCGGAGCGG
TCGAGTTCTGGACCGACCGGCTCGGGTTCTCCCGGGACTTCGTGGAGGACGACTTCGCCGGTGTGGTCCGGGACG
ACGTGACCCTGTTCATCAGCGCGGTCCAGGACCAGGTGAGTCGACGAGCAAGCCCGGCGGATCAGGCAGCGTGCT
TGCAGATTTGACTTGCAACGCCCGCATTGTGTCGACGAAGGCTTTTGGCTCCTCTGTCGCTGTCTCAAGCAGCAT
CTAACCCTGCGTCGCCGTTTCCATTTGCAGGACCAGGTGGTGCCGGACAACACCCTGGCCTGGGTGTGGGTGCGC
GGCCTGGACGAGCTGTACGCCGAGTGGTCGGAGGTCGTGTCCACGAACTTCCGGGACGCCTCCGGGCCGGCCATG
ACCGAGATCGGCGAGCAGCCGTGGGGCGGGAGTTCGCCCTGCGCGACCCGGCCGGCAACTGCGTGCACTTCGTG
GCCGAGGAGCAGGACTAACCGACGTCGACCCACTCTAGAGGATCGATCCCCGCTCCGTGTAAATGGAGGCGCTCG
TTGATCTGAGCCTTGCCCCCTGACGAACGGCGGTGGATGGAAGATACTGCTCTCAAGTGCTGAAGCGGTAGCTTA
GCTCCCCGTTTCGTGCTGATCAGTCTTTTTCAACACGTAAAAAGCGGAGGAGTTTTGCAATTTTGTTGGTTGTAA
CGATCCTCCGTTGATTTTGGCCTCTTTCTCCATGGGCGGGCTGGGCGTATTTGAAGCTTAATTAACTCGAGGGGG
GGCCCGGTACCCAATTCGCCCTATAGTGAGTCGTATTACAATTCACTGGCCGTCGTTTTACAACGTCGTGACTGG
GAAAACCCTGGCGTTACCCAACTTAATCGCCTTGCAGCACATCCCCCTTTCGCCAGCTGGCGTAATAGCGAAGAG
GCCCGCACCGATCGCCCTTCCCAACAGTTGCGCAGCCTGAATGGCGAATGGAAATTGTAAGCGTTAATATTTTGT
TAAAATTCGCGTTAAATTTTGTTAAATCAGCTCATTTTTTAACCAATAGGCCGAAATCGGCAAAATCCCTTATA
AATCAAAAGAATAGACCGAGATAGGGTTGAGTGTTGTTCCAGTTTGGAACAAGAGTCCACTATTAAAGAACGTGG
ACTCCAACGTCAAAGGGCGAAAAACCGTCTATCAGGGCGATGGCCCACTACGTGAACCATCACCCTAATCAAGTT
TTTTGGGGTCGAGGTGCCGTAAAGCACTAAATCGGAACCCTAAAGGGAGCCCCCGATTTAGAGCTTGACGGGGAA
AGCCGGCGAACGTGGCGAGAAAGGAAGGGAAGAAAGCGAAAGGAGCGGGCGCTAGGGCGCTGGCAAGTGTAGCGG
TCACGCTGCGCGTAACCACCACACCCGCCGCGCTTAATGCGCCGCTACAGGGCGCGTCAGGTG
```

Broken underline = *SacI, NotI* or *EcoRI* restriction sites
Dashed underline = promoter that was inserted (5', 2210-2417) and terminator that was inserted (3', 3653-3883)
Bold underline = start (ATG) and stop (TGA) codons of *ATB1* gene (2429-3640)
Double underline = promoter (5', 3931-4138) and terminator (3', 4852-5082) of *ble* gene
*ble* gene = 4139-4818 (bold = exons, *italic* = introns)

Figure 55. Primer RbcS2-termforw, which contains a *NotI* restriction site (SEQ ID NO: 44).

GAGTACGCGGCCGCCCCGCTCCGTGTAAAT

Figure 56. Primer RbcS2-termrev, which contains an *EcoRI* restriction site (SEQ ID NO: 45).

GCACTCGAATTCGCTTCAAATACGCCCAGC

Figure 57. Primer pSP124S-preSacI (SEQ ID NO: 46).

CACTAAAGGGAACAAAAGCTG

Figure 58. T3 primer (SEQ ID NO: 47).

GCAATTAACCCTCACTAAAGGGA

Figure 59. Primer RbcS2-promforw, which contains a *SacI* restriction site (SEQ ID NO: 48).

GAGTGCGAGCTCTAAATGCCAGAAGGAGCG

Figure 60. Primer RbcS2-promrev, which contains a *NotI* restriction site (SEQ ID NO: 49).

GTCACTGCGGCCGCTTTAAGATGTTGA

Figure 61. Primer ATB1forw, that contains a *NotI* restriction site (SEQ ID NO: 50).

GTCACTGCGGCCGCGTCACTTTGTAGGGCT

Figure 62. Primer ATB1rev (SEQ ID NO: 51).

GAGTACGCGGCCGCAAAATGAGTATGCACC

SEQUENCE LISTING

```
<160> NUMBER OF SEQ ID NOS: 51

<210> SEQ ID NO 1
<211> LENGTH: 56
<212> TYPE: PRT
<213> ORGANISM: Botryococcus braunii

<400> SEQUENCE: 1

Gln Val Pro Glu Val Val His Arg Leu Pro Leu Glu Leu Gln Asp Pro
1               5                   10                  15
```

```
Ile Cys Ile Phe Tyr Leu Leu Arg Ala Leu Asp Thr Val Glu Asp
            20                  25                  30

Asp Met Asn Leu Pro Ser Lys Val Lys Val Asp Leu Leu Arg Glu Phe
            35                  40                  45

His Glu His Cys Lys Asp Arg Cys
 50                  55
```

<210> SEQ ID NO 2
<211> LENGTH: 43
<212> TYPE: PRT
<213> ORGANISM: Botryococcus braunii

<400> SEQUENCE: 2

```
Glu Gln Val Phe Val Glu Asn Val Lys Tyr Met Gly Asn Gly Met Ala
1               5                   10                  15

Asp Phe Ile Asp Lys Glu Ile Leu Thr Val Asp Glu Tyr Asp Leu Tyr
            20                  25                  30

Cys His Tyr Val Ala Gly Ser Cys Gly Ile Ala
            35                  40
```

<210> SEQ ID NO 3
<211> LENGTH: 42
<212> TYPE: PRT
<213> ORGANISM: Botryococcus braunii

<400> SEQUENCE: 3

```
Gln Phe Asn Leu Ala Thr Pro Glu Ala Asp Ser Met Glu Phe Ser Asn
1               5                   10                  15

Ser Leu Gly Leu Leu Leu Gln Lys Ala Asn Ile Ile Thr Asp Tyr Asn
            20                  25                  30

Glu Asp Ile Asn Glu Glu Pro Arg Pro Arg
            35                  40
```

<210> SEQ ID NO 4
<211> LENGTH: 49
<212> TYPE: PRT
<213> ORGANISM: Botryococcus braunii

<400> SEQUENCE: 4

```
Met Phe Trp Pro Gln Glu Ile Trp Ala Asn Tyr Ser Glu Lys Leu Ala
1               5                   10                  15

Asp Phe Asn Glu Pro Ala Asn Leu Glu Lys Ala Met Lys Cys Leu Asn
            20                  25                  30

His Met Val Thr Asp Ala Leu Arg His Ile Glu Pro Ser Leu Lys Gly
            35                  40                  45

Ile
```

<210> SEQ ID NO 5
<211> LENGTH: 29
<212> TYPE: PRT
<213> ORGANISM: Botryococcus braunii

<400> SEQUENCE: 5

```
Arg Cys Leu Glu Glu Thr Lys Asn Asp Pro Ser Val Ala Thr Thr Ile
1               5                   10                  15

Lys Arg Leu Gln Ser Ile Gln Ala Thr Cys Arg Glu Gly
            20                  25
```

<210> SEQ ID NO 6
<211> LENGTH: 378
<212> TYPE: DNA

<213> ORGANISM: Botryococcus braunii

<400> SEQUENCE: 6

| | |
|---|---|
| gtggctgtcc ctacctgatg ggtttctctg tgtctgcagg ttcccgaggt ttgttcacag | 60 |
| gcttcctctg gaactccagg atccaatctg catttttat ctcctgctgc gtgcactaga | 120 |
| tacagtggag gatgatatga acctcccaag taaggtgaag gtagatctgt tgcgcgagtt | 180 |
| tcatgagcat tgtaaagaca ggtgcgtccc ttgttctcat ggaactagat aacagcaaat | 240 |
| gcacatattc tacagaggag tgttttctg tgtgtctgtg ttactgcgct gacacgcact | 300 |
| tgaccccctcc ccgttcttcg ctccagtttg cttccctctt ttccgcttct tctgcttctg | 360 |
| accctaccta acactcca | 378 |

<210> SEQ ID NO 7
<211> LENGTH: 1168
<212> TYPE: DNA
<213> ORGANISM: Botryococcus braunii

<400> SEQUENCE: 7

| | |
|---|---|
| gtatctgcct acagtttcta ctccatttcg agatgtgcta agttcacaaa cgagttcctt | 60 |
| gtatgcagga actggagcat gaaaagtgat tatggcatct atgcagactt gatggaaagg | 120 |
| tttcctctgg tgatttccgt cctggaaaag cttcctaagc ccacacagga ggtaggaaag | 180 |
| aagctgtagc ccaagctttt tgagcgagct tatctgagtg ctcgaacggg tactcagctt | 240 |
| gggtccttcc tacatgtggc tggcgagaac actaacagtt gcaatgaaga gttcttcagg | 300 |
| aggattgctg gctgccatgt cttgttttgt tgtccagagg agttttcagc tacgtttgaa | 360 |
| atgctactgt tgtacctaaa gtggagaatg tagggaaagt cagttgtcgt ccccctcttt | 420 |
| tttctgtttg agttgtgttc ccattattca atagcatttc ctgatggttg tatggtggat | 480 |
| gtcttgcatc ccagatacaa atacaagcca atttttgcagg agagcactcc tgaagatggt | 540 |
| gtccttccac tgttgtcacg gacgaggggt gctgaatgtt gtgggcacaa acagcagtgc | 600 |
| atcccataca tggaatgttg ttgtctacac gttgacacgt tccaagcatc actagctgcc | 660 |
| ctcctgatac tcttctcggt catctaagct cacgcatccg aacatggcac tttacaaaaa | 720 |
| gaaacagtgt tttttgacgt tgaacaggtt tttgtggaga atgtcaaata tatgggcaat | 780 |
| ggcatggcag actttattga taaggagatc ttgactgtgg atgagtacga tctgtactgc | 840 |
| cactatgtgg ctggtagttg tggcattgct gttgtcaagg kacgtactct ctaacatagt | 900 |
| ctggtacccc cagttttgcc tctgcagatg ttattgcaag tggcttccac gaacaccatg | 960 |
| ggctcctggt gcagtccaac ttgcgaggtc atgggcttga agtcgccctg tctacggaac | 1020 |
| acccgattca tgaccaaggt tacataatat cgttgttcct taattcggaa tactaaagtt | 1080 |
| aaggtttcgg aacgtctacc ctaagcccta gaacaccgcc aattggcctg ggagacattt | 1140 |
| ctagtgtgtt ttctggtctt gcgaggat | 1168 |

<210> SEQ ID NO 8
<211> LENGTH: 578
<212> TYPE: DNA
<213> ORGANISM: Botryococcus braunii
<220> FEATURE:
<221> NAME/KEY: misc_feature
<222> LOCATION: (161)..(161)
<223> OTHER INFORMATION: n is a, c, g, or t

<400> SEQUENCE: 8

| | |
|---|---|
| gttattgtcc aatttaacct tgccacgccg gaagctgact cgatggagtt ttccaacagc | 60 |

-continued

```
ctaggattgt tgcttcagaa agccaacatc attactgact acaatgagga cattaacgaa    120
gaacccagac cccggtatgc cactagcata ttcagagaca ncatggctct gtacacaatc    180
ttactgtaaa aatgactgaa aggagtggct gcaatgtttt gtctgtcaaa cctatcaggg    240
caagtcgact tgaaggtctg gttcgcaata tgggttttgc atggtcacgt ttagagtatg    300
tggtaacgat tgatatctcc tctgaagtgc catttgctgt atgtatggag tggccgtcag    360
aagtcccagg ataagagcaa ctggttattg tcaaaaactt tgactgggta cattgggagt    420
tcctgcagga tgttctggcc ccaagagatc tgggccaatt actcggaaaa gttagctgac    480
tttaatgaac cgccaacct tgaaaaagct atgaagtgct gaaccacat ggtcacagat    540 gccctgcgcc acattgagcc atctcttaag ggcatggg                             578
```

<210> SEQ ID NO 9
<211> LENGTH: 88
<212> TYPE: DNA
<213> ORGANISM: Botryococcus braunii

<400> SEQUENCE: 9

```
aggtgtctgg aggagacaaa gaatgatccc tctgtggcca caaccatcaa gcggctgcag    60
tcaatccagg ccacgtgcag agaaggcc                                        88
```

<210> SEQ ID NO 10
<211> LENGTH: 461
<212> TYPE: PRT
<213> ORGANISM: Botryococcus braunii

<400> SEQUENCE: 10

Met Gly Met Leu Arg Trp Gly Val Glu Ser Leu Gln Asn Pro Asp Glu
1               5                   10                  15

Leu Ile Pro Val Leu Arg Met Ile Tyr Ala Asp Lys Phe Gly Lys Ile
            20                  25                  30

Lys Pro Lys Asp Glu Asp Arg Gly Phe Cys Tyr Glu Ile Leu Asn Leu
        35                  40                  45

Val Ser Arg Ser Phe Ala Ile Val Ile Gln Gln Leu Pro Ala Gln Leu
    50                  55                  60

Arg Asp Pro Val Cys Ile Phe Tyr Leu Val Leu Arg Ala Leu Asp Thr
65                  70                  75                  80

Val Glu Asp Asp Met Lys Ile Ala Ala Thr Thr Lys Ile Pro Leu Leu
                85                  90                  95

Arg Asp Phe Tyr Glu Lys Ile Ser Asp Arg Ser Phe Arg Met Thr Ala
            100                 105                 110

Gly Asp Gln Lys Asp Tyr Ile Arg Leu Leu Asp Gln Tyr Pro Lys Val
        115                 120                 125

Thr Ser Val Phe Leu Lys Leu Thr Pro Arg Glu Gln Glu Ile Ile Ala
    130                 135                 140

Asp Ile Thr Lys Arg Met Gly Asn Gly Met Ala Asp Phe Val His Lys
145                 150                 155                 160

Gly Val Pro Asp Thr Val Gly Asp Tyr Asp Leu Tyr Cys His Tyr Val
                165                 170                 175

Ala Gly Val Val Gly Leu Gly Leu Ser Gln Leu Phe Val Ala Ser Gly
            180                 185                 190

Leu Gln Ser Pro Ser Leu Thr Arg Ser Glu Asp Leu Ser Asn His Met
        195                 200                 205

Gly Leu Phe Leu Gln Lys Thr Asn Ile Ile Arg Asp Tyr Phe Glu Asp
    210                 215                 220

```
Ile Asn Glu Leu Pro Ala Pro Arg Met Phe Trp Pro Arg Glu Ile Trp
225                 230                 235                 240

Gly Lys Tyr Ala Asn Asn Leu Ala Glu Phe Lys Asp Pro Ala Asn Lys
            245                 250                 255

Ala Ala Ala Met Cys Cys Leu Asn Glu Met Val Thr Asp Ala Leu Arg
        260                 265                 270

His Ala Val Tyr Cys Leu Gln Tyr Met Ser Met Ile Glu Asp Pro Gln
    275                 280                 285

Ile Phe Asn Phe Cys Ala Ile Pro Gln Thr Met Ala Phe Gly Thr Leu
290                 295                 300

Ser Leu Cys Tyr Asn Asn Tyr Thr Ile Phe Thr Gly Pro Lys Ala Ala
305                 310                 315                 320

Val Lys Leu Arg Arg Gly Thr Thr Ala Lys Leu Met Tyr Thr Ser Asn
            325                 330                 335

Asn Met Phe Ala Met Tyr Arg His Phe Leu Asn Phe Ala Glu Lys Leu
        340                 345                 350

Glu Val Arg Cys Asn Thr Glu Thr Ser Glu Asp Pro Ser Val Thr Thr
    355                 360                 365

Thr Leu Glu His Leu His Lys Ile Lys Ala Ala Cys Lys Ala Gly Leu
370                 375                 380

Ala Arg Thr Lys Asp Asp Thr Phe Asp Glu Leu Arg Ser Arg Leu Leu
385                 390                 395                 400

Ala Leu Thr Gly Gly Ser Phe Tyr Leu Ala Trp Thr Tyr Asn Phe Leu
            405                 410                 415

Asp Leu Arg Gly Pro Gly Asp Leu Pro Thr Phe Leu Ser Val Thr Gln
        420                 425                 430

His Trp Trp Ser Ile Leu Ile Phe Leu Ile Ser Ile Ala Val Phe Phe
    435                 440                 445

Ile Pro Ser Arg Pro Ser Pro Arg Pro Thr Leu Ser Ala
450                 455                 460

<210> SEQ ID NO 11
<211> LENGTH: 3076
<212> TYPE: DNA
<213> ORGANISM: Botryococcus braunii

<400> SEQUENCE: 11
aacagcaaca agtcctctgc gtcaggcaaa acgtccgttt gtatggcttg gcgcttgaaa      60
gctggtgggg ataaacgtca aaagaaagaa gctctgttcg ggttcacggg tgtcgtttag     120
tactttcccc tacgacattg tcagccttgg ctcatcgcaa tccaaccaaa tatggggatg     180
cttcgctggg gagtggagtc tttgcagaat ccagatgaat taatcccggt cttgaggatg     240
atttatgctg ataagtttgg aaagatcaag ccaaaggacg aagaccgggg cttctgctat     300
gaaattttaa accttgtttc aagaagtttt gcaatcgtca tccaacagct ccctgcacag     360
ctgagggacc cagtctgcat attttacctt gtactacgcg ccctggacac agtcgaagat     420
gatatgaaaa ttgcagcaac caccaagatt cccttgctgc gtgacttttg tgagaaaatt     480
tctgacaggt cattccgcat gacggccgga gatcaaaaag actacatcag gctgttggat     540 cagtaccccca agtgacaag cgttttcttg aaattgaccc cccgtgaaca agagataatt     600
gcagacatta caaagcggat ggggaatgga atggctgact cgtgcataa gggtgttccc     660 gacacagtgg gggactacga cctttactgc cactatgttg ctggggtggt gggtctcggg     720 cttcccagt tgttcgttgc gagtggacta cagtcaccct ctttgacccg cagtgaagac     780 cttttccaatc acatgggcct cttccttcag aagaccaaca tcatccgcga ctactttgag     840
```

```
gacatcaatg agctgcctgc cccccggatg ttctggccca gagagatctg gggcaagtat      900
gcgaacaacc tcgctgagtt caaagacccg gccaacaagg cggctgcaat gtgctgcctc      960
aacgagatgg tcacagatgc attgaggcac gcggtgtact gcctgcagta catgtccatg     1020
attgaggatc cgcagatctt caacttctgt gccatcctc agaccatggc cttcggcacc      1080
ctgtctttgt gttacaacaa ctacactatc ttcacagggc ccaaagcggc tgtgaagctg     1140
cgtagggca ccactgccaa gctgatgtac acctctaaca atatgtttgc gatgtaccgt      1200
catttcctca acttcgcaga gaagctgaaa gtcagatgca acaccgagac cagcgaggat     1260
cccagcgtga ccaccactct ggaacacctg cataagatca aagctgcctg caaggctggg     1320
ctggcacgca caaaagatga cacctttgac gaattgagga gcaggttgtt agcgctgacg     1380
ggaggcagct tctacctcgc ctggacctac aatttcctag accttcgagg cccgggagac     1440
ctgcccacct tcttatctgt aacccaacat tggtggtcta ttctgatctt cctcatttcg     1500
attgccgtct tctttattcc gtcgaggccc tcacctagac ccacactcag cgcctaatcc     1560
tttggctctc gtcaattccg gagtccccca ttgttgtcag cacttgggga atttcgtggt     1620
cttcttgacc acactcttgt ctctggcaga ggtcaaggac actgtcaggg acaagtgagt     1680
attctgaccc cccccccccc cccctctgc tcctttcacc acccctccct atcatctggg      1740
gcaaagcttg ggaatgggcc cgtcccctg ttgtcccgct cagatgcaaa gtttgggtta      1800
tgtaactggg ttgaacggct cggggcggtt tgaagctgtc ccttgttgga gatggaaaat     1860
tgcagggccc gggggggtta actggacacg ctcttccgtc ccgcagtgtc cttctggctt     1920
tattctgccg tggatgctgt gaacccgccc cctctctggg ccggctcaat atacaagtat     1980
tagtttcggt gtttgtgtca atcctttctc acaacttccc tgttcgttgg actggagacg     2040
caccccttagg tcctttgatt gggaatgcgg cccctttggg tctttaggct ctcgggtagt     2100
ctagtttgca attgttgcat gggcgcggct ttgcacagac gcctggacct tcattgagac     2160
acgtttcgga aaactcgaca gttttgaggt aacctgctcg tgggcctcgg tgtgtctgga     2220
ggtgtcaggg gcctgtgctc cctgctggga tgttcccgct ttgctgtaaa aagtcggacg     2280
tttgttatcc tttgcggggg ttcatctttg agtgggccct gcttctctgc ccgtgtgatg     2340
taatggtttg tattggatag gtatgttgcc ttatctcgtg tatggaattc gtatggtact     2400
tgcagtattc aggagacttg agtaacgaca tcgaggacag gtaacaagcg ctccgattat     2460
gtgctctgtt acacccgact tccaaagatt tatgcgaggt cctggggaac gcagatttga     2520
cattggagag ccccaattgg ccgtggcaat ctgtagaatg tcaaaagaga aaacaggaaa     2580
tcaggtttta aagtccgtgc ctatcagcat cctgtgaaag ctgatgcggt tacgggatga     2640
atgtcaggaa tactcgctcc agtattaacg tgcgcagatt ccgactgaag caaatcgatg     2700
aaatttgggg aggtgtcgtt tttagacctt gacaacggcc atgggtcgta ccttttttgca    2760
aagtatatat ttatttgcac taactcatta ggcacgttgg ttttttttgt ccccctcgga     2820
acgccttttt aagatagtta actagtttgg tcagggtatt cgtcagaagc acgaagcaca     2880
gaaggtttct tttgagatgg cggcgattgt tttccacgag agcagagtca atctcacgcg     2940
tactcgagca aacatcgttg gtcaggacat ggtgttgtct cttggccggc cctgtaactt     3000
tgatgccccc aaaaaaaaaa aaaaaaaaaa aaaaaaaaaa aaaaaaaaaa aaaaaaaaaa     3060
aaaaaaaaaa aaaaaa                                                    3076

<210> SEQ ID NO 12
<211> LENGTH: 126
```

<212> TYPE: PRT
<213> ORGANISM: Botryococcus braunii

<400> SEQUENCE: 12

```
Tyr Cys His Tyr Val Ala Gly Val Val Gly Leu Gly Leu Ser Gln Leu
1               5                   10                  15
Phe Val Ala Ser Gly Leu Gln Ser Pro Ser Leu Thr Arg Ser Glu Asp
            20                  25                  30
Leu Ser Asn His Met Gly Leu Phe Leu Gln Lys Thr Asn Ile Ile Arg
        35                  40                  45
Asp Tyr Phe Glu Asp Ile Asn Glu Leu Pro Ala Pro Arg Met Phe Trp
    50                  55                  60
Pro Arg Glu Ile Trp Gly Lys Tyr Ala Asn Asn Leu Ala Glu Phe Lys
65                  70                  75                  80
Asp Pro Ala Asn Lys Ala Ala Ala Met Cys Cys Leu Asn Glu Met Val
                85                  90                  95
Thr Asp Ala Leu Arg His Ala Val Tyr Cys Leu Gln Tyr Met Ser Met
            100                 105                 110
Ile Glu Asp Pro Gln Ile Phe Asn Phe Cys Ala Ile Pro Gln
        115                 120                 125
```

<210> SEQ ID NO 13
<211> LENGTH: 2223
<212> TYPE: DNA
<213> ORGANISM: Botryococcus braunii

<400> SEQUENCE: 13

```
tactgccact acgtcgctgg ggtggtgggt ctcgggcttt cccaggtggg tcttctgtgt      60
gtgcccatgc tgtcataccc tagatgaact cattgaccta acctttgccc acacgcttct     120
tgcacatacg ttaactcgtt gacctaactc gtccgcttgg caaccctaca cttctgcatg     180
aggcgtaacc catgtccgca acagttccaa gaattaagct ctaaagggg atgggcaaag      240
ttgcgtgcaa gtgagaactg ttgcggttgt cggtgccttg cttggccgcc aacgctactt     300
gtagcgacat aaccagcacc cagacccttc tggtgcatac ataaaaattt cgctgcatgt     360
gcctggtcat gcattcttta caatttcttc taagtcatct gcaactccaa atgcaaagga     420
tttttttcaca tcgagcatgg tttggtgggg gccccatcaa gctcctgggg ggctgttgag    480
agggttgtcc agagttcagt ttggtgcggg catgttcaaa ttttggtgtc ccccccccc     540
tccctcttct atgtctgtgt cattttgggg gggggggg gggggggggg catcaagact      600
tgaacatgcc cgcaccaaac tggactctgg acaacactct ggacaaaacc caaagcttga    660
tggggcccac cccacaaaac tatgctcgtg tggaaaaatc ctttgcatgt gcagtattga    720
tgtcttaaaa gaaagaattt tggacatggg ttacgcctca tgcagaagtg tagggttgcc    780
aagcggacga gttaggtcga tgagttaacg tatgtgcaag aagcgtgtgg gcaagggtaa    840
ggtcaatgag ttcatctagg gtaagaaatg tttacatgga aaggcaaacg ctgcagctat    900
ctgacagttt ctgtgtgtaa atgctggctt catgcatttg tggggcgag tcaaaatgat     960
gtgcagtcca cctattggat cccatcacct caatggtact actggataaa ttcatctgca   1020
tactacaccc tagaaagtcg tagagcagga aagacaagag cccatacatt aagtcaagtg   1080
ctctgtaact gaaatgcaag tttctaatct gtttgtcttg gggtgggtgg gtagttgttc   1140
gttgcgagtg gactacagtc accctctttg acccgcagtg aagacctttc caatcacatg   1200
ggcctcttcc ttcagaagac caacatcatc cgcgactact tgaggacat caatgagctg    1260
cctgcccccc ggtgtgcaac ttgcatatgc tctgtattcg tgcgtatgtt gttggtttga   1320
```

```
taatggctat gcaaatgcca ggtcagtaat gttgtggtgt tccgataata gatagtggac    1380
attcggagaa aggagacttt cattagggac tgagtggttc aaataatatg tgggctgcgc    1440
cctgctttct agacggcaca aatagtggat acgtgttatt ttgttgaaat gatggatgca    1500
atgacatatt tgaacgcctg acagctaatg gaaatggggt tcttgacagg gtaggttaca    1560
atgcctccat caaccctcgt aaatgatgta agtacatttt gctctatatt ttgctgacaa    1620
acatgtcatc tttactcttc accccttca tctctgtgtg tgtgtgtgtg tgtgtgtgtg    1680
tgtgtgtgtt ctggggaagt tgggggaggg gggagacact tgtgctctgg gagctaggag    1740
aataggtaga cttgcctttc cacttgaaag gctcttcaac tgcagagtca aacctaccct    1800
gcctgggtgt gagagtgtgc atacaaggac accatgctcg atggataggc ctcgagtgta    1860
ggcaggtacc tcccagaaaa ctgagcttgc cagggaagat gtgtgtgtgt gggggggcgga    1920 ggggtcatag gaatatcact tacaggactg tccaaaaccg ggcgtaaatg ggcatggaac    1980
atgctcatcc aggatcctga gggtaccggt ggggtttgtc ctcgcaggat gttctggccc    2040
agagagatct ggggcaagta tgcgaacaac ctcgctgagt tcaaagaccc ggccaacaag    2100
gcggctgcaa tgtgctgcct caacgagatg gtcacagatg cattgaggca cgcggtgtac    2160
tgcctgcagt acatgtccat gattgaggat ccgcagatct tcaacttctg tgccatccct    2220
cag                                                                  2223
```

<210> SEQ ID NO 14
<211> LENGTH: 461
<212> TYPE: PRT
<213> ORGANISM: Artificial Sequence
<220> FEATURE:
<223> OTHER INFORMATION: Synthetic Construct

<400> SEQUENCE: 14

```
Met Gly Met Leu Arg Trp Gly Val Glu Ser Leu Gln Asn Pro Asp Glu
1               5                   10                  15

Leu Ile Pro Val Leu Arg Met Ile Tyr Ala Asp Lys Phe Gly Lys Ile
            20                  25                  30

Lys Pro Lys Asp Glu Asp Arg Gly Phe Cys Tyr Glu Ile Leu Asn Leu
        35                  40                  45

Val Ser Arg Ser Phe Ala Ile Val Ile Gln Gln Leu Pro Ala Gln Leu
    50                  55                  60

Arg Asp Pro Val Cys Ile Phe Tyr Leu Val Leu Arg Ala Leu Asp Thr
65                  70                  75                  80

Val Glu Asp Asp Met Lys Ile Ala Ala Thr Thr Lys Ile Pro Leu Leu
                85                  90                  95

Arg Asp Phe Tyr Glu Lys Ile Ser Asp Arg Ser Phe Arg Met Thr Ala
            100                 105                 110

Gly Asp Gln Lys Asp Tyr Ile Arg Leu Leu Asp Gln Tyr Pro Lys Val
        115                 120                 125

Thr Ser Val Phe Leu Lys Leu Thr Pro Arg Glu Gln Glu Ile Ile Ala
    130                 135                 140

Asp Ile Thr Lys Arg Met Gly Asn Gly Met Ala Asp Phe Val His Lys
145                 150                 155                 160

Gly Val Pro Asp Thr Val Gly Asp Tyr Asp Leu Tyr Cys His Tyr Val
                165                 170                 175

Ala Gly Val Val Gly Leu Gly Leu Ser Gln Leu Phe Val Ala Ser Gly
            180                 185                 190

Leu Gln Ser Pro Ser Leu Thr Arg Ser Glu Asp Leu Ser Asn His Met
```

```
                195                 200                 205
Gly Leu Phe Leu Gln Lys Thr Asn Ile Ile Arg Asp Tyr Phe Glu Asp
    210                 215                 220

Ile Asn Glu Leu Pro Ala Pro Arg Met Phe Trp Pro Arg Glu Ile Trp
225                 230                 235                 240

Gly Lys Tyr Ala Asn Asn Leu Ala Glu Phe Lys Asp Pro Ala Asn Lys
                245                 250                 255

Ala Ala Ala Met Cys Cys Leu Asn Glu Met Val Thr Asp Ala Leu Arg
            260                 265                 270

His Ala Val Tyr Cys Leu Gln Tyr Met Ser Met Ile Glu Asp Pro Gln
        275                 280                 285

Ile Phe Asn Phe Cys Ala Ile Pro Gln Thr Met Ala Phe Gly Thr Leu
    290                 295                 300

Ser Leu Cys Tyr Asn Asn Tyr Thr Ile Phe Thr Gly Pro Lys Ala Ala
305                 310                 315                 320

Val Lys Leu Arg Arg Gly Thr Thr Ala Lys Leu Met Tyr Thr Ser Asn
                325                 330                 335

Asn Met Phe Ala Met Tyr Arg His Phe Leu Asn Phe Ala Glu Lys Leu
            340                 345                 350

Glu Val Arg Cys Asn Thr Glu Thr Ser Glu Asp Pro Ser Val Thr Thr
        355                 360                 365

Thr Leu Glu His Leu His Lys Ile Lys Ala Ala Cys Lys Ala Gly Leu
    370                 375                 380

Ala Arg Thr Lys Asp Asp Thr Phe Asp Glu Leu Arg Ser Arg Leu Leu
385                 390                 395                 400

Ala Leu Thr Gly Gly Ser Phe Tyr Leu Ala Trp Thr Tyr Asn Phe Leu
                405                 410                 415

Asp Leu Arg Gly Pro Gly Asp Leu Pro Thr Phe Leu Ser Val Thr Gln
            420                 425                 430

His Trp Trp Ser Ile Leu Ile Phe Leu Ile Ser Ile Ala Val Phe Phe
        435                 440                 445

Ile Pro Ser Arg Pro Ser Pro Arg Pro Thr Leu Ser Ala
    450                 455                 460
```

<210> SEQ ID NO 15
<211> LENGTH: 6265
<212> TYPE: DNA
<213> ORGANISM: Artificial Sequence
<220> FEATURE:
<223> OTHER INFORMATION: Synthetic Construct

<400> SEQUENCE: 15

```
gcactttttcg gggaaatgtg cgcggaaccc ctatttgttt attttttctaa atacattcaa      60
atatgtatcc gctcatgaga caataaccct gataaatgct tcaataatat tgaaaaagga     120
agagtatgag tattcaacat ttccgtgtcg cccttattcc cttttttgcg gcattttgcc     180
ttcctgtttt tgctcaccca gaaacgctgg tgaaagtaaa agatgctgaa gatcagttgg     240
gtgcacgagt gggttacatc gaactggatc tcaacagcgg taagatcctt gagagttttc     300
gccccgaaga acgttttcca atgatgagca cttttaaagt tctgctatgt ggcgcggtat     360
tatcccgtat tgacgccggg caagagcaac tcggtcgccg catacactat tctcagaatg     420
acttggttga gtactcacca gtcacagaaa agcatcttac ggatggcatg acagtaagag     480
aattatgcag tgctgccata accatgagtg ataacactgc ggccaactta cttctgacaa     540
cgatcggagg accgaaggag ctaaccgctt ttttgcacaa catgggggat catgtaactc     600
```

```
gccttgatcg ttgggaaccg gagctgaatg aagccatacc aaacgacgag cgtgacacca    660
cgatgcctgt agcaatggca acaacgttgc gcaaactatt aactggcgaa ctacttactc    720
tagcttcccg gcaacaatta atagactgga tggaggcgga taaagttgca ggaccacttc    780
tgcgctcggc ccttccggct ggctgggttta ttgctgataa atctggagcc ggtgagcgtg    840
ggtctcgcgg tatcattgca gcactggggc cagatggtaa gccctcccgt atcgtagtta    900
tctacacgac ggggagtcag gcaactatgg atgaacgaaa tagacagatc gctgagatag    960
gtgcctcact gattaagcat tggtaactgt cagaccaagt ttactcatat atactttaga   1020
ttgatttaaa acttcatttt taatttaaaa ggatctaggt gaagatcctt tttgataatc   1080
tcatgaccaa aatcccttaa cgtgagtttt cgttccactg agcgtcagac cccgtagaaa   1140
agatcaaagg atcttcttga gatccttttt ttctgcgcgt aatctgctgc ttgcaaacaa   1200
aaaaaccacc gctaccagcg gtggtttgtt tgccggatca agagctacca actctttttc   1260
cgaaggtaac tggcttcagc agagcgcaga taccaaatac tgtccttcta gtgtagccgt   1320
agttaggcca ccacttcaag aactctgtag caccgcctac atacctcgct ctgctaatcc   1380
tgttaccagt ggctgctgcc agtggcgata agtcgtgtct taccgggttg actcaagac    1440 gatagttacc ggataaggcg cagcggtcgg gctgaacggg gggttcgtgc acacagccca   1500
gcttggagcg aacgacctac accgaactga gatacctaca gcgtgagcta tgagaaagcg   1560
ccacgcttcc cgaagggaga aaggcggaca ggtatccggt aagcggcagg gtcggaacag   1620
gagagcgcac gagggagctt ccaggggga acgcctggta tctttatagt cctgtcgggt   1680
ttcgccacct ctgacttgag cgtcgatttt tgtgatgctc gtcaggggggg cggagcctat   1740 ggaaaaacgc cagcaacgcg ccttttttac ggttcctggc cttttgctgg cctttttgctc   1800 acatgttctt tcctgcgtta tcccctgatt ctgtggataa ccgtattacc gcctttgagt   1860
gagctgatac cgctcgccgc agccgaacga ccgagcgcag cgagtcagtg agcgaggaag   1920
cggaagagcg cccaatacgc aaaccgcctc tccccgcgcg ttggccgatt cattaatgca   1980
gctggcacga caggttttcc cgactggaaag cgggcagtga gcgcaacgca attaatgtga   2040
gttagctcac tcattaggca ccccaggctt tacactttat gcttccggct cgtatgttgt   2100
gtggaattgt gagcggataa caatttcaca caggaaacag ctatgaccat gattacgcca   2160
agctcgaaat taaccctcac taaagggaac aaaagctgga gctccagctt tgttcccttt   2220
gatggggtat ttgagcactt gcaacccttta tccggaagcc ccctggccca caaaggctag   2280
gcgccaatgc aagcagttcg catgcagccc ctggagcggt gccctcctga taaaccggcc   2340
agggggccta tgttctttac tttttttacaa gagaagtcac tcaacatctt aaaatggggt   2400
gagtcgacga gcaagcccgg cggatcaggc agcgtgcttg cagatttgac ttgcaacgcc   2460
cgcattgtgt cgacgaaggc ttttggctcc tctgtcgctg tctcaagcag catctaaccc   2520
tgcgtcgccg tttccatttg caggatgctt cgctggggag tggagtcttt gcagaatcca   2580
gatgaattaa tcccggtctt gaggtgagtc gacgagcaag cccggcggat caggcagcgt   2640
gcttgcagat ttgacttgca acgcccgcat tgtgtcgacg aaggcttttg ctcctctgt    2700 cgctgtctca agcagcatct aaccctgcgt cgccgtttcc atttgcagga tgatttatgc   2760
tgataagttt ggaaagatca agccaaagga cgaagaccgg ggcttctgct atgaaatttt   2820
aaaccttgtt tcaagaagtt ttgcaatcgt catccaacag ctccctgcac agctgaggga   2880
cccagtctgc atattttacc ttgtactacg cgccctggac acagtcgaag atgatatgaa   2940
aattgcagca accaccaaga ttcccttgct gcgtgacttt tatgagaaaa tttctgacag   3000
```

```
gtcattccgc atgacggccg gagatcaaaa agactacatc aggctgttgg atcagtaccc    3060
caaagtgaca agcgttttct tgaaattgac cccccgtgaa caagagataa ttgcagacat    3120
tacaaagcgg atggggaatg gaatggctga cttcgtgcat aagggtgttc ccgacacagt    3180
gggggactac gacctttact gccactatgt tgctggggtg gtgggtctcg gctttccca    3240 gttgttcgtt gcgagtggac tacagtcacc ctctttgacc cgcagtgaag acctttccaa    3300
tcacatgggc ctcttccttc agaagaccaa catcatccgc gactactttg aggacatcaa    3360
tgagctgcct gccccccgga tgttctggcc cagagagatc tggggcaagt atgcgaacaa    3420
cctcgctgag ttcaaagacc cggccaacaa ggcggctgca atgtgctgcc tcaacgagat    3480
ggtcacagat gcattgaggc acgcggtgta ctgcctgcag tacatgtcca tgattgagga    3540
tccgcagatc ttcaacttct gtgccatccc tcagaccatg gccttcggca ccctgtcttt    3600
gtgttacaac aactacacta tcttcacagg gcccaaagcg gctgtgaagc tgcgtagggg    3660
caccactgcc aagctgatgt acacctctaa caatatgttt gcgatgtacc gtcatttcct    3720
caacttcgca gagaagctgg aagtcagatg caacaccgag accagcgagg atcccagcgt    3780
gaccaccact ctggaacacc tgcataagat caaagctgcc tgcaaggctg gctggcacg    3840 cacaaaagat gacacctttg acgaattgag gagcaggttg ttagcgctga cgggaggcag    3900
cttctacctc gcctggacct acaatttcct agaccttcga ggcccgggag acctgcccac    3960
cttcttatct gtaacccaac attggtggtc tattctgatc ttcctcattt cgattgccgt    4020
cttctttatt ccgtcgaggc cctcacctag acccacactc agcgcctaac cgacgtcgac    4080
ccactctaga ggatcgatcc ccgctccgtg taaatggagg cgctcgttga tctgagcctt    4140 gcccctgac gaacggcggt ggatggaaga tactgctctc aagtgctgaa gcggtagctt    4200
agctccccgt tcgtgctga tcagtctttt tcaacacgta aaaagcggag gagttttgca    4260 atttgttgg ttgtaacgat cctccgttga ttttggcctc tttctccatg ggcgggctgg    4320
gcgtatttga agcccactag ttctagagcg gccgctctag aactagtgga tcccccgggc    4380
tgcaggaatt cgatatcaag cttatcgata ccgtcgacct cgagatttaa atgccagaag    4440
gagcgcagcc aaaccaggat gatgtttgat ggggtatttg agcacttgca acccttatcc    4500
ggaagccccc tggcccacaa aggctaggcg ccaatgcaag cagttcgcat gcagccctg    4560 gagcggtgcc ctcctgataa accggccagg gggcctatgt tctttacttt tttacaagag    4620
aagtcactca acatcttaaa atggccaggt gagtcgacga gcaagcccgg cggatcaggc    4680
agcgtgcttg cagatttgac ttgcaacgcc cgcattgtgt cgacgaaggc ttttggctcc    4740
tctgtcgctg tctcaagcag catctaaccc tgcgtcgccg tttccatttg caggatggcc    4800
aagctgacca cgccgttcc ggtgctcacc gcgcgcgacg tcgccggagc ggtcgagttc    4860
tggaccgacc ggctcgggtt ctcccgggac ttcgtggagg acgacttcgc cggtgtggtc    4920
cgggacgacg tgaccctgtt catcagcgcg tccaggacc aggtgagtcg acgagcaagc    4980
ccggcggatc aggcagcgtg cttgcagatt tgacttgcaa cgcccgcatt gtgtcgacga    5040
aggcttttgg ctcctctgtc gctgtctcaa gcagcatcta accctgcgtc gccgtttcca    5100
tttgcaggac caggtggtgc cggacaacac cctggcctgg gtgtgggtgc gcggcctgga    5160
cgagctgtac gccgagtggt cggaggtcgt gtccacgaac ttccgggacg cctccgggcc    5220
ggccatgacc gagatcggcg agcagccgtg ggggcgggag ttcgccctgc gcgacccggc    5280
cggcaactgc gtgcacttcg tggccgagga gcaggactaa ccgacgtcga cccactctag    5340
aggatcgatc cccgctccgt gtaaatggag gcgctcgttg atctgagcct tgccccctga    5400
```

-continued

```
cgaacggcgg tggatggaag atactgctct caagtgctga agcggtagct tagctccccg    5460
tttcgtgctg atcagtcttt ttcaacacgt aaaaagcgga ggagttttgc aattttgttg    5520
gttgtaacga tcctccgttg attttggcct ctttctccat gggcgggctg ggcgtatttg    5580
aagcttaatt aactcgaggg ggggcccggt acccaattcg ccctatagtg agtcgtatta    5640
caattcactg gccgtcgttt tacaacgtcg tgactgggaa accctggcg ttacccaact     5700 taatcgcctt gcagcacatc ccccttcgc cagctggcgt aatagcgaag aggcccgcac     5760
cgatcgccct tcccaacagt tgcgcagcct gaatggcgaa tggaaattgt aagcgttaat    5820
attttgttaa aattcgcgtt aaattttgt taaatcagct cattttttaa ccaataggcc     5880
gaaatcggca aaatcccctta taaatcaaaa gaatagaccg atagggtt gagtgttgtt     5940 ccagtttgga acaagagtcc actattaaag aacgtggact ccaacgtcaa agggcgaaaa    6000
accgtctatc agggcgatgg cccactacgt gaaccatcac cctaatcaag ttttttgggg    6060
tcgaggtgcc gtaaagcact aaatcggaac cctaaaggga gccccgatt tagagcttga    6120 cggggaaagc cggcgaacgt ggcgagaaag gaagggaaga agcgaaagg agcgggcgct     6180 agggcgctgg caagtgtagc ggtcacgctg cgcgtaacca ccacacccgc cgcgcttaat    6240
gcgccgctac agggcgcgtc aggtg                                         6265
```

<210> SEQ ID NO 16
<211> LENGTH: 22
<212> TYPE: DNA
<213> ORGANISM: Artificial Sequence
<220> FEATURE:
<223> OTHER INFORMATION: Synthetic Construct

<400> SEQUENCE: 16

```
ccttgatggg gtatttgagc ac                                              22
```

<210> SEQ ID NO 17
<211> LENGTH: 33
<212> TYPE: DNA
<213> ORGANISM: Artificial Sequence
<220> FEATURE:
<223> OTHER INFORMATION: Synthetic Construct

<400> SEQUENCE: 17

```
ggaattcggt taggcgctga gtgtgggtct agg                                  33
```

<210> SEQ ID NO 18
<211> LENGTH: 23
<212> TYPE: DNA
<213> ORGANISM: Artificial Sequence
<220> FEATURE:
<223> OTHER INFORMATION: Synthetic Construct

<400> SEQUENCE: 18

```
tgagcacttg caaccctat ccg                                              23
```

<210> SEQ ID NO 19
<211> LENGTH: 33
<212> TYPE: DNA
<213> ORGANISM: Artificial Sequence
<220> FEATURE:
<223> OTHER INFORMATION: Synthetic Construct

<400> SEQUENCE: 19

```
ggaattcggt taggcgctga gtgtgggtct agg                                  33
```

<210> SEQ ID NO 20

```
<211> LENGTH: 42
<212> TYPE: PRT
<213> ORGANISM: Botryococcus braunii

<400> SEQUENCE: 20

Ile Leu Glu Gly Leu Thr Glu Lys Val Arg Gln Arg Lys Gly Arg Ile
1               5                   10                  15

Ala Arg Leu Val Met Ser Ser Arg Asn Val Pro Gly Leu Phe Arg Thr
                20                  25                  30

Cys Leu Lys Leu Ala Lys Asn Phe Glu Ala
            35                  40

<210> SEQ ID NO 21
<211> LENGTH: 56
<212> TYPE: PRT
<213> ORGANISM: Botryococcus braunii

<400> SEQUENCE: 21

Met Ser Met His Gln Asp Lys Gly Val Ala Lys Asp Leu Leu Arg His
1               5                   10                  15

Pro Gly Glu Phe Pro Tyr Leu Leu Gln Leu Ala Ala Thr Thr Tyr Gly
                20                  25                  30

Thr Pro Ala Ala Pro Ile Pro Lys Glu Pro Asp Arg Ala Phe Cys Tyr
            35                  40                  45

Asn Thr Leu His Ala Val Ser Lys
        50                  55

<210> SEQ ID NO 22
<211> LENGTH: 53
<212> TYPE: PRT
<213> ORGANISM: Botryococcus braunii

<400> SEQUENCE: 22

Phe Pro Arg Phe Val His Arg Leu Pro Leu Glu Leu Gln Asp Pro Ile
1               5                   10                  15

Cys Ile Phe Tyr Leu Leu Leu Arg Ala Leu Asp Thr Val Glu Asp Asp
                20                  25                  30

Met Asn Leu Pro Ser Lys Val Lys Val Asp Leu Leu Arg Glu Phe His
            35                  40                  45

Glu His Cys Lys Asp
        50

<210> SEQ ID NO 23
<211> LENGTH: 34
<212> TYPE: PRT
<213> ORGANISM: Botryococcus braunii

<400> SEQUENCE: 23

Asn Trp Ser Met Lys Ser Asp Tyr Gly Ile Tyr Ala Asp Leu Met Glu
1               5                   10                  15

Arg Phe Pro Leu Val Ile Ser Val Leu Glu Lys Leu Pro Lys Pro Thr
                20                  25                  30

Gln Glu

<210> SEQ ID NO 24
<211> LENGTH: 44
<212> TYPE: PRT
<213> ORGANISM: Botryococcus braunii

<400> SEQUENCE: 24

Val Phe Val Glu Asn Val Lys Tyr Met Gly Asn Gly Met Ala Asp Phe
```

```
1               5                   10                  15

Ile Asp Lys Glu Ile Leu Thr Val Asp Glu Tyr Asp Leu Tyr Cys His
            20                  25                  30

Tyr Val Ala Gly Ser Cys Gly Ile Ala Val Val Lys
        35                  40

<210> SEQ ID NO 25
<211> LENGTH: 44
<212> TYPE: PRT
<213> ORGANISM: Botryococcus braunii

<400> SEQUENCE: 25

Val Ile Val Gln Phe Asn Leu Ala Thr Pro Glu Ala Asp Ser Met Glu
1               5                   10                  15

Phe Ser Asn Ser Leu Gly Leu Leu Leu Gln Lys Ala Asn Ile Ile Thr
            20                  25                  30

Asp Tyr Asn Glu Asp Ile Asn Glu Glu Pro Arg Pro
        35                  40

<210> SEQ ID NO 26
<211> LENGTH: 83
<212> TYPE: PRT
<213> ORGANISM: Botryococcus braunii

<400> SEQUENCE: 26

Met Phe Trp Pro Gln Glu Ile Trp Ala Asn Tyr Ser Glu Lys Leu Ala
1               5                   10                  15

Asp Phe Asn Glu Pro Ala Asn Leu Glu Lys Ala Met Lys Cys Leu Asn
            20                  25                  30

His Met Val Thr Asp Ala Leu Arg His Ile Glu Pro Ser Leu Lys Gly
        35                  40                  45

Met Val Tyr Phe Thr Asp Gly Thr Val Phe Arg Ala Leu Ala Leu Leu
    50                  55                  60

Leu Val Thr Ala Phe Gly His Leu Ser Thr Leu Tyr Asn Asn Pro Asn
65                  70                  75                  80

Val Phe Arg

<210> SEQ ID NO 27
<211> LENGTH: 35
<212> TYPE: PRT
<213> ORGANISM: Botryococcus braunii

<400> SEQUENCE: 27

Lys Val Arg Gln Arg Lys Gly Arg Ile Ala Arg Leu Val Met Ser Ser
1               5                   10                  15

Arg Asn Val Pro Gly Leu Phe Arg Thr Cys Leu Lys Leu Ala Lys Asn
            20                  25                  30

Phe Glu Ala
        35

<210> SEQ ID NO 28
<211> LENGTH: 49
<212> TYPE: PRT
<213> ORGANISM: Botryococcus braunii

<400> SEQUENCE: 28

Cys Leu Glu Glu Thr Lys Asn Asp Pro Ser Val Ala Thr Thr Ile Lys
1               5                   10                  15

Arg Leu Gln Ser Ile Gln Ala Thr Cys Arg Glu Gly Leu Glu Lys Tyr
            20                  25                  30
```

```
Glu Thr Pro Ser Gly Leu Arg Ala Leu Cys Ala Ala Pro Ser Pro Thr
         35                  40                  45
Lys

<210> SEQ ID NO 29
<211> LENGTH: 403
<212> TYPE: PRT
<213> ORGANISM: Botryococcus braunii

<400> SEQUENCE: 29

Met Ser Met His Gln Asp Lys Gly Val Ala Lys Asp Leu Leu Arg His
1               5                   10                  15

Pro Gly Glu Phe Pro Tyr Leu Leu Gln Leu Ala Ala Thr Thr Tyr Gly
            20                  25                  30

Thr Pro Ala Ala Pro Ile Pro Lys Glu Pro Asp Arg Ala Phe Cys Tyr
        35                  40                  45

Asn Thr Leu His Ala Val Ser Lys Gly Phe Pro Arg Phe Val His Arg
50                  55                  60

Leu Pro Leu Glu Leu Gln Asp Pro Ile Cys Ile Phe Tyr Leu Leu Leu
65                  70                  75                  80

Arg Ala Leu Asp Thr Val Glu Asp Asp Met Asn Leu Pro Ser Lys Val
                85                  90                  95

Lys Val Asp Leu Leu Arg Glu Phe His Glu His Cys Lys Asp Arg Asn
            100                 105                 110

Trp Ser Met Lys Ser Asp Tyr Gly Ile Tyr Ala Asp Leu Met Glu Arg
        115                 120                 125

Phe Pro Leu Val Ile Ser Val Leu Glu Lys Leu Pro Lys Pro Thr Gln
    130                 135                 140

Glu Val Phe Val Glu Asn Val Lys Tyr Met Gly Asn Gly Met Ala Asp
145                 150                 155                 160

Phe Ile Asp Lys Glu Ile Leu Thr Val Asp Gly Tyr Asp Leu Tyr Cys
                165                 170                 175

His Tyr Val Ala Gly Ser Cys Gly Ile Ala Val Val Lys Val Ile Val
            180                 185                 190

Gln Phe Asn Leu Ala Thr Pro Glu Ala Asp Ser Met Glu Phe Ser Asn
        195                 200                 205

Ser Leu Gly Leu Leu Gln Lys Ala Asn Ile Ile Thr Asp Tyr Asn
    210                 215                 220

Glu Asp Ile Asn Glu Glu Pro Arg Pro Arg Met Phe Trp Pro Gln Glu
225                 230                 235                 240

Ile Trp Ala Asn Tyr Ser Glu Lys Leu Ala Asp Phe Asn Glu Pro Ala
                245                 250                 255

Asn Leu Glu Lys Ala Met Lys Cys Leu Asn His Met Val Thr Asp Ala
            260                 265                 270

Leu Arg His Ile Glu Pro Ser Leu Lys Gly Met Val Tyr Phe Thr Asp
        275                 280                 285

Gly Thr Val Phe Arg Ala Leu Ala Leu Leu Val Thr Ala Phe Gly
    290                 295                 300

His Leu Ser Thr Leu Tyr Asn Asn Pro Asn Val Phe Arg Glu Lys Val
305                 310                 315                 320

Arg Gln Arg Lys Gly Arg Ile Ala Arg Leu Val Met Ser Ser Arg Asn
                325                 330                 335

Val Pro Gly Leu Phe Arg Thr Cys Leu Lys Leu Ala Lys Asn Phe Glu
            340                 345                 350
```

```
Ala Arg Cys Leu Glu Glu Thr Lys Asn Asp Pro Ser Val Ala Thr Thr
        355                 360                 365

Ile Lys Arg Leu Gln Ser Ile Gln Ala Thr Cys Arg Glu Gly Leu Glu
    370                 375                 380

Lys Tyr Glu Thr Pro Ser Gly Leu Arg Ala Leu Cys Ala Ala Pro Ser
385                 390                 395                 400

Pro Thr Lys

<210> SEQ ID NO 30
<211> LENGTH: 1212
<212> TYPE: DNA
<213> ORGANISM: Botryococcus braunii

<400> SEQUENCE: 30
atgagtatgc accaagacaa gggggttgct aaggatcttt taaggcatcc aggggaattc      60
ccctatttgc tccagctagc cgctacaact tacggcacac cggcggcccc gatcccaaag     120
gaacccgacc gagcgttctg ctataacact cttcacgctg tttctaaagg gttcccgagg     180
tttgttcaca ggcttcctct ggaactccag gatccaatct gcatttttta tctcctgctg     240
cgtgcactag atacagtgga ggatgatatg aacctcccaa gtaaggtgaa ggtagatctg     300
ttgcgcgagt tcatgagcat tgtaaagac aggaactgga gcatgaaaag tgattatggc      360
atctatgcag acttgatgga aaggtttcct ctggtgattt ccgtcctgga aaagcttcct     420
aagcccacac aggaggtttt tgtggagaat gtcaaatata tgggcaatgg catggcagac     480
tttattgata ggagatcttt gactgtggat gagtacgatc tgtactgcca ctatgtggct     540
ggtagttgtg gcattgctgt tgtcaaggtt attgtccaat taaccttgca cacgccggaa     600
gctgactcga tggagttttc caacagccta ggattgttgc ttcagaaagc caacatcatt     660
actgactaca atgaggacat taacgaagaa cccagacccc ggatgttctg gccccaagag     720
atctgggcca attactcgga aaagttagct gactttaatg aacccgccaa ccttgaaaaa     780
gctatgaagt gcttgaacca catggtcaca gatgccctgc ccacattga ccatctctt      840 aagggcatgg tttatttcac agacgggaca gtcttccgcg ctcttgctct ctgctggtc     900 acagcttttg gtcacttgtc gactttgtac aataacccaa atgttttccg agagaaggtg     960
aggcagcgga agggaaggat tgcccggcta gtgatgtcat ccagaaacgt accaggcctc    1020
ttccgcacct gcctaaaact tgcaaagaac tttgaagcca ggtgtctgga ggagacaaag    1080 aatgatcct ctgtggccac aaccatcaag cggctgcagt caatccaggc cacgtgcaga     1140
gaaggcctgg aaaaatatga gacaccatct gggctgaggg cgctctgtgc tgctccaagc    1200
cctacaaagt ga                                                       1212

<210> SEQ ID NO 31
<211> LENGTH: 6673
<212> TYPE: DNA
<213> ORGANISM: Botryococcus braunii

<400> SEQUENCE: 31
gcgcgcgcgc gcgtgtctgt gcgagtaatc tccgcctcca catttccccc ttctagtgta      60
agaaggattc catgagcttt ggggttcaag gaaaatgaag tgcatttcac ccagatcgtt     120
tgggactagt agggtgttac ccatacttct gttaagaatt cctcaccaac aagatcttct     180
aaatgtttgg ccatctgaat tcatattctc ataaaaccca gggcaggctt ggaagtatga     240 agaacagag aaggtacatc cggggagcca ctgaagcctg ggggatggag cgactcccat      300
atcgaccgac atgtgagtgc aaggaagaaa gtcttgacac cctcggagct tggtatattt     360
```

```
tttttttttgt atctaaaagt ctttttttctc tgagtagata taaacgaaga aatgaagcat    420
atatatccag gtcgtagcat gagggcgata tatttcactc tcgttaggta agatactttt    480
attgcggggg ataggtttta ctgcgtaatt gacagcccga tcacctgatc gggcgtaaaa    540
cctaacagaa gccccgctga gcctcacgtc atcatcatca ttcttgctgc tgtgaagcat    600
gctggcctca cgttgactag ggttgaataa attttaacaa gagggactag aaggtgaggc    660
cgagacaaca gcagcgtgta acggggaca acgcaaaacc ttggtatgta gtctgggggg    720
tcggcattgt ggacattttt gaagagctca cgggccagat gctagataaa tcttgtgtca    780
agtgtaggca aaagatgca ggaattcttg tgtcacgaat aggggaaagc aatgcaggga    840
tttgagattg cgagaaatga gtaacccaaa attcgtgctg cgtttagcgc gtaagaatta    900
tcagtcagct tccctgcatc aattgatgta gggcctaggc aggcgatgat gacattgaaa    960
gttgtcgtca gatggactga ctgatcgtcc ataaaccagc cgctgaaatc catctccgtc   1020
tccagccgtt aaaccccgcc ccgatggttg gccgaaattg ggtcagcgtc cccgcgtcgg   1080
cccgtgtcgt cctagcgaga gcaatcgtcc ttggacaacg gcaaccgttt tcgaattggt   1140
gtgcatgctg ccagccatat gaggaaacag caagcctaag gttgttactc ttaggcctca   1200
taaagtagga gtatagcgat cccccgtctg caggccggcg aagactccgc gagatccgga   1260
ggagagaaat aggccacaat gagtatgcac caagacaagg gggttgctaa ggatctttta   1320
aggcatccag gggaattccc ctatttgctc cagctagccg ctacaactta cggcacaccg   1380
gcggccccga tcccaaagga acccgaccga gcgttctgct ataacactct tcacgctgtt   1440
tctaaagggt gagatattgc tgaattgctt tcacttactt ccaattcaac tggcaaactg   1500
tggaattgga aaagagtggc gttctggaac gtgaaggcta cgagttatcg agacagaagt   1560
tgtttaactt gaccgcaatc ttccagcggt tcctcttctg tttctctttt aaatagggcc   1620
cataggatcc cgtttctctt ttttatgtta attccgggga tctcatttgt acatctgtgt   1680
ctgtttgttc gcacgggtat atactctctt tcggggttga gtgttacctc tatgttttgt   1740
gtggatttca atctagattt tagtgatgtt gacgatctgt ttgaaattgc atcagctcat   1800
cccctgtaag agcagggtgg ctgtccctac tgatgggttt ctctggtgtc tgcaggttcc   1860
cgaggtttgt tcacaggctt cctctggaac tccaggatcc aatctgcatt ttttatctcc   1920
tgctgcgtgc actagataca gtggaggatg atatgaacct cccaagtaag gtgaaggtag   1980
atctgttgcg cgagtttcat gagcattgta aagacaggtg cgtcccttgt tctcatggaa   2040
ctagataaca gcaaatgcac atattctaca gaggagtgtt tttctgtgtg tctgtgttac   2100
tgcgctgaca cgcacttgac ccctccccgt tcttcgctcc agtttgcttc cctcttttcc   2160
gcttcttctg cttctgaccc tacctaacac tccaaatcca acccctccc cccccccca   2220 aaaaaaaaaa aaagaaggg actactgtgt gtgaacgttc accatcctcg cctctgctgg   2280
gagtgggatt ctggtttctg acacacacac acacagccaa gaagagcaag aaggacgaag   2340
ggactactgt gtgtgaaggg tcaacatcct cgactctgat ggttgtggga tgatggtttc   2400
tgactttttg actcattgtg agcataatct gggggtaatt caactttttt tcttgctcta   2460
ggactttgta aataccctga caatgtatct gcctacagtt tctactccat ttcgagatgt   2520
gctaagttca caaacgagtt ccttgtatgc aggaactgga gcatgaaaag tgattatggc   2580
atctatgcag acttgatgga aaggtttcct ctggtgattt ccgtcctgga aaagcttcct   2640
aagcccacac aggaggtagg aaagaagctg tagcccaagc ttttgagcg agcttatctg   2700 agtgctcgaa cgggtactca gcttgggtcc ttcctacatg tggctggcga gaacactaac   2760
```

```
agttgcaatg aagagttctt caggaggatt gctggctgcc atgtcttgtt ttgttgtcca    2820
gaggagtttt cagctacgtt tgaaatgcta ctgttgtacc taaagtggag aatgtaggga    2880
aagtcagttg tcgtccccct cttttttctg tttgagttgt gttcccatta ttcaatagca    2940
tttcctgatg gttgtatggt ggatgtcttg catcccagat acaaatacaa gccaattttg    3000
caggagagca ctcctgaaga tggtgtcctt ccactgttgt cacggacgag gggtgctgaa    3060
tgttgtgggc acaaacagca gtgcatccca tacatggaat gttgttgtct acacgttgac    3120
acgttccaag catcactagc tgccctcctg atactcttct cggtcatcta agctcacgca    3180
tccgaacatg gcactttaca aaagaaaca gtgttttttg acgttgaaca ggttttttgtg    3240 gagaatgtca atatatgggg caatggcatg gcagacttta ttgataagga gatcttgact    3300
gtggatgagt acgatctgta ctgccactat gtggctggta gttgtggcat tgctgttgtc    3360
aaggtacgta ctctctaaca tagtctggta cccccagttt tgcctctgca gatgttattg    3420
caagtggctt ccacgaacac catgggctcc tggtgcagtc caacttgcga ggtcatgggc    3480
ttgaagtcgc cctgtctacg gaacacccga ttcatgacca aggttacata atatcgttgt    3540
tccttaattc ggaatactaa agttaaggtt tcggaacgtc taccctaagc cctagaacac    3600
cgccaattgg cctgggagac atttctagtg tgttttctgg tcttgcgagg atgtttccag    3660
agcctttccg atctaccaat ggtacagttt acgtaatgct tcaggtgaac tgtagactgt    3720 gggggggtgga agtggagtgg tgtccaatgt tgtaatgcac tttgtaatct gagagccagg    3780
ttctggctcc tgtattgtgg gggctgctct gttgtctatt acacaactag agttgtatgt    3840
agccagtggc agttgtgagt tggatgggac tgtgggacca ggttattgtc caatttaacc    3900
ttgccacgcc ggaagctgac tcgatggagt ttttccaacag cctaggattg ttgcttcaga    3960
aagccaacat cattactgac tacaatgagg acattaacga agaacccaga ccccggtatg    4020
ccactagcat attcagagac acatggctct gtacacaatc ttactgtaaa aatgactgaa    4080
aggagtggct gcaatgtttt gtctgtcaaa cctatcaggg caagtcgact tgaaggtctg    4140
gttcgcaata tgggttttgc atggtcacgt ttagagtatg tggtaacgat tgatatctcc    4200
tctgaagtgc catttgctgt atgtatggag tggccgtcag aagtcccagg ataagagcaa    4260
ctggttattg tcaaaaactt tgactgggta cattgggagt tcctgcagga tgttctggcc    4320
ccaagagatc tgggccaatt actcggaaaa gttagctgac tttaatgaac ccgccaacct    4380
tgaaaaagct atgaagtgct tgaaccacat ggtcacagat gccctgcgcc acattgagcc    4440
atctcttaag ggcatggttt atttcacaga cgggacagtc ttccgcgctc ttgctcttct    4500
gctggtcaca gcttttggtc acttgtcgac tttgtacaat aacccaaatg ttttttccgagg    4560 tataatatct ttgccgtgtc tggtgctcgc actcacaagg gtgtcataat aatctagctt    4620
tccctgtcag aatgaagtcc agatactctt gggacatctg tgcctccaat cttggttgta    4680
gggtgtgaat gctgtttccg gctctgatgg atgcgctaac atagttttga gctagtgtac    4740
ttgcttccac atgggggttct aacctgactc ttcttcaagc agtgtgtaca tgttttgttg    4800
gaggctttgg tggacattgt gcctatgaca gaaagtcaaa ggtcgctggc cagttaagtg    4860
cagaaggtgc ttagagtcac tcttaaatca gggaatgtga gcgaacaaca tgcacaccga    4920
tcatgattaa gggccacgga tgatgtcttt ggtaaagcaa gtacgcgtat ttagaatgtg    4980
tctgcaaaaa acttgttttc ctgtgttttta agtgcctttg aagccgtccg tcacagggat    5040
tgtagtaatt ctgtgaattg gaaggattta aacccattgt aaattgtttt tttctgccgg    5100
ccagtccagc ttgactgctg agacacacat cacatgttaa caggtacatt accatgcaga    5160
```

| | |
|---|---|
| acattttatg tggggaccgc ataatcagca attacgtttt atatggaaca gtttgtacaa | 5220 |
| ctggcagttt ccaatctcac ccacactttg ctcctcaaca ctcacgtcga cttaaatgct | 5280 |
| gtggagacca aaaacatcga tggcattctg agtcttccct ttacaatgtc cacagtgatg | 5340 |
| tagtcaattg agggaggggt acaggagact ctgtagatct tgtatccact ccccacagca | 5400 |
| cttgaaaccg ttgtttggaa gctgatttga gcttttagg catgtgagct agtctctcaa | 5460 |
| ggtggttcct gatgattgaa tgcattttgg agggtttgac agagaaggtg aggcagcgga | 5520 |
| agggaaggat tgcccggcta gtgatgtcat ccagaaacgt accaggcctc ttccgcacct | 5580 |
| gcctaaaact tgcaaagaac tttgaagcca ggtatatgcc cctctgcctt tggaacaaac | 5640 |
| cctgacggtt gatttactgt aaagaatagc agtcctgtgt gtcatttgtc tcttgtgggg | 5700 |
| ccaaagttcc cttgtgtaag aatggcagtc tggcacagct tgagatttat atcttgtctg | 5760 |
| agtatcagct ttaagtatac ttcagtgctc cacattggta ccccatctac attctccagc | 5820 |
| atcctgtagg gcttgataca tggaaggaga tacttcccac atgtctctcc ccttttctca | 5880 |
| agagaggcag ccatctttgg agttatgagt tacaatcagg ctccaacttg gacctctcaa | 5940 |
| tggaatcttg catgcacagg agcatatagc ttgcctcaaa tatagagata actcagttta | 6000 |
| gccctggctg tctgattttc tgccccgaac gggagggtct ccaacgcaga tggcggagaa | 6060 |
| ccaccggaaa tgtgatttct ccaagtaatc tttgtgtttg acaaagtggt tcggccggac | 6120 |
| atacattcgg tcactgtatg acatgagatg cgctgcaggt gtctggagga gacaaagaat | 6180 |
| gatccctctg tggccacaac catcaagcgg ctgcagtcaa tccaggccac gtgcagaaga | 6240 |
| ggcctggaaa aatatgagac accatctggg ctgagggcgc tctgtgctgc tccaagccct | 6300 |
| acaaagtgag gtcaatagaa atatggtaag ttttaactct tgctccacgt gcaagacgct | 6360 |
| gcaatcctag tactccgtgc tgtaccatgt gataggaact tcaaatggca ggcaattgca | 6420 |
| gtggttgctg ggtctgggga cacattcggc tccctctat ctatgcttta cttgctgtgt | 6480 |
| cctttcaatt ccctgatgca ttcagtatcc cttcttcaaa caattagtat gatggtattc | 6540 |
| caaagctcga tgattgcaca tgttatgcat gcacacatta atggtaagtt taaagtgcac | 6600 |
| agatggttgc aggctgtgtg ggccagtttg tgcttttgct tagaactaat ccattgtacg | 6660 |
| tccccacccc tac | 6673 |

<210> SEQ ID NO 32
<211> LENGTH: 1245
<212> TYPE: DNA
<213> ORGANISM: Artificial Sequence
<220> FEATURE:
<223> OTHER INFORMATION: Synthetic Construct

<400> SEQUENCE: 32

| | |
|---|---|
| caccacatgc atatgagtat gcaccaagac aagggggttg ctaaggatct tttaaggcat | 60 |
| ccaggggaat tcccctattt gctccagcta gccgctacaa cttacggcac accggcggcc | 120 |
| ccgatcccaa aggaacccga ccgagcgttc tgctataaca ctcttcacgc tgtttctaaa | 180 |
| gggttcccga ggtttgttca caggcttcct ctggaactcc aggatccaat ctgcattttt | 240 |
| tatctcctgc tgcgtgcact agatacagtg gaggatgata tgaacctccc aagtaaggtg | 300 |
| aaggtagatc tgttgcgcga gtttcatgag cattgtaaag acaggaactg gagcatgaaa | 360 |
| agtgattatg gcatctatgc agacttgatg gaaaggtttc ctctggtgat ttccgtcctg | 420 |
| gaaaagcttc ctaagcccac acaggaggtt tttgtggaga atgtcaaata tatgggcaat | 480 |
| ggcatggcag actttattga taaggagatc ttgactgtgg atgagtacga tctgtactgc | 540 |

```
cactatgtgg ctggtagttg tggcattgct gttgtcaagg ttattgtcca atttaacctt        600
gccacgccgg aagctgactc gatggagttt ccaacagcc taggattgtt gcttcagaaa         660
gccaacatca ttactgacta caatgaggac attaacgaag aacccagacc ccggatgttc        720
tggccccaag agatctgggc caattactcg gaaaagttag ctgactttaa tgaacccgcc        780
aaccttgaaa aagctatgaa gtgcttgaac cacatggtca cagatgccct gcgccacatt       840
gagccatctc ttaagggcat ggtttatttc acagacggga cagtcttccg cgctcttgct       900
cttctgctgg tcacagcttt tggtcacttg tcgactttgt acaataaccc aaatgttttc       960
cgagagaagg tgaggcagcg gaagggaagg attgcccggc tagtgatgtc atccagaaac      1020
gtaccaggcc tcttccgcac ctgcctaaaa cttgcaaaga actttgaagc caggtgtctg      1080
gaggagacaa agaatgatcc ctctgtggcc acaaccatca agcggctgca gtcaatccag      1140
gccacgtgca gagaaggcct ggaaaaatat gagacaccat ctgggctgag ggcgctctgt      1200
gctgctccaa gccctacaaa gatgcattga tcactcgagc ccggg                      1245
```

<210> SEQ ID NO 33
<211> LENGTH: 12
<212> TYPE: DNA
<213> ORGANISM: Artificial Sequence
<220> FEATURE:
<223> OTHER INFORMATION: Synthetic Construct

<400> SEQUENCE: 33
caccacatgc at        12

<210> SEQ ID NO 34
<211> LENGTH: 6
<212> TYPE: DNA
<213> ORGANISM: Artificial Sequence
<220> FEATURE:
<223> OTHER INFORMATION: Synthetic Construct

<400> SEQUENCE: 34 atgcat        6

<210> SEQ ID NO 35
<211> LENGTH: 6
<212> TYPE: DNA
<213> ORGANISM: Artificial Sequence
<220> FEATURE:
<223> OTHER INFORMATION: Synthetic Construct

<400> SEQUENCE: 35 catatg        6

<210> SEQ ID NO 36
<211> LENGTH: 405
<212> TYPE: PRT
<213> ORGANISM: Artificial Sequence
<220> FEATURE:
<223> OTHER INFORMATION: Synthetic Construct

<400> SEQUENCE: 36

Met Ser Met His Gln Asp Lys Gly Val Ala Lys Asp Leu Leu Arg His
1               5                   10                  15

Pro Gly Glu Phe Pro Tyr Leu Leu Gln Leu Ala Ala Thr Thr Tyr Gly
                20                  25                  30

Thr Pro Ala Ala Pro Ile Pro Lys Glu Pro Asp Arg Ala Phe Cys Tyr
        35                  40                  45

-continued

Asn Thr Leu His Ala Val Ser Lys Gly Phe Pro Arg Phe Val His Arg
 50                  55                  60

Leu Pro Leu Glu Leu Gln Asp Pro Ile Cys Ile Phe Tyr Leu Leu Leu
 65                  70                  75                  80

Arg Ala Leu Asp Thr Val Glu Asp Met Asn Leu Pro Ser Lys Val
                 85                  90                  95

Lys Val Asp Leu Leu Arg Glu Phe His Glu His Cys Lys Asp Arg Asn
                100                 105                 110

Trp Ser Met Lys Ser Asp Tyr Gly Ile Tyr Ala Asp Leu Met Glu Arg
            115                 120                 125

Phe Pro Leu Val Ile Ser Val Leu Glu Lys Leu Pro Lys Pro Thr Gln
        130                 135                 140

Glu Val Phe Val Glu Asn Val Lys Tyr Met Gly Asn Gly Met Ala Asp
145                 150                 155                 160

Phe Ile Asp Lys Glu Ile Leu Thr Val Asp Glu Tyr Asp Leu Tyr Cys
                165                 170                 175

His Tyr Val Ala Gly Ser Cys Gly Ile Ala Val Val Lys Val Ile Val
            180                 185                 190

Gln Phe Asn Leu Ala Thr Pro Glu Ala Asp Ser Met Glu Phe Ser Asn
        195                 200                 205

Ser Leu Gly Leu Leu Gln Lys Ala Asn Ile Ile Thr Asp Tyr Asn
210                 215                 220

Glu Asp Ile Asn Glu Glu Pro Arg Pro Arg Met Phe Trp Pro Gln Glu
225                 230                 235                 240

Ile Trp Ala Asn Tyr Ser Glu Lys Leu Ala Asp Phe Asn Glu Pro Ala
                245                 250                 255

Asn Leu Glu Lys Ala Met Lys Cys Leu Asn His Met Val Thr Asp Ala
            260                 265                 270

Leu Arg His Ile Glu Pro Ser Leu Lys Gly Met Val Tyr Phe Thr Asp
        275                 280                 285

Gly Thr Val Phe Arg Ala Leu Ala Leu Leu Val Thr Ala Phe Gly
        290                 295                 300

His Leu Ser Thr Leu Tyr Asn Asn Pro Asn Val Phe Arg Glu Lys Val
305                 310                 315                 320

Arg Gln Arg Lys Gly Arg Ile Ala Arg Leu Val Met Ser Ser Arg Asn
                325                 330                 335

Val Pro Gly Leu Phe Arg Thr Cys Leu Lys Leu Ala Lys Asn Phe Glu
            340                 345                 350

Ala Arg Cys Leu Glu Glu Thr Lys Asn Asp Pro Ser Val Ala Thr Thr
        355                 360                 365

Ile Lys Arg Leu Gln Ser Ile Gln Ala Thr Cys Arg Glu Gly Leu Glu
370                 375                 380

Lys Tyr Glu Thr Pro Ser Gly Leu Arg Ala Leu Cys Ala Ala Pro Ser
385                 390                 395                 400

Pro Thr Lys Met His
            405

<210> SEQ ID NO 37
<211> LENGTH: 15
<212> TYPE: DNA
<213> ORGANISM: Artificial Sequence
<220> FEATURE:
<223> OTHER INFORMATION: Synthetic Construct

<400> SEQUENCE: 37
tcactcgagc ccggg                                                15

<210> SEQ ID NO 38
<211> LENGTH: 416
<212> TYPE: PRT
<213> ORGANISM: Artificial Sequence
<220> FEATURE:
<223> OTHER INFORMATION: Synthetic Construct

<400> SEQUENCE: 38

```
Met His His His His His His His Met His Met Ser Met His Gln
1               5                   10                  15

Asp Lys Gly Val Ala Lys Asp Leu Leu Arg His Pro Gly Glu Phe Pro
            20                  25                  30

Tyr Leu Leu Gln Leu Ala Ala Thr Thr Tyr Gly Thr Pro Ala Ala Pro
        35                  40                  45

Ile Pro Lys Glu Pro Asp Arg Ala Phe Cys Tyr Asn Thr Leu His Ala
    50                  55                  60

Val Ser Lys Gly Phe Pro Arg Phe Val His Arg Leu Pro Leu Glu Leu
65                  70                  75                  80

Gln Asp Pro Ile Cys Ile Phe Tyr Leu Leu Leu Arg Ala Leu Asp Thr
                85                  90                  95

Val Glu Asp Asp Met Asn Leu Pro Ser Lys Val Lys Val Asp Leu Leu
            100                 105                 110

Arg Glu Phe His Glu His Cys Lys Asp Arg Asn Trp Ser Met Lys Ser
        115                 120                 125

Asp Tyr Gly Ile Tyr Ala Asp Leu Met Glu Arg Phe Pro Leu Val Ile
    130                 135                 140

Ser Val Leu Glu Lys Leu Pro Lys Pro Thr Gln Glu Val Phe Val Glu
145                 150                 155                 160

Asn Val Lys Tyr Met Gly Asn Gly Met Ala Asp Phe Ile Asp Lys Glu
                165                 170                 175

Ile Leu Thr Val Asp Glu Tyr Asp Leu Tyr Cys His Tyr Val Ala Gly
            180                 185                 190

Ser Cys Gly Ile Ala Val Val Lys Val Ile Val Gln Phe Asn Leu Ala
        195                 200                 205

Thr Pro Glu Ala Asp Ser Met Glu Phe Ser Asn Ser Leu Gly Leu Leu
    210                 215                 220

Leu Gln Lys Ala Asn Ile Ile Thr Asp Tyr Asn Glu Asp Ile Asn Glu
225                 230                 235                 240

Glu Pro Arg Pro Arg Met Phe Trp Pro Gln Glu Ile Trp Ala Asn Tyr
                245                 250                 255

Ser Glu Lys Leu Ala Asp Phe Asn Glu Pro Ala Asn Leu Glu Lys Ala
            260                 265                 270

Met Lys Cys Leu Asn His Met Val Thr Asp Ala Leu Arg His Ile Glu
        275                 280                 285

Pro Ser Leu Lys Gly Met Val Tyr Phe Thr Asp Gly Thr Val Phe Arg
    290                 295                 300

Ala Leu Ala Leu Leu Val Thr Ala Phe Gly His Leu Ser Thr Leu
305                 310                 315                 320

Tyr Asn Asn Pro Asn Val Phe Arg Glu Lys Val Arg Gln Lys Gly
                325                 330                 335

Arg Ile Ala Arg Leu Val Met Ser Ser Arg Asn Val Pro Gly Leu Phe
            340                 345                 350

Arg Thr Cys Leu Lys Leu Ala Lys Asn Phe Glu Ala Arg Cys Leu Glu
        355                 360                 365
```

-continued

Glu Thr Lys Asn Asp Pro Ser Val Ala Thr Thr Ile Lys Arg Leu Gln
370                 375                 380

Ser Ile Gln Ala Thr Cys Arg Glu Gly Leu Glu Lys Tyr Glu Thr Pro
385                 390                 395                 400

Ser Gly Leu Arg Ala Leu Cys Ala Ala Pro Ser Pro Thr Lys Met His
            405                 410                 415

<210> SEQ ID NO 39
<211> LENGTH: 423
<212> TYPE: PRT
<213> ORGANISM: Artificial Sequence
<220> FEATURE:
<223> OTHER INFORMATION: Synthetic Construct

<400> SEQUENCE: 39

Met His Met Ser Met His Gln Asp Lys Gly Val Ala Lys Asp Leu Leu
1               5                   10                  15

Arg His Pro Gly Glu Phe Pro Tyr Leu Leu Gln Leu Ala Ala Thr Thr
            20                  25                  30

Tyr Gly Thr Pro Ala Ala Pro Ile Pro Lys Glu Pro Asp Arg Ala Phe
        35                  40                  45

Cys Tyr Asn Thr Leu His Ala Val Ser Lys Gly Phe Pro Arg Phe Val
50                  55                  60

His Arg Leu Pro Leu Glu Leu Gln Asp Pro Ile Cys Ile Phe Tyr Leu
65                  70                  75                  80

Leu Leu Arg Ala Leu Asp Thr Val Glu Asp Asp Met Asn Leu Pro Ser
                85                  90                  95

Lys Val Lys Val Asp Leu Leu Arg Glu Phe His Glu His Cys Lys Asp
            100                 105                 110

Arg Asn Trp Ser Met Lys Ser Asp Tyr Gly Ile Tyr Ala Asp Leu Met
        115                 120                 125

Glu Arg Phe Pro Leu Val Ile Ser Val Leu Glu Lys Leu Pro Lys Pro
130                 135                 140

Thr Gln Glu Val Phe Val Glu Asn Val Lys Tyr Met Gly Asn Gly Met
145                 150                 155                 160

Ala Asp Phe Ile Asp Lys Glu Ile Leu Thr Val Asp Glu Tyr Asp Leu
                165                 170                 175

Tyr Cys His Tyr Val Ala Gly Ser Cys Gly Ile Ala Val Val Lys Val
            180                 185                 190

Ile Val Gln Phe Asn Leu Ala Thr Pro Glu Ala Asp Ser Met Glu Phe
        195                 200                 205

Ser Asn Ser Leu Gly Leu Leu Leu Gln Lys Ala Asn Ile Ile Thr Asp
210                 215                 220

Tyr Asn Glu Asp Ile Asn Glu Glu Pro Arg Pro Arg Met Phe Trp Pro
225                 230                 235                 240

Gln Glu Ile Trp Ala Asn Tyr Ser Glu Lys Leu Ala Asp Phe Asn Glu
                245                 250                 255

Pro Ala Asn Leu Glu Lys Ala Met Lys Cys Leu Asn His Met Val Thr
            260                 265                 270

Asp Ala Leu Arg His Ile Glu Pro Ser Leu Lys Gly Met Val Tyr Phe
        275                 280                 285

Thr Asp Gly Thr Val Phe Arg Ala Leu Ala Leu Leu Val Thr Ala
290                 295                 300

Phe Gly His Leu Ser Thr Leu Tyr Asn Asn Pro Asn Val Phe Arg Glu
305                 310                 315                 320

Lys Val Arg Gln Arg Lys Gly Arg Ile Ala Arg Leu Val Met Ser Ser

```
                    325                 330                 335
Arg Asn Val Pro Gly Leu Phe Arg Thr Cys Leu Lys Leu Ala Lys Asn
            340                 345                 350

Phe Glu Ala Arg Cys Leu Glu Glu Thr Lys Asn Asp Pro Ser Val Ala
            355                 360                 365

Thr Thr Ile Lys Arg Leu Gln Ser Ile Gln Ala Thr Cys Arg Glu Gly
370                 375                 380

Leu Glu Lys Tyr Glu Thr Pro Ser Gly Leu Arg Ala Leu Cys Ala Ala
385                 390                 395                 400

Pro Ser Pro Thr Lys Met His His His His His Val Asn Ser Leu
            405                 410                 415

Glu Ile Asp Asp Ile Arg Ala
            420

<210> SEQ ID NO 40
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(9)
<223> OTHER INFORMATION: n is a, c, g, or t

<400> SEQUENCE: 40
ccannnnnnt gg                                                             12

<210> SEQ ID NO 41
<211> LENGTH: 6
<212> TYPE: DNA
<213> ORGANISM: Artificial Sequence
<220> FEATURE:
<223> OTHER INFORMATION: Synthetic Construct

<400> SEQUENCE: 41 ctcgag                                                                     6

<210> SEQ ID NO 42
<211> LENGTH: 401
<212> TYPE: PRT
<213> ORGANISM: Botryococcus braunii

<400> SEQUENCE: 42

Met Thr Met His Gln Asp His Gly Val Met Lys Asp Leu Val Lys His
1               5                   10                  15

Pro Asn Glu Phe Pro Tyr Leu Leu Gln Leu Ala Ala Thr Tyr Gly Ser
            20                  25                  30

Pro Ala Ala Pro Ile Pro Lys Glu Pro Asp Arg Ala Phe Cys Tyr Asn
        35                  40                  45

Thr Leu His Thr Val Ser Lys Gly Phe Pro Phe Val Met Arg Leu Pro
    50                  55                  60

Gln Glu Leu Gln Asp Pro Ile Cys Ile Phe Tyr Leu Leu Arg Ala
65                  70                  75                  80

Leu Asp Thr Val Glu Asp Met Asn Leu Lys Ser Glu Thr Lys Ile
            85                  90                  95

Ser Leu Leu Arg Val Phe His Glu His Cys Ser Asp Arg Asn Trp Ser
            100                 105                 110

Met Lys Ser Asp Tyr Gly Ile Tyr Ala Asp Leu Met Glu Arg Phe Pro
        115                 120                 125
```

Leu Val Val Ser Val Leu Glu Lys Leu Pro Pro Ala Thr Gln Gln Thr
            130                 135                 140

Phe Arg Glu Asn Val Lys Tyr Met Gly Asn Gly Met Ala Asp Phe Ile
145                 150                 155                 160

Asp Lys Gln Ile Leu Thr Val Asp Glu Tyr Asp Leu Tyr Cys His Tyr
                165                 170                 175

Val Ala Gly Ser Cys Gly Ile Ala Val Thr Lys Val Ile Val Gln Phe
                180                 185                 190

Asn Leu Ala Thr Pro Glu Ala Asp Ser Tyr Asp Phe Ser Asn Ser Leu
            195                 200                 205

Gly Leu Leu Leu Gln Lys Ala Asn Ile Ile Thr Asp Tyr Asn Glu Asp
210                 215                 220

Ile Asn Glu Glu Pro Arg Pro Arg Met Phe Trp Pro Gln Glu Ile Trp
225                 230                 235                 240

Gly Lys Tyr Ala Glu Lys Leu Ala Asp Phe Asn Glu Pro Glu Asn Ile
                245                 250                 255

Asp Thr Ala Val Lys Cys Leu Asn His Met Val Thr Asp Ala Met Arg
                260                 265                 270

His Ile Glu Pro Ser Leu Lys Gly Met Val Tyr Phe Thr Asp Lys Thr
            275                 280                 285

Val Phe Arg Ala Leu Ala Leu Leu Val Thr Ala Phe Gly His Leu
290                 295                 300

Ser Thr Leu Tyr Asn Asn Pro Asn Val Phe Lys Glu Lys Val Arg Gln
305                 310                 315                 320

Arg Lys Gly Arg Ile Ala Arg Leu Val Met Ser Ser Arg Asn Val Pro
                325                 330                 335

Gly Leu Phe Arg Thr Cys Leu Lys Leu Ala Asn Asn Phe Glu Ser Arg
            340                 345                 350

Cys Lys Gln Glu Thr Ala Asn Asp Pro Thr Val Ala Met Thr Ile Lys
            355                 360                 365

Arg Leu Gln Ser Ile Gln Ala Thr Cys Arg Asp Gly Leu Ala Lys Tyr
            370                 375                 380

Asp Thr Pro Ser Gly Leu Lys Ser Phe Cys Ala Ala Pro Thr Pro Thr
385                 390                 395                 400

Lys

<210> SEQ ID NO 43
<211> LENGTH: 5763
<212> TYPE: DNA
<213> ORGANISM: Artificial Sequence
<220> FEATURE:
<223> OTHER INFORMATION: Synthetic Construct

<400> SEQUENCE: 43
gcacttttcg gggaaatgtg cgcggaaccc ctatttgttt attttttctaa atacattcaa      60 atatgtatcc gctcatgaga caataaccct gataaatgct tcaataatat tgaaaaagga     120
agagtatgag tattcaacat ttccgtgtcg cccttattcc cttttttgcg gcattttgcc     180
ttcctgtttt tgctcaccca gaaacgctgg tgaaagtaaa agatgctgaa gatcagttgg     240
gtgcacgagt gggttacatc gaactggatc tcaacagcgg taagatcctt gagagttttc     300
gccccgaaga acgttttcca atgatgagca cttttaaagt tctgctatgt ggcgcggtat     360
tatcccgtat tgacgccggg caagagcaac tcggtcgccg catacactat tctcagaatg     420
acttggttga gtactcacca gtcacagaaa agcatcttac ggatggcatg acagtaagag     480
aattatgcag tgctgccata accatgagtg ataacactgc ggccaactta cttctgacaa     540

```
cgatcggagg accgaaggag ctaaccgctt ttttgcacaa catggggat catgtaactc      600
gccttgatcg ttgggaaccg gagctgaatg aagccatacc aaacgacgag cgtgacacca      660
cgatgcctgt agcaatggca acaacgttgc gcaaactatt aactggcgaa ctacttactc      720
tagcttcccg gcaacaatta atagactgga tggaggcgga taaagttgca ggaccacttc      780
tgcgctcggc ccttccggct ggctggttta ttgctgataa atctggagcc ggtgagcgtg      840
ggtctcgcgg tatcattgca gcactggggc cagatggtaa gccctcccgt atcgtagtta      900
tctacacgac ggggagtcag gcaactatgg atgaacgaaa tagacagatc gctgagatag      960
gtgcctcact gattaagcat tggtaactgt cagaccaagt ttactcatat atactttaga     1020
ttgatttaaa acttcatttt taatttaaaa ggatctaggt gaagatcctt tttgataatc     1080
tcatgaccaa aatcccttaa cgtgagtttt cgttccactg agcgtcagac cccgtagaaa     1140
agatcaaagg atcttcttga gatcctttt ttctgcgcgt aatctgctgc ttgcaaacaa     1200
aaaaaccacc gctaccagcg gtggtttgtt tgccggatca agagctacca actctttttc     1260
cgaaggtaac tggcttcagc agagcgcaga taccaaatac tgtccttcta gtgtagccgt     1320
agttaggcca ccacttcaag aactctgtag caccgcctac atacctcgct ctgctaatcc     1380
tgttaccagt ggctgctgcc agtggcgata agtcgtgtct taccgggttg gactcaagac     1440
gatagttacc ggataaggcg cagcggtcgg gctgaacggg gggttcgtgc acacagccca     1500
gcttggagcg aacgacctac accgaactga gatacctaca gcgtgagcta tgagaaagcg     1560
ccacgcttcc cgaagggaga aaggcggaca ggtatccggt aagcggcagg gtcggaacag     1620
gagagcgcac gagggagctt ccaggggaa acgcctggta tctttatagt cctgtcgggt     1680
ttcgccacct ctgacttgag cgtcgatttt tgtgatgctc gtcagggggg cggagcctat     1740
ggaaaaacgc cagcaacgcg gccttttac ggttcctggc cttttgctgg ccttttgctc     1800
acatgttctt tcctgcgtta tcccctgatt ctgtggataa ccgtattacc gcctttgagt     1860
gagctgatac cgctcgccgc agccgaacga ccgagcgcag cgagtcagtg agcgaggaag     1920
cggaagagcg cccaatacgc aaaccgcctc tccccgcgcg ttggccgatt cattaatgca     1980
gctggcacga caggtttccc gactggaaag cgggcagtga gcgcaacgca attaatgtga     2040
gttagctcac tcattaggca ccccaggctt tacactttat gcttccggct cgtatgttgt     2100
gtggaattgt gagcggataa caatttcaca caggaaacag ctatgaccat gattacgcca     2160
agctcgaaat taaccctcac taaagggaac aaaagctgga gctctaaatg ccagaaggag     2220
cgcagccaaa ccaggatgat gtttgatggg gtatttgagc acttgcaacc cttatccgga     2280
agccccctgg cccacaaagg ctaggcgcca atgcaagcag ttcgcatgca gcccctggag     2340
cggtgccctc ctgataaacc ggccaggggg cctatgttct ttacttttt acaagagaag     2400
tcactcaaca tcttaaagcg gccgcaaaat gagtatgcac caagacaagg gggttgctaa     2460
ggatctttta aggcatccag gggaattccc ctatttgctc cagctagccg ctacaactta     2520
cggcacaccg gcggccccga tcccaaagga acccgaccga gcgttctgct ataacactct     2580
tcacgctgtt tctaaagggt tcccgaggtt tgttcacagg cttcctctgg aactccagga     2640
tccaatctgc atttttatc tcctgctgcg tgcactagat acagtggagg atgatatgaa     2700
cctcccaagt aaggtgaagg tagatctgtt gcgcgagttt catgagcatt gtaaagacag     2760
gaactggagc atgaaaagtg attatggcat ctatgcagac ttgatggaaa ggtttcctct     2820
ggtgatttcc gtcctggaaa agcttcctaa gcccacacag gaggttttg tggagaatgt     2880
caaatatatg ggcaatggca tggcagactt tattgataag gagatcttga ctgtggatga     2940
```

```
gtacgatctg tactgccact atgtggctgg tagttgtggc attgctgttg tcaaggttat    3000
tgtccaattt aaccttgcca cgccggaagc tgactcgatg gagttttcca acagcctagg    3060
attgttgctt cagaaagcca acatcattac tgactacaat gaggacatta acgaagaacc    3120
cagaccccgg atgttctggc cccaagagat ctgggccaat tactcggaaa agttagctga    3180
ctttaatgaa cccgccaacc ttgaaaaagc tatgaagtgc ttgaaccaca tggtcacaga    3240
tgccctgcgc acattgagc catctcttaa gggcatggtt tatttcacag acgggacagt     3300
cttccgcgct cttgctcttc tgctggtcac agcttttggt cacttgtcga ctttgtacaa    3360
taacccaaat gttttccgag agaaggtgag gcagcggaag ggaaggattg cccggctagt    3420
gatgtcatcc agaaacgtac caggcctctt ccgcacctgc ctaaaacttg caaagaactt    3480
tgaagccagg tgtctggagg agacaaagaa tgatccctct gtggccacaa ccatcaagcg    3540
gctgcagtca atccaggcca cgtgcagaga aggcctggaa aaatatgaga caccatctgg    3600
gctgagggcg ctctgtgctg ctccaagccc tacaaagtga cgcggccgcc ccgctccgtg    3660
taaatggagg cgctcgttga tctgagcctt gcccctgac gaacggcggt ggatggaaga     3720
tactgctctc aagtgctgaa gcggtagctt agctccccgt tcgtgctga tcagtctttt     3780
tcaacacgta aaaagcggag gagttttgca attttgttgg ttgtaacgat cctccgttga    3840
ttttggcctc tttctccatg gcgggctgg gcgtatttga agcgaattcg atatcaagct     3900
tatcgatacc gtcgacctcg agatttaaat gccagaagga gcgcagccaa accaggatga    3960
tgtttgatgg ggtatttgag cacttgcaac ccttatccgg aagcccctg cccacaaag     4020
gctaggcgcc aatgcaagca gttcgcatgc agcccctgga gcggtgccct cctgataaac    4080
cggccagggg gcctatgttc tttactttt tacaagagaa gtcactcaac atcttaaat     4140
ggccaggtga gtcgacgagc aagcccggcg gatcaggcag cgtgcttgca gatttgactt    4200
gcaacgcccg cattgtgtcg acgaaggctt ttggctcctc tgtcgctgtc tcaagcagca    4260
tctaaccctg cgtcgccgtt ccatttgca ggatggccaa gctgaccagc gccgttccgg     4320
tgctcaccgc gcgcgacgtc gccggagcgg tcgagttctg gaccgaccgg ctcgggttct    4380
cccgggactt cgtggaggac gacttcgccg gtgtggtccg ggacgacgtg accctgttca    4440
tcagcgcggt ccaggaccag gtgagtcgac gagcaagccc ggcggatcag gcagcgtgct    4500
tgcagatttg acttgcaacg cccgcattgt gtcgacgaag gcttttggct cctctgtcgc    4560
tgtctcaagc agcatctaac cctgcgtcgc cgtttccatt tgcaggacca ggtggtgccg    4620
gacaacaccc tggcctgggt gtgggtgcgc ggcctggacg agctgtacgc cgagtggtcg    4680
gaggtcgtgt ccacgaactt ccgggacgcc tccgggccgg ccatgaccga gatcggcgag    4740
cagccgtggg ggcgggagtt cgccctgcgc gaccggccg gcaactgcgt gcacttcgtg     4800
gccgaggagc aggactaacc gacgtcgacc cactctagag gatcgatccc cgctccgtgt    4860
aaatggaggc gctcgttgat ctgagccttg ccccctgacg aacggcggtg gatggaagat    4920
actgctctca gtgctgaag cggtagctta gctccccgtt cgtgctgat cagtcttttt      4980
caacacgtaa aaagcggagg agttttgcaa ttttgttggt tgtaacgatc ctccgttgat    5040
tttggcctct ttctccatgg gcgggctggg cgtatttgaa gcttaattaa ctcgaggggg    5100
ggcccggtac ccaattcgcc ctatagtgag tcgtattaca attcactggc cgtcgtttta    5160
caacgtcgtg actgggaaaa ccctggcgtt acccaactta atcgccttgc agcacatccc    5220
cctttcgcca gctggcgtaa tagcgaagag gcccgcaccg atcgcccttc ccaacagttg    5280
cgcagcctga atggcgaatg gaaattgtaa gcgttaatat tttgttaaaa ttcgcgttaa    5340
```

-continued

```
attttttgtta aatcagctca tttttttaacc aataggccga aatcggcaaa atcccttata    5400
aatcaaaaga atagaccgag atagggttga gtgttgttcc agtttggaac aagagtccac    5460
tattaaagaa cgtggactcc aacgtcaaag ggcgaaaaac cgtctatcag ggcgatggcc    5520
cactacgtga accatcaccc taatcaagtt ttttgggggtc gaggtgccgt aaagcactaa    5580
atcggaaccc taaagggagc ccccgattta gagcttgacg gggaaagccg gcgaacgtgg    5640
cgagaaagga agggaagaaa gcgaaaggag cgggcgctag ggcgctggca agtgtagcgg    5700
tcacgctgcg cgtaaccacc acacccgccg cgcttaatgc gccgctacag ggcgcgtcag    5760
gtg                                                                   5763
```

<210> SEQ ID NO 44
<211> LENGTH: 30
<212> TYPE: DNA
<213> ORGANISM: Artificial Sequence
<220> FEATURE:
<223> OTHER INFORMATION: Synthetic Construct

<400> SEQUENCE: 44
gagtacgcgg ccgccccgct ccgtgtaaat                                        30

<210> SEQ ID NO 45
<211> LENGTH: 30
<212> TYPE: DNA
<213> ORGANISM: Artificial Sequence
<220> FEATURE:
<223> OTHER INFORMATION: Synthetic Construct

<400> SEQUENCE: 45
gcactcgaat tcgcttcaaa tacgcccagc                                        30

<210> SEQ ID NO 46
<211> LENGTH: 21
<212> TYPE: DNA
<213> ORGANISM: Artificial Sequence
<220> FEATURE:
<223> OTHER INFORMATION: Synthetic Construct

<400> SEQUENCE: 46
cactaaaggg aacaaaagct g                                                 21

<210> SEQ ID NO 47
<211> LENGTH: 23
<212> TYPE: DNA
<213> ORGANISM: Artificial Sequence
<220> FEATURE:
<223> OTHER INFORMATION: Synthetic Construct

<400> SEQUENCE: 47
gcaattaacc ctcactaaag gga                                               23

<210> SEQ ID NO 48
<211> LENGTH: 30
<212> TYPE: DNA
<213> ORGANISM: Artificial Sequence
<220> FEATURE:
<223> OTHER INFORMATION: Synthetic Construct

<400> SEQUENCE: 48
gagtgcgagc tctaaatgcc agaaggagcg                                        30

<210> SEQ ID NO 49
<211> LENGTH: 27

```
<212> TYPE: DNA
<213> ORGANISM: Artificial Sequence
<220> FEATURE:
<223> OTHER INFORMATION: Synthetic Construct

<400> SEQUENCE: 49
gtcactgcgg ccgctttaag atgttga                                              27

<210> SEQ ID NO 50
<211> LENGTH: 30
<212> TYPE: DNA
<213> ORGANISM: Artificial Sequence
<220> FEATURE:
<223> OTHER INFORMATION: Synthetic Construct

<400> SEQUENCE: 50
gtcactgcgg ccgcgtcact ttgtagggct                                           30

<210> SEQ ID NO 51
<211> LENGTH: 30
<212> TYPE: DNA
<213> ORGANISM: Artificial Sequence
<220> FEATURE:
<223> OTHER INFORMATION: Synthetic Construct

<400> SEQUENCE: 51
gagtacgcgg ccgcaaaatg agtatgcacc                                           30
```

US 8,034,603 B2

NUCLEIC ACID MOLECULE

CROSS REFERENCE TO RELATED APPLICATIONS

This application claims priority from prior foreign patent Application No. 2009904482, filed Sep. 15, 2009 in Australia, and foreign patent Application No. 2009905381, filed Nov. 4, 2009 in Australia, and foreign patent Application No. 2010900782, filed Feb. 24, 2010 in Australia, all hereby incorporated by reference.

FIELD

The present invention relates to nucleic acid molecules encoding a polypeptide capable of producing a triterpenoid hydrocarbon. Additionally, the invention relates to polypeptides encoded by such nucleic acid molecules and use of such nucleic acid molecules or their encoded polypeptides in triterpenoid hydrocarbon production.

BACKGROUND

Fossil fuel is widely recognised as an unsustainable source of petroleum because of depleting supplies and the net contribution of these fuels to the carbon dioxide in the atmosphere. Renewable, carbon neutral fuels are necessary for environmental and economic sustainability. Biofuel derived from oil crops is a potential renewable and carbon neutral alternative to petroleum fuels. Currently, biofuels are produced mainly from soybeans, canola oil, animal fat, palm oil, corn oil and waste cooking oil.

Biofuel from the above sources cannot realistically satisfy even a small fraction of the existing demand for fuels. While researchers are seeking alternative feedstock for biofuel, algae have emerged as one of the most promising sources for biofuel production for three main reasons: (1) the yields of oil from algae are orders of magnitude higher than those for traditional oilseeds; (2) algae can grow in places away from the farmlands and forests, thus minimising the damages caused to ecosystems and food chain systems; and (3) algae can be grown in sewers utilising sewage and next to powerplant smokestacks where they digest pollutants and produce oil.

Algae are phototrophic cell factories, capable of deriving energy from sunlight and carbon from carbon dioxide. Algae convert carbon dioxide to potential biofuels, foods, feeds and high-value bioactives. Algae can provide several different types of renewable biofuels and valuable by-products such as antibiotics.

Not all algae are satisfactory for producing biofuel because of their low oil content or slow growth. Some species of the genus *Botryococcus* are characterised by an ability to produce high levels of hydrocarbons. For example, *Botryococcus braunii* is a unique colonial green alga that synthesises and accumulates an unusually high level of hydrocarbons up to 76% dry weight. This alga is a potentially good renewable source of useful lipids, hydrocarbons, polysaccharides, and other specialty chemicals.

The hydrocarbons produced by *Botryococcus* include (1) n-alkadienes and trienes (Race A), (2) triterpenoid botryococcenes and methylated squalenes (Race B), or (3) a tetraterpenoid, lycopadiene (Race L). Triterpenoid hydrocarbons can be used as feedstock for hydrocracking in an oil refinery to produce octane (gasoline, petrol), kerosene, and diesel, for example. Botryococcenes are preferred over alkadienes and alkatrienes for hydrocracking because botryococcenes will likely be transformed into a biofuel with a higher octane rating. It follows that use of algal lipids or hydrocarbons can greatly reduce the environmental impact associated with using coal and petroleum.

However, the production of photosynthetic fuel oils from *B. braunii* is not competitive with petroleum derived fuels. One major reason for this is the relatively slow growth rate of *B. braunii*. Furthermore, the gene(s) that causes the algae to produce botryococcene has not been identified or isolated in the art.

Disclosed in the prior art, however, is a squalene synthase (SEQ ID NO: 10) and an alleged botryococcene synthase (SEQ ID NO: 42), each derived from the Race B *B. braunii* Berkeley (Showa) strain. The alleged botryococcene synthase was not shown to produce botryococcene by molecular identification of botryococcene. Furthermore, the supporting data are consistent with the alleged botryococcene synthase having squalene synthase activity rather than botryococcene synthase activity as alleged.

Therefore, a need exists for synthetic or recombinant tools to facilitate triterpenoid hydrocarbon, particularly botryococcene, production.

SUMMARY

A first aspect provides an isolated nucleic acid molecule encoding a polypeptide capable of producing a triterpenoid hydrocarbon, wherein the polypeptide comprises at least 29 contiguous amino acid residues of any one of SEQ ID NOs: 1 to 5 or 20 to 29.

The nucleic acid molecule provides a tool for triterpenoid hydrocarbon production.

In one embodiment of the first aspect, the nucleic acid molecule comprises any one of SEQ ID NOs: 6 to 9 or 30. The nucleic acid molecule may be recombinant or synthetic.

A second aspect provides an isolated polypeptide capable of producing a triterpenoid hydrocarbon, wherein the polypeptide comprises at least 29 contiguous amino acid residues of any one of SEQ ID NOs: 1 to 5 or 20 to 29.

Particular examples of triterpenoid hydrocarbon molecules are botryococcene and squalene, which are isomers of each other and are produced from farnesyl pyrophosphate (FPP) substrate via presqualene pyrophosphate (PSPP) intermediate in *B. braunii*. Botryococcene occurs in high concentrations in Race B strains of *B. braunii*, but does not occur in Races A and L of *B. braunii*. Squalene occurs at much lower levels than botryococcene in Race B strains and occurs at low levels also in Races A and L of *B. braunii*.

The polypeptide of the second aspect may be used to synthesise a triterpenoid hydrocarbon in a cell-free system. Alternatively, the polypeptide of the second aspect may be expressed in a recombinant organism for production of a triterpenoid hydrocarbon or a botryococcene, respectively.

In one embodiment of the second aspect, the polypeptide comprises any one of SEQ ID NOs: 1 to 5 or 20 to 29. The polypeptide may be recombinant or synthetic.

The nucleic acid molecule encodes, or the polypeptide is, a botryococcene synthase, which is capable of converting FPP and/or PSPP to botryococcene. Alternatively, the nucleic acid molecule may encode, or the polypeptide may be, a squalene synthase, which is capable of converting FPP and/or PSPP to squalene.

A third aspect provides a vector, comprising the nucleic acid molecule of the first aspect.

A fourth aspect provides a recombinant non-human organism capable of producing a triterpenoid hydrocarbon, the organism comprising the nucleic acid molecule of the first aspect or the vector of the third aspect.

In another embodiment of the fourth aspect, the organism is a microorganism. The microorganism may be an alga or a bacterium. In another embodiment, the microorganism is selected from the group consisting of: *Escherichia coli; Chlamydomonas reinhardtii; Saccharomyces cerevisiae;* and *Pichia* sp.

A fifth aspect provides use of the nucleic acid molecule of the first aspect, the polypeptide of the second aspect, the vector of the third aspect, or the recombinant organism of the fourth aspect, to produce a triterpenoid hydrocarbon.

A sixth aspect provides a method for producing a triterpenoid hydrocarbon, comprising the step of growing the recombinant organism of the fourth aspect under conditions sufficient for the organism to produce a triterpenoid hydrocarbon.

A seventh aspect provides a triterpenoid hydrocarbon produced by the method of the sixth aspect. In various embodiments, the triterpenoid hydrocarbon is squalene, botryococcene, dehydrosqualene or dehydrobotryococcene.

An eighth aspect provides use of the nucleic acid molecule of the first aspect, the polypeptide of the second aspect, the vector of the third aspect, the recombinant organism of the fourth aspect, the triterpenoid hydrocarbon produced by the method of the sixth aspect, or the triterpenoid hydrocarbon of the seventh aspect, in the production of an intermediate of a biofuel, a bioplastic, a pharmaceutical, a food additive or an industrial chemical production.

A ninth aspect provides a method for producing an intermediate of a biofuel, a bioplastic, a pharmaceutical, a food additive or an industrial chemical production, comprising the steps of growing the recombinant organism of the fourth aspect under conditions sufficient for the organism to produce a triterpenoid hydrocarbon, harvesting the triterpenoid hydrocarbon from the organism, and producing the intermediate from the triterpenoid hydrocarbon.

A tenth aspect provides an intermediate produced by the method of the ninth aspect of a biofuel, a bioplastic, a pharmaceutical, a food additive or an industrial chemical, production.

In an embodiment of any one of the first to ninth aspects, the triterpenoid hydrocarbon is produced from FPP and/or PSPP.

In another embodiment of any one of the first to ninth aspects, the triterpenoid hydrocarbon is a botryococcene or a squalene.

To overcome the slow growth rate of some organisms, such as *B. braunii*, a triterpenoid hydrocarbon nucleic acid molecule, e.g. a nucleic acid molecule encoding a botryococcene synthase or a squalene synthase, may be transformed into other organisms that are faster growing, such as *C. reinhardtii, Escherichia coli, S. cerevisiae, Pichia* sp., or any other organism that is amenable to transformation and faster growth than *B. braunii*. Such synthetic or recombinant tools and recombinant organisms will facilitate the commercialisation of triterpenoid hydrocarbon production, such as for biofuel or bioplastic production. Such a recombinant organism may be used commercially in an enclosed mass growth or culture system, e.g., to provide an intermediate in or a feedstock for biofuel or bioplastic production, or to provide a source of triterpenoid hydrocarbons, such as squalene or botryococcene, for use in other processes such as chemical synthesis or cosmetic manufacture.

BRIEF DESCRIPTION OF THE FIGURES

FIGS. 1 to 5 and 20 to 28 depict the amino acid sequences encoded by exons of squalene synthase/botryococcene synthase homologues of the Ayamé 1 strain of *B. braunii*, Race B. The amino acid sequences of FIGS. 1 to 5 and 20 to 28 correspond with SEQ ID NOs: 1 to 5 and 20 to 28, respectively, and are deduced from the nucleic acid sequences provided in FIGS. 6 to 9 and 30. An asterisk represents a stop codon.

FIGS. 6 to 9 depict the nucleic acid sequences of exons of squalene synthase/botryococcene synthase homologues of the Ayamé 1 strain of *B. braunii*, Race B. Some of the figures include nucleic acid sequences of introns intervening between adjacent exons. The nucleic acid sequences of FIGS. 6 to 9 and 30 correspond with SEQ ID NOs: 6 to 9 and 30, respectively.

FIG. 10 depicts the amino acid sequence of squalene synthase of *B. braunii* Berkeley strain, Race B (accession identifications: gi|6636500; gb|AAF20201.1; AF205791_1) and corresponds with SEQ ID NO: 10.

FIG. 11 depicts the nucleic acid sequence (mRNA, complete cds; accession identifications: gi|6636499; gb|AF205791.1; AF205791) encoding the amino acid sequence of FIG. 10 and corresponds with SEQ ID NO: 11.

FIG. 12 depicts the partial amino acid sequence of squalene synthase of *B. braunii* Berkeley strain, Race B (accession identifications: gi|7532841; gb|AAF63255.1) and corresponds with SEQ ID NO: 12.

FIG. 13 depicts the nucleic acid sequence (partial cds; accession identifications: gi|7532838; gb|AH009227.1; SEG_AF205789S) encoding the amino acid sequence of FIG. 12 and corresponds with SEQ ID NO: 13.

FIG. 14 depicts the amino acid sequence of FIG. 10 against which the consensus deduced amino acid sequences of FIGS. 1 to 5 have been positioned. An asterisk represents a stop codon. The consensus sequence corresponds with SEQ ID NO: 14.

FIG. 15 illustrates the nucleic acid sequence (SEQ ID NO: 15) of the squalene synthase pSP124S construct transformed into *C. reinhardtii* in Example 11.

FIGS. 16 and 17 depict the nucleic acid sequences (corresponding with SEQ ID NO: 16 and SEQ ID NO: 17, respectively) of primer pair 1 (PP1) used to detect the presence of the squalene synthase pSP124S construct in transformed *C. reinhardtii* in Example 11.

FIGS. 18 and 19 depict the nucleic acid sequences (corresponding with SEQ ID NO: 18 and SEQ ID NO: 19, respectively) of primer pair 2 (PP2) used to detect the presence of the squalene synthase pSP124S construct in transformed *C. reinhardtii* in Example 11.

FIG. 29 depicts the amino acid sequence of ATB1, a triterpenoid hydrocarbon synthetic polypeptide of *B. braunii* Race B, Ayamé 1 strain, and corresponds with SEQ ID NO: 29. The asterisk represents the stop codon. The polypeptide comprises exons that correspond with SEQ ID NOs: 1 to 5 and 20 to 28. ATB1 does not comprise an exon 8.

FIG. 30 depicts the inferred cDNA nucleic acid sequence encoding the amino acid sequence of FIG. 29 and corresponds with SEQ ID NO: 30. The gene comprises 8 exons (labelled 1 to 7 and 9), of which exons 2, 4, 6 and 9 are underlined. The cDNA comprises exons that correspond with SEQ ID NOs: 6 to 9.

FIG. 31 depicts a genomic nucleic acid sequence encoding the amino acid sequence of FIG. 29 and corresponds with SEQ ID NO: 31.

FIG. 32 depicts a nucleic acid sequence used for cloning the ATB1 triterpenoid hydrocarbon synthetic nucleic acid sequence. The full sequence corresponds to SEQ NO: 32. The sequence, other than immediately flanking the start and stop codons, corresponds to the sequence of FIG. 30, i.e. SEQ ID NO: 30. The sequence was used to generate pUC57/ATB1, pET11a/ATB1, pET302/NT-His-ATB1, and CT-His-ATB1/pET302, referred to herein as constructs 1, 2, 3, and 4, respectively.

FIG. 33 is a photograph of an agarose gel for molecular detection of the squalene synthase pSP124S construct in transformed *C. reinhardtii* of Example 11 using the PCR primers of FIGS. 16 to 19. PCR was performed on genomic DNA extracted from individual colonies positive for Zeocin™ resistance. Lanes: 1 untransformed *C. reinhardtii* cells, PP1 negative control; 2 & 24 no cells, squalene synthase pSP124S construct, PP1 positive control; 3 plasmid pSP124S, PP1 negative control; 4, 5, 6, 7, 8, 9, 10, 11, 12, 13, transformed colonies 12, 13, 18, 24, 28, 76, 82, 87, 88, and 89 respectively, PP1; 14, 15, 16, 17, 18, 19, 20, 21, 22, 23, transformed colonies 12, 13, 18, 24, 28, 76, 82, 87, 88, and 89 respectively, PP2.

FIG. 34 is a photograph of agarose gel electrophoresis separating restriction digests of pET11a/ATB1, pET302/NT-His-ATB1, and CT-His-ATB1/pET302 (constructs 2, 3 and 4, respectively) and confirming that the expected fragment sizes are present. FIG. 34A shows that construct 2 was cut with NdeI and BstXI. FIG. 34B shows that constructs 3 and 4 were each cut with NdeI and XhoI. FIGS. 34A and B 100 bp ladder fragment sizes: 1500; 1000; 900; 800; 700; 600; 500; 400; 300; 200; 100 bp. FIG. 34A 1 kb ladder fragment sizes: 10; 8; 6; 5; 4; 3; 2.5; 2; 1.5; 1; 0.75; 0.5; 0.25 kb. FIG. 34B 1 kb ladder fragment sizes: 10; 8; 6; 5; 4; 3; 2; 1.5; 1.0; 0.5.

FIG. 35 is a photograph of an SDS-PAGE minigel of proteins of whole untransformed (U) *E. coli* and whole *E. coli* transformed (T) with construct 2 (Lanes 1 to 6) and supernatant of a cell lysate of *E. coli* transformed (T) with construct 2 (Lanes 8 and 9). *E. coli* were induced with IPTG (1 mM) for 0 h (Lanes 1 and 2), 2 h (Lanes 3 and 4) or 4 h (Lanes 5, 6, 8 and 9). Proteins were visualised with Coomassie blue dye. Arrows lane 7: molecular weight markers upper arrow 46 kDa, lower arrow 30 kDa. Arrow lane 9: soluble ATB1 protein.

FIG. 36 depicts the chemical conversion of two farnesyl pyrophosphate $C_{15}$ units to the squalene $C_{30}$ unit by the enzyme squalene synthase with NADPH cofactor (A and B) and the chemical conversion of two farnesyl pyrophosphate $C_{15}$ units to the botryococcene $C_{30}$ unit by the enzyme botryococcene synthase with NADPH cofactor (B).

FIG. 37 is a gas chromatography-mass spectrometry (GC-MS) analysis of authentic squalene.

FIG. 38 is a GC-MS analysis of authentic $C_{30}$ botryococcene.

FIG. 39 is a GC-MS analysis of heptane extracts of untransformed *E. coli* derived from Example 15.

FIG. 40 is a GC-MS analysis of heptane extracts of *E. coli* transformed with pET11a/ATB1 (construct 2) and induced with IPTG for 16 h, showing mass spectrum of generated dehydrosqualene.

FIG. 41 is a GC-MS analysis of heptane extracts of *E. coli* transformed with pET11a/ATB1 (construct 2) and induced with IPTG for 16 h, showing mass spectrum of generated squalene.

FIG. 42 is a GC-MS analysis of heptane extracts of lysates, derived from *E. coli* transformed with CT-His-ATB1/pET302 (construct 4), induced with IPTG for 2 h, then lysed and the lysate incubated for 30 min with an excess both of FPP and NADPH.

FIG. 43 depicts a nucleic acid sequence (SEQ ID NO: 33) of nucleotides inserted immediately upstream of the native start codon of the nucleotide sequence provided in FIG. 30.

FIG. 44 depicts the nucleic acid sequence of the NsiI restriction site (SEQ ID NO: 34).

FIG. 45 depicts the nucleic acid sequence of the NdeI restriction site (SEQ ID NO: 35).

FIG. 46 depicts the amino acid sequence (SEQ ID NO: 36) of the ATB1-MH polypeptide encoded by pET11a/ATB1 (construct 2), i.e. the ATB1 polypeptide of FIG. 29 (SEQ ID NO: 29) augmented consecutively with one methionine and one histidine residue at the C-terminus of ATB1. The asterisk represents the stop codon.

FIG. 47 depicts a nucleic acid sequence (SEQ ID NO: 37) of nucleotides, comprising XhoI and SmaI restriction sites, inserted immediately downstream of the native stop codon of the nucleotide sequence provided in FIG. 30.

FIG. 48 depicts the amino acid sequence (SEQ ID NO: 38) of the MHHHHHHHHMH-ATB1-MH polypeptide encoded by pET302/NT-His-ATB1 (construct 3), i.e. the ATB1 polypeptide of FIG. 29 (SEQ ID NO: 29) augmented consecutively with one methionine, eight histidine, one methionine, and one histidine residues at the N-terminus of ATB1 and augmented consecutively with one methionine and one histidine residue at the C-terminus of ATB1 (FIG. 29, SEQ ID NO: 29). The asterisk represents the stop codon.

FIG. 49 depicts the amino acid sequence (SEQ ID NO: 39) of the MH-ATB1-MH-HHHHHVNSLEIDDIRA polypeptide encoded by CT-His-ATB1/pET302 (construct 4), i.e. the ATB1 polypeptide of FIG. 29 (SEQ ID NO: 29) augmented consecutively with at its N-terminus with one histidine and one methionine residue and augmented consecutively at its N-terminus with five histidine residues and residues VNSLEIDDIRA at the C-terminus of ATB1 (FIG. 29, SEQ ID NO: 29). The asterisk represents the stop codon.

FIG. 50 depicts the nucleic acid sequence of the BstXI restriction site (SEQ ID NO: 40).

FIG. 51 depicts the nucleic acid sequence of the XhoI restriction site (SEQ ID NO: 41).

FIG. 52 depicts the amino acid sequence (SEQ ID NO: 42) provided as SEQ ID NO: 2 of US20100041120.

FIG. 53 illustrates a polypeptide sequence alignment of SEQ ID NO: 29 disclosed herein, and SEQ ID NOs: 10 and 42 disclosed previously. The boxed regions indicate Domains I, II, III, IV and V, which have been observed previously to be highly conserved amongst diverse squalene synthases. Domains III and IV have been correlated with conversion of FPP to PSPP, whereas Domains III and IV have been correlated with conversion of PSPP to squalene. SEQ ID NO: 10 comprises a hydrophobic C-terminus, which is not present in SEQ ID NOs: 29 or 42. SEQ ID NO: 29 is 87% identical to SEQ ID NO: 42 and 38% identical to SEQ ID NO: 10. SEQ ID NO: 42 is 39% identical to SEQ ID NO: 10.

FIG. 54 depicts the nucleic acid sequence of plasmid for *Chlamydomonas* Expression 3-ATB1 (pCE3-ATB1) of Example 19.

FIGS. 55 to 62 depict nucleic acid sequences of oligonucleotide primers used in Example 19.

DETAILED DESCRIPTION

Recombinant DNA technology has provided the main impetus for the rise in biotechnology since the 1980s. Currently, almost every major industrial biotechnological process is based around the use of genetically modified organisms.

Disclosed herein are synthetic and recombinant tools useful for triterpenoid hydrocarbon production. Such tools include nucleic acid molecules, polypeptides, vectors, recombinant organisms, uses and methods. Triterpenoid hydrocarbons can be used for production of biofuel, bioplastic, pharmaceuticals, food additives, industrial chemicals or specialty chemicals, for example.

Examples of use of triterpenoid hydrocarbons for manufacture of intermediates and products such as biofuel, bioplastic, pharmaceuticals (e.g. vaccine adjuvant), food additives (e.g. for cancer prevention), industrial chemicals (e.g. lubricant), specialty chemicals or cosmetics (e.g. light protection) is disclosed in Ab Gapor et al. *Palm Oil Developments* 32: 36-40; Newmark, *Cancer Epidemiology, Biomarkers & Prevention*, 1997, 6, 1101-1103; Huang et al., *Molecules* 2009, 14, 540-554; Auffray, *International Journal of Cosmetic Science*, 2007, 29, 23-29; Cox and Coulter, *Vaccine*, 1997, 15, 248-256; Fox, *Molecules* 2009, 14, 3286-3312; Schroepfer, *Ann. Rev. Biochem.*, 1981, 50, 585-621; Tran et al., *Fuel*, 2010, 89, 265-274; Catchpole et al. Ind. Eng. Chem. Res. 1997, 36, 4318-4324; He et al., *J. Agric. Food Chem.* 2002, 50, 368-372.

Exemplary triterpenoid hydrocarbon synthetic nucleic acid molecules encode a botryococcene synthase or a squalene synthase.

Whilst not wishing to be bound to any particular hypothesis, a botryococcene synthase may be advantageous when compared with a squalene synthase, since squalene synthase is subject to biosynthetic feedback inhibition, whereas it is proposed that botryococcene synthase is not subject to biosynthetic feedback inhibition. Alternatively, it is proposed that botryococcene synthase is subject to minimal or reduced biosynthetic feedback inhibition relative to biosynthetic feedback inhibition exerted upon squalene synthase. This hypothesis may account for the unusually high level of triterpenoid hydrocarbons synthesised and accumulated by *B. braunii*. It follows that although a squalene synthase may be a useful synthetic or recombinant tool for producing a triterpenoid hydrocarbon, a botryococcene synthase may be a superior synthetic or recombinant tool for producing a triterpenoid hydrocarbon.

In one embodiment of the first aspect, a nucleic acid molecule encoding a botryococcene synthase polypeptide may be isolated from Race B *B. braunii*, specifically strain Ayamé 1 (Ivory Coast). Alternatively, the Race B *B. braunii* may be selected from the group consisting of Kossou (Ivory Coast), Overuyo 3 (Bolivia), Paquemar (Martinique), La Manzo (Martinique), CCAC 0121, strain CH 28, strain CH 86, or strain 1284.

Whilst not wishing to be bound by any particular hypothesis, strains Ayamé 1 and Paquemar were considered to be high hydrocarbon-producing strains, a consideration that appeared to be confirmed in respect of Ayamé 1 by photographs showing substantial accumulation of oil deposits. Qualitatively, Ayamé 1 has been confirmed by gas chromatography to contain greater amounts of hydrocarbon than other strains. Accordingly, Ayamé 1 was selected for isolation of triterpenoid hydrocarbon nucleic acid molecules.

In another embodiment of the first aspect, a nucleic acid molecule encoding a squalene synthase polypeptide may be isolated from a Race A, a Race B or a Race L *B. braunii*. The race A *B. braunii* may be selected from the Lingoult strain (France), Overjuyo 7 strain (Bolivia), or Jillamatong strain (Australia). The race B strains may be selected from the group of strains Ayamé 1 (Ivory Coast), Kossou (Ivory Coast), Overuyo 3 (Bolivia), Paquemar (Martinique), La Manzo (Martinique), CCAC 0121, strain CH 28, strain CH 86, or strain 1284. The Race L *B. braunii* may be selected from the Madras 3 strain (India) or the Yamoussoukro 4 strain (Ivory Coast).

Alternatively, a nucleic acid molecule encoding a triterpenoid hydrocarbon synthetic polypeptide may be synthesised.

The terms "nucleic acid molecule" and "polynucleotide" are used synonymously and refer to a single or double-stranded polymer of deoxyribonucleotide or ribonucleotide bases read from the 5' to the 3' end. A nucleic acid of the present disclosure will generally contain phosphodiester bonds, although in some cases, nucleic acid analogues may be used that may have alternate backbones, comprising, e.g., phosphoramidate, phosphorothioate, phosphorodithioate, or O-methylphosphoroamidite linkages, and peptide nucleic acid backbones and linkages. Other analogue nucleic acids include those with positive backbones; non-ionic backbones, and non-ribose backbones. Thus, nucleic acid molecules or polynucleotides may also include modified nucleotides that permit correct read-through by a polymerase.

"Nucleic acid sequence" or "polynucleotide sequence" includes both the sense and antisense strands of a nucleic acid molecule as either individual single strands or in a duplex. As will be appreciated by those skilled in the art, the depiction of a single strand also defines the sequence of the complementary strand; thus the sequences described herein also provide the complement of the sequence. Unless otherwise indicated, a particular nucleic acid sequence also implicitly encompasses complementary sequences as well as the sequence explicitly indicated. The nucleic acid molecule may be DNA, both genomic and cDNA, RNA or a hybrid.

The phrase "a nucleic acid molecule encoding" refers to a nucleic acid molecule which contains sequence information for a structural RNA such as rRNA, a tRNA, or the primary amino acid sequence of a specific protein or polypeptide, or a binding site for a trans-acting regulatory agent. This phrase specifically encompasses degenerate codons (i.e., different codons which encode a single amino acid) of the native sequence or sequences that may be introduced to conform to codon preference in a specific host cell.

Letters other than A, T, C, and G when present in a nucleic acid sequence disclosed herein represent ambiguity. That is, of all the molecules sampled, there is more than one kind of nucleotide at that position. The symbols (letters) are defined as follows: A=adenine; C=cytosine; G=guanine; T=thymine; R=G A (purine); Y=T C (pyrimidine); K=G T (keto); M=A C (amino); S=G C (strong bonds); W=A T (weak bonds); B=G T C (all but A); D=G A T (all but C); H=A C T (all but G); V=G C A (all but T).

The term "gene" may be used interconvertibly with the term "nucleic acid molecule" or "nucleic acid sequence".

Nucleic acid molecules disclosed herein, e.g. encoding botryococcene synthase or squalene synthase can be expressed recombinantly in organisms, e.g., algae, cyanobacteria, photosynthetic or non-photosynthetic bacteria, fungi, including yeasts, or plant cells. As appreciated by one of skill in the art, expression constructs can be designed taking into account such properties as codon usage frequencies of the organism in which the nucleic acid molecule is to be expressed. Codon usage frequencies can be tabulated using known methods. Codon usage frequency tables, including those for algae and cyanobacteria, are also available in the art.

The term "complementary" is used herein to mean that the sequence is complementary to all or a portion of a reference polynucleotide sequence.

A "polypeptide" refers to a polymer formed from the linking, in a defined order, of amino acids by means of an amide bond. Usually, a polypeptide performs some specific function in an organism. As used herein, the term "polypeptide" includes a peptide.

As used herein, "enzyme" refers to a polypeptide that catalyses the specific conversion of a molecular substrate to a molecular product. The term "enzyme" is used herein interconvertibly with the term "polypeptide".

The term "isolated", when applied to a nucleic acid molecule or polypeptide, denotes that the nucleic acid or polypeptide is essentially free of other cellular components with which it is associated in the natural state. It is preferably in a homogeneous state and may be in either a dry or aqueous solution. Purity and homogeneity are typically determined using analytical chemistry techniques such as polyacrylamide gel electrophoresis or high pressure liquid chromatography. A polypeptide that is the predominant species present in a preparation is substantially purified. In particular, an isolated nucleic acid molecule is separated from open reading frames, which encode polypeptides other than the polypeptide of interest, that flank the gene from which the nucleic acid molecule is derived.

As used herein, an "isolated" nucleic acid molecule or polypeptide may be purified to at least about 1%, 2%, 3%, 4%, 5%, 6%, 7%, 8%, 9%, 10%, 12.5%, 15%, 17.5%, 20%, 25%, 30%, 40%, 45%, 50%, 55%, 60%, 65%, 70%, 75%, 80%, 82.5%, 85%, 87.5%, 90%, 91%, 92%, 93%, 94%, 95%, 96%, 97%, 98%, 99% or more purity by weight.

As used herein, "homologue", "homology" and "homologous" refer to nucleotide sequence similarity and amino acid sequence similarity among nucleic acid molecules and polypeptides, respectively. "Homology" may also refer to functional similarity. Homology is an indicator of ancestry or evolution.

An "orthologue" and a "paralogue" are two types of homologous sequences and are encompassed by the term "homologue". "Orthology" describes nucleotide sequences or polypeptides in different species that derive from a common ancestor. "Orthologous" nucleic acid molecules or polypeptides may or may not have the same function. "Paralogy" describes homologous nucleotide sequences or polypeptides within a single species that diverged by gene duplication.

As used herein, a "homologue" of a first nucleic acid molecule or sequence (e.g., any one of SEQ ID NOs: 6 to 9 or 30), or first polypeptide (e.g., any one of SEQ ID NOs: 1 to 5 or 20 to 29), is a second nucleic acid molecule or sequence, or second polypeptide, in the same organism type or in a different organism type, that is substantially similar to the first nucleic acid sequence or first polypeptide, in terms of its sequence. Otherwise, the "homologue" is substantially similar to the first nucleic acid molecule or first polypeptide in terms of function.

Accordingly, a triterpenoid hydrocarbon synthetic nucleic acid molecule, or the triterpenoid hydrocarbon synthetic polypeptide, includes a homologue, an orthologue or a paralogue of a nucleic acid molecule or polypeptide disclosed herein. The homologue, orthologue or paralogue corresponds with a nucleic acid molecule or polypeptide disclosed herein. The homologue, orthologue or paralogue may be a homologue, orthologue or paralogue of SEQ ID NO: 29 or SEQ ID NO: 30, but not of SEQ ID NOs: 10 to 13 or 42.

As used herein, a "triterpenoid hydrocarbon" is a compound that may be characterised by the presence of six 5-carbon isoprene (2-methyl-1,3-butadiene) units, or three 10-carbon terpene units. A "triterpenoid hydrocarbon" includes triterpenoids, methylated triterpenoids and partially cyclic triterpenoids. Particular examples of triterpenoid hydrocarbons include those synthesised by *B. braunii*. Triterpenoid hydrocarbons include botryococcenes and squalenes.

As used herein, "botryococcene" refers to a hydrocarbon compound that is produced by a living organism, and is sparingly soluble in water, but is readily soluble in organic solvents. More particularly, "botryococcene" refers to a hydrocarbon comprising isoprene units. More specifically, "botryococcene" refers to a triterpenoid hydrocarbon comprising the formula $C_nH_{2n-10}$, where n=30 to 37 ($C_{30}$ to $C_{37}$). Whilst not wishing to be bound to any particular hypothesis, triterpenoid synthesis, hence botryococcene synthesis, is dependent upon isopentenyl pyrophosphate (IPP) and dimethylallyl pyrophosphate (DMAPP) precursors. IPP and DMAPP combine to produce geranyl pyrophosphate (GPP), which then combines with IPP to produce FPP. Two molecules of FPP combine to form the intermediate molecule PSPP within the active site of the botryococcene synthase enzyme, which then forms botryococcene. Botryococcene, in particular $C_{30}$ botryococcene, which is the precursor of all higher botryococcenes ($C_{31}$ to $C_{37}$), is a triterpene resulting from head-to-head 1'-3 linkage of two FPP molecules (FIG. 36). Ultimately, botryococcene refers to any one of $C_{30}$ to $C_{37}$ hydrocarbons produced by the initial activity of a botryococcene synthase, including cyclic and acyclic botryococcenes and dehydrobotryococcenes.

As used herein, "squalene" refers to a hydrocarbon compound that is produced by a living organism, and is sparingly soluble in water, but is readily soluble in organic solvents. More particularly, "squalene" refers to a hydrocarbon comprising isoprene units. More specifically, squalene refers to a triterpenoid hydrocarbon comprising 30 carbon atoms ($C_{30}$). Triterpenoid synthesis, hence squalene synthesis, is dependent upon IPP and DMAPP precursors. IPP and DMAPP combine to produce GPP, which then combines with IPP to produce FPP. Two molecules of FPP combine to form the intermediate molecule PSPP within the active site of the squalene synthase enzyme, which then forms squalene. Squalene is a triterpene resulting from head-to-head 1'-1 linkage of two FPP molecules (FIG. 36). Ultimately, squalene refers to a $C_{30}$ hydrocarbon produced by a squalene synthase.

As used herein, a "substrate" is any compound that may be acted upon by a triterpenoid hydrocarbon synthetic polypeptide to produce a triterpenoid hydrocarbon. The substrate may itself be a terpenoid hydrocarbon. More particularly, the substrate may be FPP and/or PSPP or a precursor of FPP. The substrate, FPP and/or PSPP or precursor of FPP may be synthetic, recombinant or may be produced by an enzyme via one or more enzymes. The substrate, FPP and/or PSPP or precursor of FPP may be produced by a recombinant organism of the fourth aspect harbouring a nucleic acid molecule of the first aspect, a polypeptide of the second aspect, or a vector of the third aspect. The substrate, FPP and/or PSPP or precursor of FPP may be provided from an exogenous source to a polypeptide of the second aspect or a recombinant organism of the fourth aspect.

As stated above, triterpenoid hydrocarbon synthetic polypeptide has an enzymatic activity of catalysing the condensation of two $C_{15}$ molecules of FPP to a long-chain $C_{30}$ triterpenoid hydrocarbon, e.g. squalene or botryococcene. In addition, a triterpenoid hydrocarbon synthetic polypeptide may catalyse the condensation of two $C_{20}$ geranylgeranyl pyrophosphate (GGPP) molecules to a long-chain $C_{40}$ lycopadiene hydrocarbon.

A "triterpenoid hydrocarbon synthetic nucleic acid molecule" is a nucleic acid molecule encoding a polypeptide capable of converting a substrate to a triterpenoid hydrocarbon. In one embodiment, a "triterpenoid hydrocarbon synthetic nucleic acid molecule" comprises a nucleic acid molecule that encodes a polypeptide that comprises, or is derived from, any one of SEQ ID NOs: 1 to 5 or 20 to 29. In another embodiment, the triterpenoid hydrocarbon synthetic nucleic acid molecule comprises, or is derived from, any one of SEQ ID NOs: 6 to 9 or 30.

A "triterpenoid hydrocarbon synthetic nucleic acid molecule" may:

1) comprise a region of about 100, 150, 200, 300, 400, 500, 1000, 1500, 2000, or 5000, or more nucleotides encoding a polypeptide comprising any one of SEQ ID NOs: 1 to 5 or 20 to 29;

2) comprise a region of about 100, 150, 200, 300, 400, 500, 1000, 1500, 2000, or 5000, or more nucleotides comprising any one of SEQ ID NOs: 6 to 9 or 30;

3) under stringent conditions hybridise to a nucleic acid molecule encoding a polypeptide comprising any one of SEQ ID NOs: 1 to 5 or 20 to 29, or the complement thereof;

4) under stringent conditions hybridise to a nucleic acid molecule comprising any one of SEQ ID NOs: 6 to 9 or 30, or the complement thereof;

5) encode a polypeptide comprising at least 15 contiguous amino acids, or at least 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 100, 150, 200, 250, 300, 350, 400, 450, 500, or 550, or more contiguous residues of a polypeptide comprising any one of SEQ ID NOs: 1 to 5 or 20 to 29;

6) be amplified by primers to a nucleic acid molecule encoding a polypeptide comprising any one of SEQ ID NOs: 1 to 5 or 20 to 29;

7) is amplified by primers to a nucleic acid molecule comprising any one of SEQ ID NOs: 6 to 9 or 30.

Exons 2.1 (SEQ ID NO: 6, FIG. 6), 3.11 and 4.1 (SEQ ID NO: 7, FIG. 7), 5.3 and 6.1 (SEQ ID NO: 8, FIG. 8) and 9.2 (SEQ ID NO: 9, FIG. 9) correspond with SEQ ID NO: 30 (FIG. 30) and encode amino acids that correspond with SEQ ID NO: 29 (FIG. 29).

Exons 2.1, 4.1, 5.3, 6.1 and 9.2 encode amino acids (SEQ ID NOs: 1 to 5, FIGS. 1 to 5) that correspond with SEQ ID NO: 29 (FIG. 29).

As used herein, an "exon" refers to a nucleic acid sequence (either DNA or RNA) that is represented in the mature form of an RNA molecule after portions (introns) of a precursor RNA have been removed by splicing. The mature RNA molecule can be a messenger RNA or a functional form of a non-coding RNA such as rRNA or tRNA.

The person skilled in the art will appreciate that the amino acid translation of a nucleotide sequence encoding an exon may not provide all amino acid residues due to the presence of incomplete codons arising from splice junctions.

In all cases, a "triterpenoid hydrocarbon synthetic nucleic acid molecule" encodes a polypeptide capable of producing a triterpenoid hydrocarbon.

The term "triterpenoid hydrocarbon synthetic nucleic acid molecule" refers to a double stranded or single stranded nucleic acid molecule. The triterpenoid hydrocarbon synthetic nucleic acid molecule encodes an active or functional triterpenoid hydrocarbon synthetic polypeptide that catalyses the conversion of a substrate to a hydrocarbon.

A "triterpenoid hydrocarbon synthetic polypeptide" is an active or functional polypeptide that is capable of converting a substrate to a triterpenoid hydrocarbon.

In one embodiment, a "triterpenoid hydrocarbon synthetic polypeptide" comprises the amino acid sequence of any one of SEQ ID NOs: 1 to 5 or 20 to 29.

Thus, a triterpenoid hydrocarbon synthetic polypeptide can:

1) comprise at least 15 contiguous amino acids, or at least 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 100, 150, 200, 250, 300, 350, 400, 450, 500, 550, or more contiguous amino acids of any one of SEQ ID NOs: 1 to 5 or 20 to 29; or 2) bind to an antibody raised against an immunogen comprising a partial or full amino acid sequence of any one of SEQ ID NOs: 1 to 5 or 20 to 29.

In all cases, a "triterpenoid hydrocarbon synthetic polypeptide" is a polypeptide capable of producing a triterpenoid hydrocarbon.

A triterpenoid hydrocarbon synthetic polypeptide may be used to produce a triterpenoid hydrocarbon in a host organism. Alternatively, a triterpenoid hydrocarbon synthetic polypeptide may be used to synthesise a triterpenoid hydrocarbon, i.e. in the absence of a host cell.

Any reference herein to "botryococcene synthase" or a "botryococcene synthase polypeptide" is to a polypeptide or amino acid sequence having activity sufficient to synthesise a botryococcene, including a dehydrobotryococcene. In a particular embodiment, botryococcene synthase is capable of converting FPP and/or PSPP to botryococcene. In another embodiment, botryococcene synthase is capable of converting FPP and/or PSPP to dehydrobotryococcene, by limiting, decreasing, minimising or omitting reducing equivalents such as NADPH or NADH from the reaction system.

"Botryococcene synthase" refers to a protein that belongs to a family of prenyl transferases. Accordingly, specific motifs that are characteristic of prenyl transferases are also present in botryococcene synthase, such as, for example, an aspartate-rich region and/or a substrate-$Mg^{2+}$ binding site.

Methods for identifying amino acid residues necessary for the biochemical activity of a triterpenoid synthetic polypeptide polypeptide are described in Pandit et al., *J. Biol. Chem.*, 2000, 275, 30610-30617. Methods for altering the amino acid residues of a triterpenoid synthetic polypeptide polypeptide for structure-function analyses are described in Gu et al., *J. Biol. Chem.*, 1998, 273, 12515-12525. Numerous methods for conducting structure-function analyses of a triterpenoid synthetic polypeptide nucleic acid molecule or polypeptide are referenced in US 2010/0041120. These methods include site directed (oligonucleotide directed) mutagenesis, kits for which are commercially available. Furthermore, methods for structure-functional analyses of a triterpenoid synthetic polypeptide nucleic acid molecule or polypeptide will be known the the person skilled in the art.

If the polypeptide of the second aspect is a botryococcene synthase and the polypeptide is able to produce a squalene and a botryococcene, more botryococcene will be produced than squalene. For example, the ratio of botryococcene to squalene will be at least greater than about 1, or at least greater than about 2, 5, 10, 20, 50, 100, 200, 500, 1000, 2000, 5000, 10 000, 20 000, 50 000, 100 000, 200 000, 500 000, 1 000 000, 2 000 000, 5 000 000, 10 000 000 or more.

As used herein, "botryococcene synthase gene" refers to a nucleic acid molecule that encodes botryococcene synthase polypeptide. Thus, such a gene is often a cDNA sequence that encodes botryococcene synthase. In other embodiments, a botryococcene synthase gene may include sequences, such as introns, that are not present in a cDNA.

The term "botryococcene synthase coding region" refers to the region of the nucleic acid molecule that encodes a mature polypeptide.

A "botryococcene synthase nucleic acid molecule" is a nucleic acid molecule encoding a polypeptide capable of converting FPP and/or PSPP to botryococcene.

The term "botryococcene synthase nucleic acid molecule" refers to a double stranded or single stranded nucleic acid molecule.

Appropriate primers for identifying a botryococcene synthase gene from an organism can be generated from comparisons of the sequences provided herein.

The term "primers" refers to oligonucleotides of 10 to 100 nucleotides, which are used to amplify a gene by the polymerase chain reaction (PCR) as known by one skilled in the art.

Any reference herein to "squalene synthase" or "squalene synthase polypeptide" is to an active or functional polypeptide having activity sufficient to synthesise a squalene, including a dehydrosqualene. In a particular embodiment, squalene synthase is capable of converting FPP and/or PSPP to squalene. In another embodiment, squalene synthase is capable of converting FPP and/or PSPP to a dehydrosqualene.

A squalene synthase of the present disclosure does not encompass any one of SEQ ID NOs: 10, 12 or 42.

If a squalene synthase polypeptide is able to produce a squalene and a botryococcene, more squalene will be produced than botryococcene. For example, the ratio of squalene to botryococcene will be at least greater than about 1, or at least greater than about 2, 5, 10, 20, 50, 100, 200, 500, 1000, 2000, 5000, 10 000, 20 000, 50 000, 100 000, 200 000, 500 000, 1 000 000, 2 000 000, 5 000 000, 10 000 000 or more.

As used herein, "squalene synthase gene" refers to a nucleic acid molecule that encodes a squalene synthase polypeptide. Thus, such a gene is often a cDNA sequence that encodes squalene synthase. In other embodiments, a squalene synthase gene may include sequences, such as introns that are not present in a cDNA.

The term "squalene synthase coding region" refers to the region of the nucleic acid molecule that encodes the polypeptide.

A "squalene synthase nucleic acid molecule" is a nucleic acid molecule encoding a polypeptide capable of converting FPP and/or PSPP to squalene.

The term "squalene synthase nucleic acid molecule" refers to a double stranded or single stranded nucleic acid molecule.

Appropriate primers for identifying and characterising a squalene synthase gene from an organism can be generated from the sequences provided herein.

Because botryococcene synthase and squalene synthase are exemplary triterpenoid hydrocarbon synthetic polypeptides, a botryococcene synthase or squalene synthase nucleic acid molecule may have any of the features of a triterpenoid hydrocarbon synthetic nucleic acid molecule. Similarly, a botryococcene synthase or squalene synthase polypeptide may have any of the features of a triterpenoid hydrocarbon synthetic polypeptide.

The person skilled in the art will understand that optimal alignment of sequences for comparison may be conducted by the local homology algorithm, by the homology alignment algorithm, by the search for similarity method, by computerized implementations of these algorithms (GAP, BESTFIT, BLAST, FASTA, TFASTA, and DASH), or by inspection.

Two nucleic acid molecules or polypeptides are said to be "identical" if the sequence of nucleotides or amino acid residues, respectively, in the two sequences is the same when aligned for maximum correspondence as described below. Optionally, the percentage of sequence identity between a reference sequence and a query sequence is only considered over the length of the query sequence.

"Percentage of sequence identity" is determined by comparing two optimally aligned sequences over a comparison window, wherein the portion of the nucleic acid or amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

A "comparison window", as used herein, includes reference to a segment of any one of the number of contiguous positions, e.g., 15 or 20 to 600, usually about 50 to about 200, more usually about 100 to about 150 in which a sequence may be compared to a reference sequence of the same number of contiguous positions after the two sequences are optimally aligned.

The triterpenoid hydrocarbon synthetic nucleic acid molecule or polypeptide, e.g. botryococcene synthase or squalene synthase nucleic acid molecule or polypeptide, disclosed herein includes nucleic acid molecules and polypeptides identified and characterised by techniques such as hybridisation and/or sequence analysis using exemplary nucleic acid sequences including any one of SEQ ID NOs: 6 to 9 or 30, and exemplary polypeptide sequences including any one of SEQ ID NOs: 1 to 5 or 20 to 29.

The phrase "stringent hybridisation conditions" refers to conditions under which a probe will hybridise to its target subsequence, typically in a complex mixture of nucleic acid molecules, but to no other sequences. Stringent conditions are sequence-dependent and will be different in different circumstances. Longer sequences hybridise specifically at higher temperatures. Generally, stringent conditions are selected to be about 5-10° C. lower than the thermal melting point (Tm) for the specific sequence at a defined ionic strength pH. The Tm is the temperature (under defined ionic strength, pH, and nucleic acid molecule concentration) at which 50% of the probes complementary to the target hybridise to the target sequence at equilibrium (as the target sequences are present in excess, at Tm, 50% of the probes are occupied at equilibrium). Stringent hybridisation conditions will be those in which the salt concentration is less than about 1.0 M sodium ion, typically about 0.01 M to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent hybridisation conditions may also be achieved with the addition of destabilizing agents such as formamide. For selective or specific hybridisation, a positive signal is at least two times background, optionally 10 times background hybridisation. Exemplary stringent hybridisation conditions can be as following: 50% formamide, 5×SSC, and 1% SDS, incubating at 42° C., or 5×SSC, 1% SDS, incubating at 65° C., with wash in 0.2×SSC, and 0.1% SDS at 55° C., 60° C., or 65° C. Such washes can be performed for 5, 15, 30, 60, 120, or more minutes.

Nucleic acids that do not hybridise to each other under stringent hybridisation conditions are still substantially identical if the polypeptides that they encode are substantially identical. This occurs, for example, when a copy of a nucleic acid molecule is created using the maximum codon degeneracy permitted by the genetic code. In such cases, the nucleic acid molecule typically hybridises under moderately stringent hybridisation conditions. For example, a botryococcene synthase or squalene synthase nucleic acid molecule can also be identified by its ability to hybridise under moderately stringent hybridisation conditions (e.g., Tm ~40° C.) to nucleic acid probes having the sequence of any one of SEQ ID NOs: 6 to 9 or 30. Such a botryococcene synthase nucleic acid sequence can have, e.g., about 25-30% base pair mismatches or fewer relative to the selected nucleic acid probe. Any one of SEQ ID NOs: 6 to 9 or 30, comprises an exemplary botryococcene synthase or squalene synthase nucleic acid sequence. Exemplary "moderately stringent hybridisation conditions" include hybridisation in a buffer of 40% formamide, 1 M NaCl, 1% SDS at 37° C., and a wash in 1×SSC at 45° C. Such washes can be performed for 5, 15, 30, 60, 120, or more minutes. A positive hybridisation is at least twice background.

Those of ordinary skill in the art will readily recognise that alternative hybridisation and wash conditions can be utilized to provide conditions of similar stringency.

Appropriate probes for identifying a triterpenoid hydrocarbon synthetic gene, such as a botryococcene synthase or squalene synthase gene, from an organism can be generated from comparisons of the sequences provided herein.

Consequently, a "percentage of sequence identity" and/or hybridisation can aid identification of a homologue, an orthologue or a paralogue of a triterpenoid hydrocarbon synthetic gene or polypeptide disclosed herein.

Isolation or generation of a homologous triterpenoid hydrocarbon synthetic nucleic acid molecule, such as a botryococcene synthase or squalene synthase nucleic acid molecule, can be accomplished by a number of techniques. Cloning and expression of such technique will be addressed in the context of botryococcene synthase or squalene synthase nucleic acid molecules. For instance, oligonucleotide probes based on the sequences disclosed here can be used to identify the desired nucleic acid molecule in a cDNA or genomic DNA library from a desired species. Such a cDNA or genomic library can then be screened using a probe based upon the sequence of a cloned botryococcene synthase or squalene synthase gene, e.g., any one of SEQ ID NOs: 6 to 9 or 30. Probes may be used to hybridise with genomic DNA or cDNA sequences to isolate homologous genes in the same or different species.

Alternatively, the nucleic acid molecule of interest can be amplified from nucleic acid samples using amplification techniques. For instance, PCR may be used to amplify the sequences of the genes directly from mRNA, from cDNA, from genomic libraries or cDNA libraries. PCR and other in vitro amplification methods may also be useful, for example, to clone nucleic acid molecules that code for polypeptides to be expressed, to make nucleic acid molecules to use as probes for detecting the presence of the desired mRNA in samples, for nucleic acid sequencing, or for other purposes.

As used herein, "expression" of a triterpenoid hydrocarbon synthetic nucleic acid molecule, such as a botryococcene synthase or squalene synthase nucleic acid molecule, refers to introducing a triterpenoid hydrocarbon synthetic nucleic acid molecule, e.g. a botryococcene synthase or squalene synthase nucleic acid molecule, into a cell, e.g., algae, such as green algae, cyanobacteria, photosynthetic or non-photosynthetic bacteria, fungi, including yeasts, or a plant, in which it is not normally expressed. Accordingly, an "increase" in triterpenoid hydrocarbon synthetic activity or expression is generally determined relative to wild type cells, e.g., algae, cyanobacteria, photosynthetic or non-photosynthetic bacteria, fungi, including yeasts, or plants that have no, or low, triterpenoid hydrocarbon synthetic activity.

"Increased" or "enhanced" activity or expression of a triterpenoid hydrocarbon synthetic nucleic acid molecule or polypeptide, e.g. a botryococcene synthase or squalene synthase nucleic acid molecule or polypeptide, refers to a change in triterpenoid hydrocarbon synthetic activity or expression, e.g. botryococcene synthase or squalene synthase activity or expression. Examples of such increased activity or expression include the following: botryococcene synthase expression or activity or squalene synthase expression or activity of a botryococcene synthase nucleic acid molecule or polypeptide or squalene synthase nucleic acid molecule or polypeptide is increased above the level of that in the wild-type, non-transgenic control organism (i.e., the quantity of botryococcene synthase or squalene synthase activity, or expression of botryococcene synthase or squalene synthase nucleic acid molecule, is increased); botryococcene synthase or squalene synthase activity, or expression of a botryococcene synthase or squalene synthase nucleic acid molecule, is in a cell where it is not easily detected in wild-type, non-transgenic cells (i.e., expression of the botryococcene synthase or squalene synthase protein is increased, as is its activity); botryococcene synthase or squalene synthase activity, or botryococcene synthase or squalene synthase nucleic acid molecule expression, is also increased when botryococcene synthase or squalene synthase activity or expression of the botryococcene synthase or squalene synthase nucleic acid molecule is present in a cell for a longer period than in a wild-type, non-recombinant control (i.e., duration of botryococcene synthase or squalene synthase activity, or expression of the botryococcene synthase or squalene synthase protein is increased).

The activity or expression of a triterpenoid hydrocarbon synthetic nucleic acid molecule or polypeptide, or the production of a triterpenoid hydrocarbon, is considered to be "increased" or "enhanced" if the activity, expression or production is at least about 1%, 2%, 3%, 4%, 5%, 6%, 7%, 8%, 9%, 10%, 12.5%, 15%, 17.5%, 20%, 25%, 30%, 40%, 45%, 50%, 55%, 60%, 65%, 70%, 75%, 80%, 82.5%, 85%, 87.5%, 90%, 91%, 92%, 93%, 94%, 95%, 96%, 97%, 98%, 99%, 100% or more, for example at least about 2-, 3-, 4-, 5-, 6-, 7-, 8-, 9-, 10-, 20-, 50-, 100-fold or more, compared with an organism lacking a triterpenoid hydrocarbon synthetic gene or polypeptide, or compared with an organism comprising a wild-type or endogenous triterpenoid hydrocarbon synthetic gene or polypeptide, or in a cell-free system compared to another putative or homologous triterpenoid hydrocarbon synthetic polypeptide.

A "vector" as used herein refers to any vehicle used to transfer genetic material, particularly to transfer exogenous genetic material into a cell.

An "expression vector" refers to a nucleic acid construct, which when introduced into a host cell, results in transcription and/or translation of a RNA or polypeptide, respectively.

The introduction of polynucleotide sequences can be either temporary, e.g. by use of vectors, or permanent, e.g. by integration of the entire vector or a fragment thereof into either the nuclear genome, the plastid genome, or the mitochondrial genome of the host alga.

Suitable vectors for increasing expression of the polynucleotide sequence that encodes the desired polypeptide sequence in an algal cell are known in the art, such as the expression vectors described in U.S. Pat. No. 7,232,679. Such vectors for increasing expression of the polynucleotide sequence are incorporated herein by reference. For example, suitable vectors include pBBR-K-mev-opl6-I, pBBR-K-mev-opl6-2, pDS-mvaA, pDS-idi, pDS-hcs, pDS-mvk, pDS-pmk, pDS-mvd, pDS-His-mvaA, pDS-His-idi, pDS-His-hcs, pDS-His-mvk, pDS-His-pmk, pDS-His-mvd, pBBR-K-Zea4, pBBR-K-Zea4-up, pBBR-K-Zea4-down, pBBR-K-PcrtE-crtE-3, pBBR-tK-PcrtE-mvaA, pBBR-tK-PcrtE-idi, pBBR-tK-PcrtE-hcs, pBBR-tK-PcrtE-mvk, pBBR-tK-PcrtE-pmk, pBBR-tK-PcrtE-mvd, pBBR-K-PcrtE-mvaA-crtE-3, pDS-His-phaA, pBBR-K-PcrtE-crtW, pBBR-K-PcrtE-crtWZ, pBBR-K-PcrtE-crtZW, and combinations thereof.

A vector comprising a triterpenoid hydrocarbon synthetic nucleic acid molecule, e.g. botryococcene synthase nucleic acid molecule or squalene synthase nucleic acid molecule, may comprise a marker gene that confers a selectable phenotype on algae, plant or bacterial cells. For example, the marker may encode antibiotic resistance, such as resistance to kanamycin, G418, phleomycin (Zeocin™), bleomycin, hygromycin, and the like. In one embodiment, a selectable marker for use in *Chlamydomonas* can be a marker that provides spectinomycin resistance, kanamycin and amikacin resistance, zeomycin, bleomycin or phleomycin (Zeocin™) resistance, paramomycin, or neomycin resistance.

Selectable markers for host organisms are well known in the art.

A "regulatory element" includes a promoter, which may be either constitutive or inducible. In one embodiment, a promoter can be used to direct expression of botryococcene synthase nucleic acid molecules under the influence of changing environmental conditions. Examples of environmental conditions that may effect transcription via an inducible promoter include anaerobic conditions, elevated temperature, or the presence of light. Promoters that are inducible upon exposure to chemical reagents may also be used to express a triterpenoid hydrocarbon synthetic nucleic acid molecule, e.g. a botryococcene synthase or a squalene synthase nucleic acid molecule.

Other useful inducible regulatory elements include copper-inducible regulatory elements, tetracycline and chlor-tetracycline-inducible regulatory elements, ecdysone inducible regulatory elements, heat shock inducible regulatory elements, and lac operon elements, which are used in combination with a constitutively expressed lac repressor to confer, for example, IPTG-inducible expression. An inducible regulatory element also can be, for example, a nitrate-inducible promoter, e.g., derived from the spinach nitrite reductase gene, or a light-inducible promoter, such as that associated with the small subunit of RuBP carboxylase or the LHCP gene families, or a light.

The term "promoter" or "regulatory element" refers to a region or sequence determinants located upstream or downstream from the start of transcription that direct transcription. As used herein, a promoter includes necessary nucleic acid sequences near the start site of transcription, such as, in the case of a polymerase II type promoter, a TATA element. A promoter also optionally includes distal elements, which can be located as much as several thousand base pairs from the start site of transcription.

A "constitutive" promoter is a promoter that is active under most environmental and developmental conditions.

An "inducible" promoter is a promoter that is active under environmental or developmental regulation.

The term "operably linked" refers to a functional linkage between a nucleic acid expression control sequence (such as a promoter) and a second nucleic acid sequence, such as a botryococcene synthase or squalene synthase gene, wherein the expression control sequence directs transcription of the nucleic acid molecule corresponding to the second sequence.

An "algae promoter", "bacterial promoter", "fungal promoter", "yeast promoter" or "plant promoter" is a promoter capable of initiating transcription in algae, bacteria, fungi, including yeasts, and/or plant cells, respectively. Such a promoter is therefore active in algae, cyanobacteria, bacterial, or plant cells, but need not originate from that organism. It is understood that limited modifications can be made without destroying the biological function of a regulatory element and that such limited modifications can result in regulatory elements that have substantially equivalent or enhanced function as compared to a wild type regulatory element. These modifications can be deliberate, as through site-directed mutagenesis, or can be accidental such as through mutation in hosts harbouring the regulatory element. All such modified nucleotide sequences are included in the definition of a regulatory element as long as the ability to confer expression is substantially retained.

In one example, a promoter sequence that is responsive to light may be used to drive expression of a botryococcene synthase nucleic acid construct that is introduced into *Chlamydomonas* that is exposed to light. Other light-inducible promoter systems may also be used, such as the phytochrome/PIF3 system. Further, a promoter can be used that is also responsive to heat can be employed to drive expression in algae such as *Chlamydomonas*. Additional promoters, e.g., for expression in algae such as green algae, include the RbcS2 and PsaD promoters.

In one embodiment, the promoter may be from a gene associated with photosynthesis in the species to be transformed or another species. For example such a promoter from one species may be used to direct expression of a protein in transformed algal cells or cells of another photosynthetic marine organism. Suitable promoters may be isolated from or synthesized based on known sequences from other photosynthetic organisms. Preferred promoters are those for genes from other photosynthetic species that are homologous to the photosynthetic genes of the algal host to be transformed. For example, a series of light harvesting promoters from the fucoxanthin chlorophyll binding protein have been identified in *Phaeodactylum tricornutum*. In other embodiments, a carotenoid chlorophyll binding protein promoter, such as that of peridinin chlorophyll binding protein, can be used.

In one embodiment, a promoter used to drive expression of a heterologous triterpenoid hydrocarbon synthetic nucleic acid molecule, e.g. a botryococcene synthase or squalene synthase nucleic acid molecule, is a constitutive promoter. Examples of constitutive strong promoters for use in algae include, e.g., the promoters of the atpA, atpB, and rbcL genes. Various promoters that are active in cyanobacteria are also known. These include promoters such as the (constitutive) promoter of the psbA3 gene in cyanobacteria. Other promoters that are operative in plants, e.g., promoters derived from plant viruses, such as the CaMV35S promoters, can also be employed in algae.

Promoter sequences for an algal cell are preferably isolated from an algal species or a closely related organism. Promoters that are functional in higher plants are less preferred except for groups of algae closely related to higher plants. For example, the 35S CaMV promoter, which is active in many plant species, is completely inactive in *Chlamydomonas* (Day et al. (1990) Physiol. Plantarum 78:254-260).

Examples of suitable promoters include hydrogenase promoters, Cytochrome C6 (Cyc6) promoter, Nia1 promoter, Cabll-1 promoter, Ca1 promoter, Ca2 promoter, coprogen oxidase promoter, algal ribulose bisphosphate carboxylase small subunit gene (SSU) promoter, and algal pyruvate kinase promoter. Additional suitable promoters include the arylsulfatase promoter, and the aminoglycoside 3'-phosphotransferase gene (aph VIII) promoter from the multicellular green alga Volvox, and RbcS2 promoter which has been widely used to drive gene expression in the nucleus of *C. reinhardtii*.

Another suitable promoter for use in *C. reinhardtii* is the Hsp70A-RbcS2 hybrid promoter (e.g. in pBC1 and other plasmids) as disclosed in Schroda et al. *The Plant Journal*, 2000, 21, 121-131 and Schroda et al., *The Plant Journal*, 2002, 31, 445-455.

In one embodiment, promoters are identified by analysing the 5' sequences of a genomic clone corresponding to a triterpenoid hydrocarbon synthetic gene, e.g. a botryococcene synthase or squalene synthase gene. Sequences characteristic of promoter sequences can be used to identify the promoter.

A promoter can be evaluated, e.g., by testing the ability of the promoter to drive expression in plant cells, e.g., green algae, in which it is desirable to introduce a triterpenoid hydrocarbon synthetic construct, such as a botryococcene synthase or squalene synthase expression construct.

Examples of suitable regulatory elements, e.g. enhancer elements, include: EE-1 and EE-2 described in Kucho et al. (*Plant Physiol* 2003, 133(2):783-93); the GCC-box enhancer element described in Wu et al. (*Mol Genet Genomics* 2001, 265(5):763-70); and those described in Fischer, et al. (*Mol Genet Genomics* 2001, 265(5):888-94) regarding flanking regions of PsaD.

Enhancer elements suitable for transgene expression in *C. reinhardtii* are also described in Lumbreras et al., *The Plant Journal*, 1998, 14, 441-447 and Colombo et al., *Funct. Plant Biol.*, 2002, 29, 231-241.

"*Botryococcus braunii*" or "*B. braunii*" refers to a colonial green alga of the order Chlorococcales (class Chlorophyceae). Certain strains of *B. braunii* synthesise and accumulate an unusually high level of lipids or triterpenoid hydrocarbons that are typically around 30-40 percent, or more, of their dry weight.

As used herein, "strain" refers to an organism belonging to the same species, but displaying at least one different characteristic compared with a second organism of the same species. The different characteristic can be caused by differences in the genomes of the strains under comparison. Thus, a recombinant organism is also a "strain" of the host organism. Specific types of strains are referred to herein as "races". "Race A" refers to strains of *B. braunii* whose major lipid hydrocarbon is "alkadiene" and "alkatriene" (derivatives of fatty acids) having the formula $C_nH_{2n-10}$, wherein n is an odd number 23 to 31. "Race B" refers to strains of *B. braunii* whose major lipid hydrocarbon is "botryococcene". "Race L" refers to strains of *B. braunii* whose major lipid hydrocarbon is "lycopadiene".

As used herein, "organism" refers to an individual living system.

A "host organism" refers to a first organism that comprises exogenous DNA or RNA, or a polypeptide, which is derived from a second organism other than the first organism.

The host organism is a "non-human" organism, which excludes vertebrate organisms.

The host organism may be a a single cell organism, a filamentous organism, a higher plant or a macroalgae such as a seaweed, for example Pacific giant kelp. Pacific giant kelp is a species of marine alga found on the Pacific coast of North and Central America. It begins life as a microscopic spore, but may grow up to 60 m with the upper fronds forming a dense canopy at the surface. Kelp fronds may grow at 300 mm to 600 mm per day which makes it ideal to produce large amounts of triterpenoid hydrocarbons in a short period of time. See, for example, Copping, et al., 2008, Techno-Economic Feasibility Analysis of Offshore Seaweed Farming for Bioenergy and Biobased products, Independent Research and Development Report, Battelle Pacific Northwest Division, incorporated herein by reference.

In a particular embodiment, the host organism is a microorganism.

As used herein, "microorganism" refers to microalgae, bacteria, fungi, including yeast, cyanobacteria, diatoms, photosynthetic bacteria or non-photosynthetic bacteria, or Euglenids.

In one embodiment, an alga is used. "Alga", "algae", "microalga", "microalgae" or the like, refer to plants belonging to the subphylum Algae of the phylum *Thallophyta*. The algae are unicellular, photosynthetic, oxygenic algae and are non-parasitic plants without roots, stems or leaves; they contain chlorophyll and have a great variety in size, from microscopic to large seaweeds. Green algae, which are single cell eukaryotic organisms of oxygenic photosynthesis, endowed with chlorophyll a and chlorophyll b, belonging to Eukaryota-Viridiplantae-Chlorophyta-Chlorophyceae, may be used. However, algae may also be blue-green, red, or brown, so long as the algae are able to host a nucleic acid molecule of the first aspect or a vector of the third aspect to produce a triterpenoid hydrocarbon such as botryococcene or squalene.

In one embodiment, a green alga, cyanobacterium (blue-green algae), or a diatom is used. Examples of green algae include: *Botryococcus* sp. other than that from which botryococcene synthase was isolated, such as *B. braunii* Race A or Race L, or *Botryococcus sudeticus*; *Chlamydomonas* sp., e.g. *C. reinhardtii*, which is classified as Volvocales-Chlamydomonadaceae; *Chlorella* sp., e.g. *Chlorella vulgaris* or NC64A; *Scenedesmus obliquus*; *Dunaliella salina*; or *Haematococcus pluvialis*. Other examples include *Choricystis* sp., e.g. *Ch. minor* and *Ch. chodatii*. Examples of cyanobacteria include: *Microcystis* sp.; *Synechocystis* sp.; or *Spirulina platensis*. *Navicula tennerima* is an example of a diatom species that may be used.

Alternatively, the alga may be *Volvox carteri*, *Ostreococcus tauri*, *Ostreococcus lucimarinus*, *Thalassiosira pseudonana*, *Pheodactylum tricornutum*, or *Aureococcus anophagefferens*.

In another embodiment, a euglanid may be used, e.g. *Euglena* sp.

In yet another embodiment, a bacterium may be used. The bacterium may be photosynthetic, e.g. *Rhodospirillum rubrum*, or non-photosynthetic, e.g. *E. coli*.

In an alternative embodiment, another photosynthetic organism may be used, e.g. a plant cell. Plant cells that may be suitable include those of *Nicotiana tobaccum* or *Arabidopsis thaliana*.

In one embodiment, a fungus may be used. For example, a yeast may be used, e.g. *S. cerevisiae* or *Pichia* sp.

As used herein, "recombinant organism" or "transgenic organism" refers to a second organism, or "host organism", that harbours genetic material derived from a first, or donor, source. "Recombinant organism" refers to any organism, such as an alga, bacterium, fungus, including a yeast, or plant, in which an exogenous nucleic acid molecule is expressed. More specifically, the term refers to any transformed alga, bacterium, fungus, including a yeast, or plant that displays the desired characteristics of both the donor and host organisms. The desired characteristic of the donor organism is a triterpenoid hydrocarbon synthetic nucleic acid molecule, e.g. a botryococcene synthase or squalene synthase nucleic acid molecule, or the desired characteristic is a triterpenoid hydrocarbon synthetic polypeptide, e.g. a botryococcene synthase or a squalene synthase polypeptide, either of which contributes in the host organism to high triterpenoid hydrocarbon content similar to the donor organism. The desired characteristics of the host organism include stability and/or fast growth. Therefore, a "recombinant organism" will synthesise levels of triterpenoid hydrocarbon in excess of the host organism and more similar to those of the donor strain. A desired "recombinant organism" will also be more stable and/or grow faster than the donor organism.

As used herein, "recombinant" describes a second, or host species of genetic material that harbours genetic material derived from a first, or donor, source. Thus, the host harbours exogenous genetic material, e.g. DNA or RNA. "Recombinant" is used interchangeably with "genetically manipulated" or "transgenic".

As used herein, "genetic manipulation" or "molecular biotechnology" refers to any human-exerted artificial process that is performed on DNA or RNA, including, but not limited to, disruption, isolation, replication, modification and introduction into a different organism. An organism that has undergone genetic manipulation is also referred to herein as "recombinant".

As used herein, "exogenous" refers to a molecule, e.g. DNA, RNA or compound, originating externally to an organism. With respect to DNA or RNA, the term can be used interchangeably with "heterologous".

Conversely, as used herein, "endogenous" refers to a molecule, e.g. DNA, RNA or compound, originating within an organism.

The term "heterologous" refers to a host, e.g. a strain, species, or genus, not normally possessing a gene that is transformed into the host, or refers to a gene not normally present in a host, e.g. a strain, species, or genus, artificially endowed with the gene. The term "heterologous" is used interconvertibly with the term "exogenous", in the case of an exogenous gene.

A nucleic acid molecule is "heterologous to" a second nucleic acid molecule if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

This disclosure contemplates a recombinant organism or a host organism further transformed with a nucleic acid molecule or vector encoding, in addition to the triterpenoid hydrocarbon synthetic polypeptide, a polypeptide useful in synthesis of a triterpenoid hydrocarbon such as a botryococcene. For example, the recombinant organism may also comprise an FPP synthase or a methyltransferase such as a botryococcene methyltransferase or a squalene methyltransferase.

As used herein, "transform", and variations thereof, refers to the process of introducing exogenous DNA or RNA from a donor organism into a host organism. The term is not used in a limiting sense and includes any mechanism by which foreign DNA can be introduced into a host organism. Thus, "transform" includes, but is not limited to, electroporation, transfection, gene guns, viral methods, and glass beads methods for example. The term "transformed" essentially unites a gene and organism not previously containing that gene, and refers to the artificial conjunction of the organism and the gene by genetic modification of the organism by a human being, using processes other than sexual conjugation of organisms. After transformation, function of the gene may or may not occur in the new organism.

In algae, the nuclear, mitochondrial, and chloroplast genomes are transformed through a variety of known methods, including by microparticle bombardment (e.g. DNA-coated gold particles), or using a glass bead method.

In one embodiment, a triterpenoid hydrocarbon synthetic nucleic acid molecule, e.g. a botryococcene synthase or squalene synthase nucleic acid molecule, is introduced into and/or targeted to the chloroplast of an alga. In another embodiment, a triterpenoid hydrocarbon synthetic nucleic acid molecule, e.g. a botryococcene synthase or squalene synthase nucleic acid molecule, is introduced into and/or targeted to the nucleus.

To use isolated sequences in the above techniques, synthetic or recombinant DNA vectors suitable for transformation of green algae, other eukaryotic algae, cyanobacteria, photosynthetic or non-photosynthetic bacteria, fungi, including yeasts, or plant cells are prepared.

Techniques for transformation are well known in the art and described in the technical and scientific literature. For example, a DNA sequence encoding a triterpenoid hydrocarbon synthetic nucleic acid molecule, e.g. a botryococcene synthase or squalene synthase nucleic acid molecule, can be combined with transcriptional and other regulatory sequences which will direct the transcription of the nucleic acid molecule in the intended cells of the transformed alga, cyanobacterium, bacterium, fungus, including a yeast, or plant. In one embodiment, an expression vector that comprises the botryococcene synthase or squalene synthase nucleic acid molecule further comprises a promoter operably linked to the botryococcene synthase or squalene synthase nucleic acid molecule. In other embodiments, a promoter and/or other regulatory elements that direct transcription of the botryococcene synthase or squalene synthase nucleic acid molecule are endogenous to the organism and the vector comprising the botryococcene synthase or squalene synthase nucleic acid molecule is introduced, e.g., by homologous recombination, such that the heterologous botryococcene synthase or squalene synthase nucleic acid molecule is operably linked to an endogenous promoter and expression is driven by the endogenous promoter.

The present disclosure employs various routine synthetic or recombinant nucleic acid techniques. Generally, the nomenclature and the laboratory procedures in synthetic or recombinant DNA technology described are those well known and commonly employed in the art.

As used herein, "biofuel" refers to fuel derived from carbon sources that can be replenished and make reduced, minimal or no net contribution to atmospheric carbon dioxide levels. More specifically, biofuel refers to carbon sources derived from an organism that expresses a triterpenoid hydrocarbon synthetic gene, and the lipid or hydrocarbon can be used as fuel or to produce fuel. To produce biofuel, it may be necessary for hydrolytic cracking or hydrocracking of the triterpenoid hydrocarbon. Biofuel is distinct from traditional "fossil" fuels.

A triterpenoid hydrocarbon produced according to this disclosure may be combusted directly as a fuel. However for performance in internal combustion engines, the triterpenoid hydrocarbon should be modified by processes such as pyrolysis and catalytic cracking. Crude triterpenoid hydrocarbons can be converted to petrol (gasoline), light cycle oil, heavy cycle oil, and coke by catalytic cracking as has been taught by Kitazato et al., Sekiyu Gakkaishi 32:28. The yields of petrol (gasoline) obtained by catalytic cracking of algal hydrocarbons are comparable to yields obtained from petroleum. Also the gasoline produced has sufficiently high octane numbers for direct use in transportation vehicles. Aviation fuel may also be obtained using processes known in the art.

Similarly, "bioplastic" refers to plastic derived from carbon sources that can be replenished and make minimal or no net contribution to atmospheric carbon dioxide levels. More specifically, bioplastic refers to carbon sources derived from an organism that expresses a triterpenoid hydrocarbon synthetic gene, and the triterpenoid hydrocarbon can be used to produce plastic.

The disclosure contemplates application to any product traditionally derived from petrochemical sources of fossil fuels to which the triterpenoid hydrocarbon is amenable. For example, in addition to biofuel and bioplastic, it is envisaged that the disclosure will be useful for, but not limited to, production of pharmaceuticals, food additives, industrial chemicals, specialty chemicals, detergents, fertilizers, medicines, paints, plastics, synthetic fibres, or synthetic rubber.

In an embodiment of the method of the sixth aspect, the triterpenoid hydrocarbon is squalene or botryococcene and the conditions comprise supplementing the recombinant organism with NADPH or NADH. In another embodiment, the triterpenoid hydrocarbon is dehydrosqualene or dehydrobotryococcene and the conditions comprise not supplementing the recombinant organism with, or minimising the concentration of, NADPH or NADH. By limiting, decreasing, minimising or omitting reducing equivalents such as NADPH or NADH in the reaction system, the method provides for the production of a dehydrosqualene or a dehydrobotryococcene, which each lack at least two hydrogen atoms when compared with squalene or botryococcene, respectively. Dehydrosqualene and/or dehydrobotryococcene can be identified using GC-MS.

A triterpenoid hydrocarbon synthetic nucleic acid molecule, e.g. botryococcene synthase or squalene synthase nucleic acid molecule, can be expressed in any number of algae, e.g., green algae, other eukaryotic algae, cyanobacteria, or photosynthetic or non-photosynthetic bacteria, fungi, including yeasts, or plant cells where it is desirable to produce a triterpenoid hydrocarbon, e.g. botryococcene or squalene. Transformed algae, cyanobacteria, bacteria (photosynthetic bacteria or non-photosynthetic bacteria), or fungi, including yeasts, that express a heterologous triterpenoid hydrocarbon synthetic nucleic acid molecule, e.g. botryococcene synthase or squalene synthase nucleic acid molecule, may be grown under mass culture conditions for the production of the triterpenoid hydrocarbon, e.g. botryococcene or squalene. The transformed or recombinant organisms are grown in bioreactors or fermentors that provide an enclosed environment to contain the triterpenoid hydrocarbon, e.g. botryococcene or squalene. In certain embodiments for mass culture, the algae, cyanobacteria, bacteria, or fungi, including yeasts, are grown in enclosed reactors in quantities of at least about 100 litres, 200 litres, 500 litres, at least about 1000 litres, 2000 litres, 5000 litres, 10,000 litres, 20,000 litres, 50,000 litres, 100,000 litres, 200,000 litres, 500,000 litres or greater, and in one embodiment, in quantities of about 1,000,000 litres or more, even 1,500,000 litres, or more.

As used herein, "mass-culturing" refers to growing large quantities of algae, cyanobacteria, photosynthetic or non-photosynthetic bacteria, or fungi, including yeasts, that have been modified to express a triterpenoid hydrocarbon synthetic nucleic acid molecule, e.g. botryococcene synthase or squalene synthase. A "large quantity" is generally in the range of about 10 litres or more, 20 litres, 50 litres, or about 100 litres to about 1,500,000 litres, for example, 200 litres, 500 litres, 1000 litres, 2000 litres, 5000 litres, 10,000 litres, 20,000 litres, 50,000 litres, 100,000 litres, 200,000 litres, 500,000 litres, 1,000,000 litres, even 1,500,000 litres, or more. In one embodiment, the organism may be cultured in large quantities in modular bioreactors, each having a capacity of about 1,000 to about 1,000,000 litres, for example, 200 litres, 500 litres, 1000 litres, 2000 litres, 5000 litres, 10,000 litres, 20,000 litres, 50,000 litres, 100,000 litres, 200,000 litres, or 500,000 litres. In one embodiment, a recombinant plant may be amenable to mass culture.

A "bioreactor" refers to any enclosed large-capacity vessel in which microalgae, cyanobacteria or photosynthetic or non-photosynthetic bacteria, or fungi, including yeasts, are grown. A "large-capacity vessel" can hold about 10 litres, or about 500 litres to about 1,000,000 litres, or more, for example, 20 litres, 50 litres, 100 litres, 200 litres, 500 litres, 1000 litres, 2000 litres, 5000 litres, 10,000 litres, 20,000 litres, 50,000 litres, 100,000 litres, 200,000 litres, or 500,000 litres, or more.

Methods of mass-culturing algae are known. For example, algae can be grown in high density photobioreactors, bioreactors such as those for sewage and waste water treatments, mass-cultured for the elimination of heavy metals from contaminated water, mass-cultured for the production of β-carotene, hydrogen, and pharmaceutical compounds, as well as nutritional supplements for both humans and animals and for the production of other compounds of nutritional value.

Conditions for growing triterpenoid hydrocarbon-expressing algae, cyanobacteria, photosynthetic or non-photosynthetic bacteria, or fungi, including yeasts, e.g. botryococcene synthase-expressing or squalene synthase-expressing algae or bacteria, are known in the art. For example, methods for growing *Botryococcus* are disclosed in WO 2006/121950.

Alternatively, a triterpenoid hydrocarbon may be produced in a cell-free system. Examples of cell-free systems are disclosed herein at Example 10 and Example 16, and in US 2010/0041120, Okada et al. *Arch Biochem Biophys* 2000, 373(2): 307-317, and Okada et al. *Arch Biochem Biophys* 2004, 422: 110-118, which are incoporated herein by reference.

Triterpenoid hydrocarbon, e.g. botryococcene or squalene, produced by the genetically modified organisms disclosed herein is not currently known in the art, but could be harvested using known techniques. As used herein, to "harvest" a triterpenoid hydrocarbon, e.g. botryococcene or squalene, refers to capturing and sequestering the triterpenoid hydrocarbon, e.g. botryococcene or squalene, in a closed or contained environment.

Harvesting may include flocculating the microorganism, e.g. alga, by adjusting the pH of the medium in with the organism resides. Botryococcenes and squalene are not miscible in water and they may rise to and float at the surface of the growth medium if released by the organism. If so, they may be siphoned off from the surface and sequestered in suitable containers.

Alternatively, destructive harvesting of the triterpenoid hydrocarbon, e.g. botryococcene or squalene, from the recombinant organism, such as algae (including seaweed) or bacteria, may be required, for example pressing, solvent extraction or supercritical fluid extraction. Under suitable conditions, 70% of hydrocarbons can be released by contact with hexane for 30 minutes. Hydrocarbons can be continuously extracted with proper agitation and recovery methodologies known in the art. Supercritical fluids such as carbon dioxide ($CO_2$) allow rapid extraction of hydrocarbons, and are nontoxic, inexpensive, easily separated from the extracted hydrocarbons and are reusable.

Also disclosed herein is a business method comprising providing a carbon credit to a party growing a genetically modified organism, comprising a nucleic acid molecule according to the first aspect, adapted to produce a biofuel, a pharmaceutical, a food additive, an industrial chemical, a specialty chemical, a detergent, a fertilizer, a medicine, a paint, a plastic, a synthetic fibre, or a synthetic rubber. As such, the methods and compositions described herein may be used in a business method in exchange for carbon credits.

Carbon credits may be an allowance, permit, credit, or the like which are or have been allowed, authorised, or recognised by some relevant sovereign entity (such as, but not limited to, a city (including municipalities of all sizes and types including both incorporated and unincorporated municipalities), a county, a state or province, or a nation, as well as related governmental entities such regional, multi-national, or other international bodies such as the United Nations, the European Union, or the United Arab Emirates).

The carbon credit may be substantially received directly from a regulatory agency or administrative entity. In other instances, they may be received indirectly, for example, an entity using the methods or compositions herein may receive the carbon credits directly from a regulatory agency, and may then transfer the carbon credits to another entity. Transfer of the carbon credit may be in association with a given process or product using the genetically modified organism.

For example, a first entity may be identified that provides a consumable product that is distributed for consumption in an end-user mobile platform, wherein the consumption and/or production of the consumable product includes a corresponding resultant emission. For example, combustion of diesel fuel often results in the environmental release of corresponding nitrogen oxides and combustion of gasoline often results in the environmental release of corresponding sulfur oxide.

The first party may adopt a method of producing its product using the genetically modified organism, or use the product generated by the genetically modified organisms in their compositions, resulting in less harmful effects on the environment than conventional methods of generating, for example, diesel fuel, thus off-setting the environmental effects of the end product. The first party may then receive a carbon, or emission, credit as a result of a reduction of the total emission. The carbon credit may be received from a regulatory or administrative agency, or may be transferred to the first party from a second party, wherein the second party may have sold the genetically modified organism or the product of the genetically modified organism to the first party.

The carbon credit may be exchanged for a substantially liquid monetary instrument. For example, the carbon credit may be exchanged for a cash equivalent, such as cash, cheque, and the like. The carbon credit may also be exchanged for a legal grant regarding an intellectual property right, for example, but not limited to, an assignment or a license. The carbon credit may also be exchanged for a government tax subsidy or access to purchasers of a given market. The carbon credit may also be exchanged for use of another carbon emission process, such as one not comprising growing the organism. For example, a party may have a limited number of emissions it may release in a time period, for example, a month or a year, and going over the limit may incur fines and penalties. However, with carbon credits, the party going over the limit may exchange carbon credits to offset the fines or penalties or may be taken into account when determining the amount of emissions generated by the party.

The business method can also involve the production of a product other than a biofuel, for example a pharmaceutical, a food additive, an industrial chemical, a specialty chemical, a detergent, a fertilizer, a medicine, a paint, a plastic, a synthetic fibre, or a synthetic rubber. A business method associated with a biofuel, including those involving the use of carbon credits, are also relevant to the production of other types of useful products and materials.

It will be understood to persons skilled in the art of the invention that many modifications may be made without departing from the spirit and scope of the invention.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

Pursuant to the Budapest Treaty, plasmids pUC57/ATB1 (construct 1, Example 12), pET11/ATB1 (construct 2, Example 12), pSP124S (Example 11), and pBC1 were deposited on 14 Sep. 2010 with the National Measurement Institute (NMI), Australia in its capacity as an International Depository Authority. Deposited plasmid pUC57/ATB1 was assigned the accession number V10/022706. Deposited plasmid pET11/ATB1 was assigned the accession number V10/022707. Deposited plasmid pSP124S was assigned the accession number V10/022708. Deposited plasmid pBC1 was assigned the accession number V10/022709.

EXAMPLES

Example 1

Culture Conditions

The *B. braunii* strain Ayamé 1 (Race B) was cultured under an atmosphere of air enriched by 1% $CO_2$, 2% $CO_2$ or up to 10% $CO_2$ or more $CO_2$, using an air-lift system, with continuous illumination, and temperature around 25° C. The growth medium, was a modified CHU 13 ($KNO_3$ 200 mg/L, $MgSO_4.7H_2O$ 100 mg/L, $K_2HPO_4$ 39 mg/L, $CaCl_2.2H_2O$ 54 mg/L, FeNaEDTA 15 mg/L, $H_3BO_3$ 2.68 mg/L, $MnSO4.H_2O$ 1.54 mg/L, $ZnSO_4.7H_2O$ 0.22 mg/L, $CuSO_4.5H_2O$ 0.08 mg/L, $Na_2MoO_4.2H_2O$ 0.06 mg/L, $CoSO_4.7H_2O$ 0.09 mg/L) medium at 7.5. The tubes for illumination were from Mazda (SF 36w AZU/965; length: ~120 cm). The illumination intensity began at ~40 microeinsteins, and increased progressively up to ~120-160 microeinsteins (in the stationary phase), or more when culturing in a larger container (10 litres or greater).

Example 2

Genomic DNA Preparation

DNA was extracted from the Ayamé 1 strain of Example 1 as follows. First, approximately 2×200 milligrams of cell pellet was obtained by flocculation of cells in 50% ethanol (final concentration). Each cell pellet was resuspended in 2 mL of high salt DNA extraction buffer (200 mM Tris.HCl pH 7.5, 100 mM EDTA pH 8.0, 0.5 M NaCl) and subjected to 10 rounds of freeze-thaw using liquid nitrogen and a 45° C. water bath. Proteinase K was then added to a final concentration of 2 mg/mL and the mix was incubated at 55° C. for one hour, then 60° C. overnight. The resulting lysate was used whole in a Qiagen DNeasy Plant Maxi Kit (cat. no. 68163), to extract the DNA, according to the manufacturer's instructions.

Example 3

DNA Sequencing

The genome of *B. braunii* has not been sequenced and therefore is not known. Hence, it was necessary for the genome of *B. braunii* to be determined.

Twenty micrograms of the genomic DNA from *B. braunii* Ayamé 1 strain (Example 2) was used for genomic sequencing on an Illumina GenomeAnalyser machine (Geneworks, South Australia), to a total of 3 giga bases of data (comprising reads of ~35 bases long each). Another 20 □g of this DNA was used for genomic sequencing on a Roche FLX machine (Australian Genome Research Facility (AGRF), Queensland) to a total of 3 giga bases of data (comprising reads of ~250 bases long each).

Another twenty micrograms of the genomic DNA from *B. braunii* Ayamé 1 strain (Example 1) was used for genomic sequencing on an Illumina GenomeAnalyser machine (Illumina, Hayward, Calif. USA), to a total of 5 giga bases of data (comprising reads of ~75 bases long each).

Example 4

Genome Assembly and Gene Identification

Preparatory assembly of DNA contigs by merging of overlapping raw sequence data (Example 3) was performed at the AGRF. Subsequently, data from the Illumina platform was integrated at Flinders University using a variety of algorithms such as EULER, VELVET, CLC Genomics Workbench, DASH, to extend contigs and establish additional contigs.

Using BLAST or DASH algorithms, putative genes were identified and the genome will be assembled.

Exons encoded by amino acid sequences provided as SEQ ID NOs: 1 to 5 or 20 to 28were identified according to this example. The full polypeptide sequence (ATB1) provided as SEQ ID NO: 29 was identified according to this example.

Example 5

RNA Preparation

Cells of *B. braunii* Ayamé 1 strain were grown to stationary phase in CHU 13 medium (Example 1), then subcultured into an equal volume of fresh CHU 13 medium, and grown further for three days. On the third day, at the same time of day as the inoculation occurred three days beforehand, 1-10 mg cells were harvested using a 0.45 □m pore-size filter and scraping the cells from the filter using a scalpel blade. RNA was extracted from these cells using a Qiagen RNeasy Plant Mini Kit (cat. no. 74903). Extraction was begun by resuspending the cells in "buffer RLT" of that kit, and subjecting the suspension to at least 5 cycles of freeze-thaw using liquid nitrogen and 45° C. water bath, respectively. Subsequently, RNA was isolated according to the manufacturer's instructions for plant cell RNA extraction.

Example 6

Host Cell Species (Gene Recipient)

A. Algae

The disclosure is not limited to algae, but in one embodiment the host cell is an alga. The desirable criteria for host algae include ease and rapidity of growth, and flagellate morphology, because flagellate algae have positive phototaxis and promote ease of harvest. Given these criteria, the non-limiting example of species listed below may be gene recipients. Alternatively, the alga may be a seaweed, for example Pacific giant kelp.

1. Algae i. *Botryococcus* sp. other than that from which botryococcene synthase was isolated (Race B, Ayamé 1) and which satisfy at least one of the above criteria may be used according to the disclosure. Some examples include *B. braunii* Race A or Race L, or *Botryococcus sudeticus*.

ii. *Chlamydomonas* sp. is a genus of green alga. They are unicellular flagellates and used as a model organism for molecular biology, especially studies of flagellar motility and chloroplast dynamics, biogenesis, and genetics. One example is *C. reinhardtii*.

iii. *Chlorella* sp. is a genus of single-celled green algae. It is spherical in shape, about 2 to 10 μm in diameter, and lacks flagella. Through photosynthesis it multiplies rapidly requiring only carbon dioxide, water, sunlight, and small amounts of minerals to reproduce. One example is *Chlorella vulgaris*.

iv. Other green algal species that may be used according to the disclosure include *Scenedesmus obliquus, Dunaliella salina*, or *Haematococcus pluvialis*.

v. *Navicula tennerima* is a diatom species that has the potential for heterotrophic culture.

vi. Any alga of the dinophyceae, haptophyceae, stramenopiles, alveolates, cryptophyceae, euglenophyceae, or rhodophyceae may be used as hosts.

vii. *Choricystis* sp. is a genus of freshwater microalga with typical characteristic features comprising: small size of the cells; lack of mucilage; lack of pyrenoids and autosporulation with prevalent formation of two autospores. Two examples are *Ch. minor* and *Ch. chodatii*.

2. Cyanobacteria i. *Microcystis* sp. is a type of blue-green algae, also known as cyanobacteria, found in fresh water. Cyanobacteria are prokaryotic (meaning they possess no nucleus) and can be found in freshwater, marine water, or brackish water. *Microcystis* grows well in nutrient-rich water.

ii. Other cyanobacteria that may be used according to the disclosure include *Spirulina platensis* or *Synechocystis* sp.

B. Euglenids

*Euglena* sp. is typical of the euglenids, and is commonly found in nutrient-rich fresh water. The cells vary in length from around 20 to 300 μm, and are typically cylindrical, oval, or spindle-shaped with a single emergent flagellum used for movement. If sunlight is not available, it can absorb nutrients from decayed organic material. *Euglena* is also found in sewage systems. *Euglena* reproduces through binary fission, a process in which one cell is divided into two. *Euglena* has a contractile vacuole which prevents the cell from bursting.

C. Bacteria

1. Photosynthetic Bacteria

*Rhodospirillum rubrum* is a photosynthetic bacterium that may be a host cell according to the disclosure.

2. Non-Photosynthetic Bacteria

*E. coli* is a non-photosynthetic bacterium that is commonly found in the lower intestine of warm-blooded animals and may be a host cell according to the disclosure. Some strains possess flagella and are motile, whereas other strains lack flagella.

D. Other Photosynthetic Organisms

*Nicotiana tobaccum*, an example of a tobacco plant, is one example of a photosynthetic organism that may be used according to the disclosure. Another example may be *Arabidopsis thaliana*.

E. Yeast

Fungi may also be a suitable host cell, for example a yeast such as *S. cerevisiae* or *Pichia* sp.

Example 7

Expression Vector

A nucleic acid construct suitable for use in an expression vector for expressing botryococcene synthase or squalene synthase in *E. coli* may be designed. This may be based on a pET vector or similar, and the protein produced by the expression of the construct in *E. coli* may carry an N-terminal or C-terminal 6-histidine tag for purification of the protein. The expression construct may be synthesized.

A second nucleic acid construct suitable for use in an expression vector for expressing botryococcene synthase in *Chlamydomonas* may be designed. The expression construct may be synthesized. The *B. braunii* botryococcene synthase or squalene synthase construct or vector may include a selection marker comprising an antibiotic resistance gene, for example, the bleomycin resistance gene endowing resistance to phleomycin (Zeocin™, Invitrogen). The construct or vector may also include a promoter suitable for expression in *Chlamydomonas*. One suitable *Chlamydomonas* promoter may be derived from the RuBisCO gene). The construct or vector may also include at least one enhancer sequence that contributes to strong RNA expression in *Chlamydomonas*. The enhancer sequence may be positioned in at least one intron, and the intron may be deliberately positioned close to the transcription start site of the botryococcene synthase or squalene synthase coding region. The enhancer element, or the intron comprising the enhancer element, may be substituted into a native intron present in the botryococcene synthase or squalene synthase gene. Because an intron is spliced out during RNA processing, the native intron may be first identified by comparing the genomic botryococcene synthase or squalene synthase sequence with its corresponding RNA (cDNA) coding sequence. Furthermore, the recombinant intron may also be spliced out during RNA processing. The construct or vector may also include a transcription terminator (poly adenylation region) suitable for *Chlamydomonas*.

The expression construct may be ligated into a vector, for example a plasmid.

Nucleic acid sequences may be manipulated using computer software such as Sequencher (GeneCodes USA) or Bioedit.

Example 8

Transformation

Electroporation and the glass beads method may be used for the transformation of algal species. The transformed cells may be incubated for two weeks in 24 hour light at 25° C. Transformed cells may be subjected to antibiotic selection (phleomycin (Zeocin™) resistance). Colonies of resistant *Chlamydomonas* may become visible on plates from both kinds of transformation method after ten days. These *Chlamydomonas* transformants may require seven days further growth to produce enough material for reliable detection of the squalene synthase or botryococcene synthase gene.

Example 9

Functional Tests of Botryococcene Synthase or Squalene Synthase In Vivo

A botryococcene synthase gene or squalene synthase gene may be functionally tested in *E. coli*, *S. cerevisiae*, *C. reinhardtii*, or other living organisms. A gene may be expressed as its native open reading frame, or as the codon-optimised version optimised according to the codon-usage of highly expressed genes of the host organism. A botryococcene synthase or squalene synthase gene may be expressed with N-terminal or C-terminal tags for purification (for example, hexa-histidine, or any other peptide-based purification tag). Botryococcene synthase or squalene synthase may be expressed fused to Green Fluorescent Protein (GFP) or other fluorescent polypeptide. Botryococcene synthase or squalene synthase may be expressed as a chimera of a *B. braunii* polypeptide and a host (e.g. *C. reinhardtii*) polypeptide.

Identification and quantification of botryococcene or squalene production in the transgenic organism may be conducted by lysing the transgenic host cells, then detecting botryococcene or squalene directly.

Botryococcene is not present at all in *E. coli*, *S. cerevisiae*, or *C. reinhardtii*, so any botryococcene detected must be due to the presence of the transgene.

Squalene is present in *E. coli*, *S. cerevisiae*, or *C. reinhardtii*, so any squalene detected must be above the background level of squalene in cells of the untransformed control strain in order to be concluded that its production was due to the presence of the transgene.

Alternatively, the activity of the transgenic botryococcene synthase or squalene synthase enzyme in the transgenic host may be assayed by lysing the transgenic host cells, then detecting the botryococcene or squalene using a biochemical assay for conversion of FPP to botryococcene or squalene, for example incorporation of tritium from tritium-labelled FPP into tritium-labelled botryococcene or tritium-labelled squalene.

The botryococcene or squalene can be detected by chromatography, for example gas chromatography (GC), liquid chromatography (LC), or thin layer chromatography (TLC). The TLC procedure is useful for detecting tritium-labelled botryococcene or tritium-labelled squalene using photographic film or other detectors.

In representative experiments, a host organism such as *C. reinhardtii* or *E. coli* may be transformed with a nucleic acid molecule encoding botryococcene synthase or squalene synthase derived from *B. braunii* Race B strain Ayamé 1 (e.g. a nucleic acid molecule comprising any one of SEQ ID NOs: 6 to 9 or 30), and botryococcene or squalene production may be assayed.

Example 10

Functional Tests of Botryococcene Synthase or Squalene Synthase In Vitro

Botryococcene synthase or squalene synthase enzymes expressed in *E. coli*, *S. cerevisiae*, *C. reinhardtii* or other living organisms, and with or without N-terminal or C-terminal tags for purification, with or without GFP or other fluorescent polypeptide fusion, and with or without fused polypeptide of a homologous or heterologous *C. reinhardtii* polypeptide, can be assayed for specific enzyme activity in vitro.

Botryococcene or squalene production may be achieved by purification of transgenic botryococcene synthase or squalene synthase enzyme from the in vivo host, until it exists in a high state of purity substantially free of other enzymes of that host. Identification and quantification of botryococcene or squalene may be conducted using a biochemical assay for conversion of FPP to botryococcene or squalene. The botryococcene or squalene thus produced can be detected by chromatography, e.g. GC, LC or TLC. The TLC procedure may rely on incorporation of tritium-labelled FPP into tritium-labelled botryococcene or tritium-labelled squalene, and may be detected using photographic film or other detectors to detect tritium labelled botryococcene or squalene.

Example 11

Transformation of *C. reinhardtii* with the Squalene Synthase Gene from *B. braunii* Berkeley Strain The host strain of *C. reinhardtii* (CC400) possesses a cell wall weakness that allows DNA to be transformed into the cells by shaking the exogenous DNA and alga with glass beads to penetrate the weak cell wall. The glass beads technique is an established protocol. The cell wall deficient *Chlamydomonas* strain may also be transformed using electroporation.

Squalene Synthase Construct

To insert the *B. braunii* squalene synthase gene into *C. reinhardtii* CC400, a construct was made which has the capacity to express in *Chlamydomonas*. The artificial gene construct was based on pSP124S and was synthesised. The antibiotic resistance was used as a marker for transformation (bleomycin resistance gene, Zeocin™ antibiotic, a very active form of bleomycin antibiotic). To the *B. braunii* squalene synthase gene sequence was added a *Chlamydomonas* promoter from the *Chlamydomonas* RuBisCO gene), two enhancer/intron sequences that also promote strong RNA expression, and a *Chlamydomonas* transcription terminator.

Insertion into *Chlamydomonas* Genome

The squalene synthase construct was cut with the restriction enzyme SacI (Promega, Wis., USA) to linearise it, and was then transformed into *Chlamydomonas* cells by a glass beads method and in parallel by electroporation.

Bioinformatic Methods

The bleomycin resistance plasmid was obtained from Dr Britta Forster (Australian National University) and Dr Saul Purton (University College London). The gene construct was designed by downloading from Genbank the genomic DNA sequence, and RNA sequence for *B. braunii* squalene synthase, checking its completeness and locating introns by means of the program Sequencher (GeneCodes USA), then adding *Chlamydomonas* elements cut and pasted from the bleomycin resistance gene, using the freeware program Bioedit. Introns were positioned close to the start of the squalene synthase gene, where the enhancer element in them has easiest access to assist in promotion of transcription. The open reading frame for squalene synthase was not modified.

Detection of Transgenic *Chlamydomonas*

Primer pair 1 (5'-CCTTGATGGGGTATTTGAGCAC-3', SEQ ID NO: 16 and 5'-GGAATTCGGTTAGGCGCTGAGT-GTGGGTCTAGG-3', SEQ ID NO: 17) and primer pair 2 (5'-TGAGCACTTGCAACCCTTATCCG-3', SEQ ID NO: 18 and 5'-GGAATTCGGTTAGGCGCTGAGT-GTGGGTCTAGG-3', SEQ ID NO: 19) were used to amplify the *B. braunii* squalene synthase gene from genomic DNA that had been extracted from individual *C. reinhardtii* colonies positive for Zeocin™ resistance.

Results

Transformants

After the electroporation and glass bead protocols had been carried out using the squalene synthase pSP124S construct, and the transformed cells incubated for two weeks at 25° C. in 24 hour light on Tris Acetate Phosphate (TAP) agar with Zeocin™, colonies of Zeocin™ resistant *Chlamydomonas* became visible on plates from both kinds of transformation method, electroporation and glass beads. Individual colonies of these *Chlamydomonas* transformants were picked and grown in liquid TAP media to produce enough material for reliable detection of the *B. braunii* squalene synthase gene. TAP medium for *C. reinhardtii* is described in Gorman and Levine, *Proc. Natl. Acad. Sci. USA*, 1965, 54, 1665-1669.

Detection of Recombinant *Chlamydomonas*

Each transformed cell grew to a colony on the plate. Each colony represents a transformed cell carrying the bleomycin resistance gene. Thus, the *B. braunii* squalene synthase was detected in transformed cells of *C. reinhardtii* CC400. Primer pair 1 and primer pair 2 amplified the artificial gene from some colonies of transformed CC400 colonies (FIG. 33).

Other CC400 colonies that were bleomycin resistant but were not PCR-positive for the artificial gene carried only the antibiotic resistance parts of the squalene synthase pSP124S construct that was transformed into the cells, but did not also carry a full squalene synthase cassette. In such colonies the other parts of the DNA (i.e. some section of the squalene synthase gene, or its entirety) had been excluded by the organism during transformation and recombination.

Test of Function

Colonies that were both bleomycin resistant and positive for the squalene synthase pSP124S construct (i.e. using primer pairs 1 and 2) were assayed for squalene content. The transformed cells did not contain significantly more squalene than untransformed control cells.

Example 12

Cloning the ATB1 Triterpenoid Hydrocarbon Synthetic Nucleic Acid Sequence

Gene ATB1 was assembled from the *Botryococcus braunii* Ayamé genome and is 1212 nucleotides in length (FIG. 30, SEQ ID NO: 30). To facilitate cloning the ATB1 gene, as shown in FIG. 32, the nucleotides CACCACATGCAT (FIG. 43, SEQ ID NO: 33) comprising an NsiI restriction site (ATG-CAT; FIG. 44, SEQ ID NO: 34) were inserted immediately upstream of the native start codon of the nucleotide sequence provided in FIG. 30 (SEQ ID NO: 30). By joining these 33 additional nucleotides to the start codon, an NdeI restriction site (CATATG; FIG. 45, SEQ ID NO: 35) was also generated at the start codon. The addition of the 33 nucleotides resulted, in some constructs, in addition of one methionine and one histidine residue upstream of the native start codon of the polypeptide sequence provided in FIG. 29 (SEQ ID NO: 29), but not in the construct pET11a/ATB1 which utilises the NdeI site of the publicly available pET-11a vector to join to the NdeI site of the synthesised ATB1 gene (SEQ ID NO: 32).

Similarly, the nucleotides ATGCAT (SEQ ID NO: 34) comprising an NsiI restriction site were inserted immediately upstream of the native stop codon of the nucleotide sequence of the ATB1 gene provided in FIG. 30 (SEQ ID NO: 30). In all constructs this resulted in addition to the polypeptide sequence provided in FIG. 29 (SEQ ID NO: 29), of one methionine and one histidine residue, upstream of the native stop codon (giving ATB1-MH: FIG. 46, SEQ ID NO: 36). Furthermore, the nucleotides TCACTCGAGCCCGGG (FIG. 47, SEQ ID NO: 37) comprising XhoI and SmaI restriction sites were inserted immediately downstream of the native stop codon to facilitate cloning.

The resulting ATB1 sequence with these 33 additional nucleotides was synthesised (by Genscript, NJ USA).

Initially, ATB1 was cloned into standard vector pUC57 (construct 1) for verification by sequencing.

Subsequently, ATB1 was subcloned into vector pET-11a for overexpression of ATB1 protein including one methionine and one histidine residue at the C-terminus of ATB1 (ATB1-MH; SEQ ID NO: 36) via the inducible T7-lac promoter in that vector.

The synthesised ATB1 gene was cut with restriction enzymes NdeI and BclI and cloned into the NdeI and BamHI sites of pET-11a to produce construct pET11a/ATB1 (construct 2).

ATB1 was also subcloned into vectors that supply an inducible T7-lac promoter and either a N-terminal or C-terminal poly-histidine tag that can be used for affinity purification of the ATB1 protein. The synthesised ATB1 gene (SEQ ID NO: 32) was cut with restriction enzyme XhoI and cloned into the PmlI and XhoI sites of pET-302, to produce pET302/NT-His-ATB1 (construct 3) that encodes protein ATB1-MH augmented consecutively with one methionine, eight histidine, one methionine, and one histidine residues at its N-terminus (to produce MHHHHHHHHMH-ATB1-MH; FIG. 48, SEQ ID NO: 38). Alternatively, the synthesised ATB1 gene was cut with restriction enzyme NsiI and cloned directionally into the NsiI site of pET-302 (such that the T7-lac promoter is upstream) to produce CT-His-ATB1/pET302 (construct 4) that encodes protein ATB1-MH augmented consecutively at its N-terminus with one histidine and one methionine residue and augmented consecutively at its N-terminus with five histidine residues and residues VNSLEIDDIRA (to produce MH-ATB1-MH-HHHHHVNSLEIDDIRA; FIG. 49, SEQ ID NO: 39).

Example 13

Transformation of *E. coli* with the ATB1 Triterpenoid Hydrocarbon Synthetic Nucleic Acid Sequence Transformation The inducible promoter in ATB1 constructs 2, 3, and 4 is the viral T7 promoter. Constructs 2, 3, and 4 were transformed into *E. coli* strain BL21 Star™ (DE3), which is itself a transgenic *E. coli* containing a viral (T7) RNA polymerase that allows transcription from the T7 promoter.

Three vials of *E. coli* BL21 Star™ (DE3) were thawed on ice, to be used for transformation of the three constructs. To an aliquot of these cells 100 ng of DNA was added, mixed by stirring with the pipette tip, and incubated on ice for 30 minutes. The cells were heat shocked at 42° C. for 30 seconds, and immediately transferred back onto ice. To the transformed cells, 250 µl of SOC medium (20 g Bacto tryptone, 5 g Bacto yeast extract, 2 ml of 5 M NaCl, and 2.5 ml of 1 M KCl per litre of water, autoclaved before use, 20 ml of sterilized 1 M glucose added thereafter) was added and the tube containing the cells+SOC mix was shaken at 37° C. for 1 hour to allow cells to recover from transformation, and to allow the cells to express the ampicillin resistance protein from the b/a gene locus that is present on all constructs. Cells were spread onto LB agar (10 g Bacto-tryptone, 5 g yeast extract, 10 g NaCl, 15 g bacteriological agar per litre of water, autoclaved before use).

Glycerol stocks of *E. coli* transformants were prepared (20% glycerol+80% rich LB growth medium (10 g Bacto-tryptone, 5 g yeast extract, 10 g NaCl per litre of water, autoclaved before use)) by scraping transformants from LB agar containing ampicillin, and transferring several loopfuls of these cells into the glycerol+LB mix, resuspending the cells with a pipette tip, waiting an hour for cells to absorb glycerol, freezing in liquid nitrogen, and then placing and storing in a –80° C. freezer.

Restriction Digests

Plasmid DNA from the transformants was verified by extraction and restriction digestion. To prepare for DNA extraction, a small aliquot of each transformant was grown overnight at 37° C. in rich LB growth medium. DNA was extracted from transformed *E. coli* using a commercial miniprep kit (Wizard® Promega, Wis., USA).

All constructs were cut with restriction enzyme NdeI, which cuts at the specific DNA sequence CATATG at the start of the synthesised ATB1 gene. Each construct was also cut with a second restriction enzyme as follows: construct 2—BstXI (cuts at sequence CCANNNNNNTGG; FIG. 50, SEQ ID NO: 40); constructs 3 and 4—XhoI (cuts at sequence CTCGAG; FIG. 51, SEQ ID NO: 41). This was achieved by combining 0.5 µl of NdeI and 0.5 µl of the appropriate second restriction enzyme, together with 2 µl of 10× "Promega restriction buffer 4", 0.5 µl of bovine serum albumin (stock 10 mg/ml, final concentration 250 ng per µl), and 480 ng of DNA (about 6 to 12 µl), making a total reaction volume of 20 µl per reaction (by adding nuclease free water), and then incubating at 37° C. for 1 hour. Samples were electrophoresed on a 1% agarose gel in TAE buffer (40 mM Tris acetate, 1 mM EDTA) at 120 volts for 30 minutes, and DNA bands were visualised with SYBR-Safe fluorescent dye, on a UV illuminator, and digitally captured to disc using an 8 second exposure, with camera aperture fully open.

The pattern observed when construct 2 was cut with NdeI and BstXI included a band of 1070 base pairs (FIG. 34A) as predicted, confirming the presence of ATB1. The pattern observed when constructs 3 and 4 were cut with NdeI and XhoI included a band of 1230 base pairs (FIG. 34B) as predicted, confirming the presence of ATB1.

Example 14

Expression and Folding of ATB1 by Transformed *E. coli*

Untransformed *E. coli* and *E. coli* transformed with pET11a/ATB1 (construct 2) were each grown overnight at 37° C. in 5 ml LB medium containing 1% glucose. Cultures of transformed *E. coli* contained 100 µg/ml (final concentration) of ampicillin, whereas cultures of untransformed *E. coli* contained no ampicillin. Next day, cultures were centrifuged and the pellets resuspended in 1 ml of LB medium, which was added to 49 ml of fresh LB medium. Again, cultures of transformed *E. coli* contained 100 µg/ml (final concentration) of ampicillin, whereas cultures of untransformed *E. coli* contained no ampicillin. The 50 ml cultures were incubated at 37° C. with shaking and were monitored by spectrophotometer at wavelength 600 nm. Sterile technique was maintained throughout. The OD600 had reached 0.65 by 1.5 hours, and accordingly cells were ready to be induced.

The inducing agent isopropylthiogalactoside (IPTG) was added to each culture at a final concentration of 1 mM. At 0, 2 and 4 hours post IPTG induction, 1 ml of culture was removed and centrifuged. The resulting pellet was boiled for 10 minutes in 200 µl of protein assay buffer (50 mM Tris-HCl pH 6.8, 10 mM Dithiothreitol, 1% sodium dodecyl sulfate), and then protein concentration was measured on a Nanodrop spectrophotometer set at a wavelength of 280 nm. A sample containing 60 µg of protein was added to 3× strength Laemmli buffer (6% SDS, 30% glycerol, 15% β-mercaptoethanol, 0.006% bromophenol blue, 0.1875 M Tris-HCl) and boiled for 2 min.

Also at 4 hours post IPTG induction, 5 ml of culture of *E. coli* transformed with pET11a/ATB1 was removed and centrifuged. The resulting pellet was resuspended in 500 μl of lysis buffer B (50 mM Tris-HCl pH 7.5, 1 mM dithiothreitol, 2 mM PMSF, 0.5% Triton X-100, 100 μg DNase) then repeatedly freeze-thawed (10 times). The lysate was centrifuged for 15 min at 13,000 rpm in a microfuge at 4° C. The supernatant was removed, its protein content was measured with the Nanodrop spectrophotometer, and the supernatant sample was diluted using 3× Laemmli buffer. Lanes 8 and 9 of FIG. 35 contain 15 μl and 20 μl, respectively, of this supernatant.

The samples were loaded on a SDS-PAGE minigel comprising a stacking gel (4% acrylamide) and a resolving gel (10% acrylamide). The minigel was run at 170 volts. All lanes of the minigel contained 1× Laemmli buffer final concentration. The proteins on the minigel were visualised using Coomassie dye (FIG. 35).

ATB1 protein was not present in untransformed *E. coli* cells at any time (FIG. 35, Lanes 1, 3, 5), nor was it present in *E. coli* cells transformed with pET11a/ATB1 (construct 2) and sampled at 0 h post IPTG-induction (FIG. 35, Lane 2). However, ATB1 protein (running between 46 kDa and 30 kDa, i.e. between arrows compared to lane 7: molecular weight markers upper arrow 46 kDa, lower arrow 30 kDa) was expressed by transformed *E. coli* (transformed with construct 2) at 2 h and 4 h post IPTG induction (FIG. 35, Lanes 4, 6, 8 and 9). ATB1 protein (arrowed in lane 9, FIG. 35: soluble ATB1 protein) was present in the soluble supernatant of the cell lysate of *E. coli* transformed with construct 2 (FIG. 35, Lanes 8 and 9), after lysing and centrifugation at 13000 rpm in a microfuge for 15 minutes. This indicates that ATB1 was correctly folded, since incorrectly folded ATB1 would be in the insoluble pellet.

Example 15

Generation of a Triterpenoid Hydrocarbon by Transformed *E. coli*

A few microlitres of each of untransformed *E. coli*, and *E. coli* transformed with either pET11a/ATB1 (construct 2) or pET302/NT-His-ATB1 (construct 3) were taken from glycerol stocks and added to 200 ml of LB medium. LB medium in which transformed *E. coli* were grown contained ampicillin (100 μg/ml), whereas LB broth in which untransformed *E. coli* were grown contained no ampicillin. Each culture also contained sterile glucose (final concentration 1% glucose w/v) to prevent premature expression of ATB1. The cultures were shaken overnight at 37° C. to obtain a sufficient number of cells in stationary phase to be used as inoculates.

Each 200 ml culture was centrifuged and the pellet resuspended in 10 ml of LB medium, then added to 990 ml of fresh LB medium containing the inducer IPTG (final concentration 1 mM), and grown for 1 hour at 37° C. to allow cells to recover from lag phase and begin to divide. The 1 litre cultures were then incubated overnight at 28° C. to 33° C. with shaking. The temperature 28° C. to 33° C. may increase the yield of correctly folded ATB1 protein relative to the yield at 37° C.

Following the overnight incubation, the cultures were centrifuged and the pellets resuspended in 10 ml of lysis buffer A (50 mM MOPS (4-Morpholinepropanesulfonic acid) buffer pH 7.3; 25 mM β-mercaptoethanol; 20 mM MgCl$_2$; 0.5 mM PMSF (Phenylmethylsulfonyl fluoride)). First the sample of untransformed *E. coli* placed into a cell crusher at 4° C., and then the sample of *E. coli* transformed with pET11a/ATB1 (construct 2) was placed into a cell crusher at 4° C. The cell crusher was extensively washed with 75% ethanol 25% water, and then fresh distilled water, between samples. After crushing, these two samples were extracted with 10 ml heptane at 60° C. for two minutes with vigorous shaking. A third sample of *E. coli* transformed with pET302/NT-His-ATB1 (construct 3) was extracted directly with 10 ml heptane, by heating over a bunsen burner until boiling, without cell crushing.

Heptane was separated from aqueous material and cell debris by centrifugation in PTFE/Teflon® tubes. The heptane fraction was removed using a single-use heptane-rinsed glass pipette. Samples were evaporated in the order untransformed *E. coli*, *E. coli* transformed with pET11a/ATB1 then *E. coli* transformed with pET302/NT-His-ATB1 (construct 3). The rotary evaporator was rinsed twice, using 10 ml of clean heptane per rinse, between samples. Each sample was concentrated to 2 ml.

Heptane-soluble polar compounds, consisting of mostly fatty acids, their esters and lipids, were removed by: 1) Adding sufficient heptane to the sample to increase its volume to 10 ml; 2) Passing the entire 10 ml of heptane through a column (LCTech (Germany), Elufix Column, Part number 9370) consisting of 2 g of anhydrous sodium sulfate and 2 g of synthetic magnesia-silica gel (Florisil®) and collecting the eluent; 3) Reducing the volume of heptane eluent collected to approximately 0.8 ml under a stream of nitrogen.

Example 16

Generation of a Triterpenoid Hydrocarbon by Lysate of Transformed *E. coli*

A few microlitres of each of *E. coli* transformed with either pET11a/ATB1 (construct 2) or pET302/NT-His-ATB1 (construct 3) were taken from glycerol stocks and added to 20 ml of LB medium (also known as nutrient broth NB). LB medium in which transformed *E. coli* were grown contained ampicillin (100 μg/ml), whereas LB broth in which untransformed *E. coli* were grown contained no ampicillin. Each culture also contained sterile glucose (1% final concentration). The cultures were incubated overnight at 37° C. with shaking to obtain a sufficient number of cells in stationary phase to be used as inoculates. A glycerol stock of untransformed *E. coli* BL21 Star™ (DE3) was used directly as an inoculate. After overnight culture, cells were centrifuged to remove glucose, and the pellets each resuspended in LB medium without glucose, to allow transgene expression.

Untransformed *E. coli* were incubated at 37° C. only, whereas each of the two transformed *E. coli* strains was incubated both at 18° C. and 37° C. (i.e. making a total of 5 samples).

Each of the samples to be induced at 37° C. was resuspended in 75 ml of LB (without glucose), grown for 2 hours at 37° C. to approximately attain log phase, and then induced with 0.5 mM IPTG. These were then further incubated for 2 hours at 37° C., to induce transgene expression.

Each of the samples to be induced at 18° C. were passaged directly from the pellets obtained after removing glucose from overnight cultures. The pellets were resuspended in 4 ml of overnight culture, then transferred to 500 ml of LB containing 0.5 mM IPTG (final concentration) and incubated overnight at 18° C.

After induction, cultures were centrifuged. The pellet was resuspended in 5 ml of lysis buffer A. Lysis was achieved by sonication for 1 minute, on ice (ice-water slurry) in a glass beaker. Samples were clarified by aliquotting into microfuge tubes, and centrifuging at 13000 rpm, at 4° C. for 15 minutes, then combining aliquots of identical samples to make 3.6 ml in total of each sample. To each clarified lysate, 35 µl of FPP stock (stock 10 mM in ethanol) and 15 mg of NADPH powder was added and the mix was incubated with gentle shaking at 37° C. for 30 minutes (FIG. 36).

After incubation with FPP and NADPH, 10 ml of heptane was added to each lysate, and each was vigorously shaken by hand for about 20 seconds. Then the lysates were allowed to separate into hydrophobic and hydrophilic fractions overnight at room temperature with gentle shaking. Next day, the samples were centrifuged in PTFE/Teflon® tubes then evaporated as described in Example 14.

Example 17

Detection of a Triterpenoid Hydrocarbon by Gas Chromatography—Mass Spectrometry (GC-MS)

Samples derived from Examples 15 and 16 were analysed by GC-MS.

GC-MS was performed on an Agilent Technologies 5975C mass spectrometer equipped with an Agilent technologies 7890A gas chromatograph and a 7683B autosampler.

The capillary column was an Alltech EC-5 (15 m×0.25 mm i.d.). Splitless injection was used with a split time of 60 seconds. Injection port temperature was 300° C. The carrier gas was helium in constant flow mode at 1.8 mL/min. Injection volume was 1 µL.

The GC temperature program was: initial temperature of 40° C. for 4 min, ramp rate of 20° C./min, final temperature of 350° C. for 4 min. The GC/MS interface temperature was set to 280° C. The FID temperature was 325° C.

For full scan mass spectra, the mass spectrometer was scanned from m/z 35 to m/z 550. Electron ionisation (EI) was used with the electron energy set to 70 eV. The source temperature was 230° C. The MS quadruple was set to 150° C.

Authentic squalene and authentic $C_{30}$ botryococcene were analysed by GC-MS (FIGS. 37 and 38, respectively).

Squalene (elution time 16.5 min, mass 410) and botryococcene (elution time 15.8 min, mass 410) were undetectable in untransformed *E. coli* when analysed by GC-MS (FIG. 39). In contrast, Compound X (elution time 15.7 min, mass 408) and Compound Y (elution time 16.5 min) with a similar elution time to authentic squalene were detected in *E. coli* transformed with construct 2 and induced with IPTG (FIGS. 40 and 41).

When supplemented with FPP and NADPH, a cell lysate of *E. coli* transformed with construct 2 and induced with IPTG produced Compound Y (elution time 16.5 min) as determined by GC-MS, whereas Compound X (elution time 15.7 min) was undetectable (FIG. 42).

The mass spectrum of Compound X after electron cracking (FIG. 39) is similar to that of both squalene (FIG. 37) and botryococcene (FIG. 38), except that a majority of peaks are smaller by two mass units than those of squalene and botryococcene (Table 1). The absence of two hydrogens, demonstrated both by the overall molecular weight and the electron cracked mass spectrum, indicates that the triterpenoid Compound X is a "dehydro" triterpenoid Indeed, the mass spectrum is consistent with a dehydrotriterpenoid, such as 12,13-dehydrosqualene, also known as 4,4'-diapophytoene.

On the basis of GC-MS, Compound X and Compound Y are identified as triterpenoid hydrocarbons. Specifically, Compound X is dehydrosqualene and Compound Y is squalene.

TABLE 1

Mass spectra of triterpenoids squalene, botryococcene and Compound X after electron cracking. Major peaks (companion peaks in brackets) are reported.

| Compound X | Squalene | $C_{30}$ Botryococcene |
|---|---|---|
| 408 | 410 | 410 |
| 393 | 395 | 395 |
| 378 (377) | | |
| 365 | 367 | 367 |
| 356 (352) | | 354 |
| 339 (340) | 341 | 341 |
| 327 (326) | 325 | 325 (327, 328) |
| 311 | | 313 |
| 297 | 299 | 299 (297) |
| 285 (282) | 285 (287) | 285 |
| 271 | 273 | 271 (273) |
| 257 (255, 258) | 257 (259) | 257 (259) |
| 243 (241) | 245 (244) | 245 (243) |
| 229 | 231 | 231 (229) |
| 215 | 217 (218) | 217 (215) |
| 203 (201) | 203 203 | |
| 187 (189) | 191 (189, 192) | 191 (189) |
| 173 (175) | 175 (177) | 175 (177) |
| 159 (161) | 161 (163) | 161 (163) |
| 147 (145) | 149 | 149 (147) |
| 133 | 137 (136) | 135 |
| 119 (121) | 121 (123) | 121 (123) |
| 109 (107, 105) | 109 (107) | 109 (107) |
| 93 (95, 91) | 95 (93) | 95 (93) |
| 81 (79) | 81 | 81 |
| 69 | 69 | 69 |
| 55 | 55 | 55 |
| 41 | 41 | 41 |

Example 18

Algae Culture

Algae, for example *Chlamydomonas reinhardtii*, is grown in Aquasol® soluble fertiliser with trace elements at 150 mg/L. Aquasol® comprises nitrogen as monoammonium phosphate 1.8%, nitrogen as potassium nitrate 2.6%, nitrogen as urea 18.6% (total nitrogen 23%), phosphate as monoammonium phosphate 4% (total phosphate 4%), potassium as potassium nitrate 7.8%, potassium as potassium chloride 10.2% (total potassium 18%), zinc as sulphate 0.05%, copper as sulphate 0.06%, molybdenum as sodium molybdite 0.0013, manganese as sulphate 0.15%, iron as sodium ferric EDTA 0.06%, boron as sodium borate 0.011%.

Alternatively, algae is grown in TAP medium, which is described in Gorman and Levine, *Proc. Natl. Acad. Sci. USA*, 1965, 54, 1665-1669.

Algae are cultured in raceway ponds made of opaque plastic with dimensions 1.52 m wide, 2.44 m long and 0.61 m deep with a capacity of 2000 L. The raceway ponds are powered by a paddle wheel and operate at 20-30 cm depth. The paddle wheel rotation is adjusted to generate a flow rate of 21±3 cm s$^{-1}$. Alage are also cultured in vertical tank reactors (VTR) with dimensions 0.45 m diameter and 1.52 m height with 100 L working volume and made of transparent acrylic sheets. A roll of low density polyethylene (LDPE-Uline-6-Mil heavy duty polytubing with 50.8 cm circumference) material is used to fabricate hanging polybags with dimensions 95 cm deep, 15 cm diameter, 20 L working volume. All the reactors are attached with delivery tubings and air stones for bubbling 5-6% $CO_2$ and air mixture.

Supplemental $CO_2$ is derived from a liquid $CO_2$ storage tank blended with air using a Concoa BlendMaster Model 1000 mixer and passed through a Whatman HEPA-Vent filter at 5-6% $CO_2$ concentration in air. Cole Parmer rotameters are used to regulate air flow rates among the raceways, VTR and polybags. Raceways are stirred continuously with paddle wheels powered by Dayton Model 4Z129B motors (90 V, 1.27 Amps). For the VTR, mixing is accomplished by bubbling $CO_2$ and air mixture through rectangular air stones (15×4×4 cm), whereas for the polybags, the mixture is simply bubbled into a port disk (0.72 cm opening) placed at the bottom of the polybag. To keep the VTR and polybags stirred after terminating the supply of supplemental $CO_2$, each evening ambient air is pumped into these cultures at the same flow rate as that of the supplemental $CO_2$ gas mix during the day. Culture temperature and pH for the raceways, VTR and polybags are measured daily.

A MasterFlex Model 77250-62 peristaltic pump is used to fill polybags at a flow rate of 3-4 L $min^{-1}$. Inoculum is drained from the bottom of VTR through a gate valve fitted with a 1.3 cm internal diameter garden hose that is either directly sent into the raceways or into pre-autoclaved glass carboys/Erlenmeyer flasks for subsequent delivery to the intended culture system.

Algae are grown batch-wise in a green house. The raceways, VTR and polybags are arranged in a row parallel to the east-west direction.

Biomass is harvested with a Lavin process centrifuge (Model: 12-413 V) operated at 2250 g, manually removed from the interior drum with a spoon and dried at 40° C. in a hot air oven for 72 h. It is stored at 4-5° C.

Raceway ponds are filled with 800 L of growth medium. These are inoculated with 50 L each of exponentially growing cultures of algae. After inoculation, the raceways operate at 30 cm depth.

Alternatively, raceways with 496 L growth medium are inoculated with 18 L of algal culture and operate at 20 cm depth with a total volume of 550 L. VTR have 88 L growth medium and 4 L of algal culture is added as inoculum. VTR operate with 100 L working volume and the depth of water column is maintained at 61 cm.

Alternatively, algae are grown in raceways (working volume: 500 L; Depth: 18 cm), VTR (working volume: 100 L; diameter: 45 cm; depth: 61 cm) or polybags (working volume: 20 L; diameter: 16 cm; depth: 95 cm). To each of the raceways, VTR and polybags, 450, 90 and 18 L of growth medium is filled and 25, 5 and 1 L of the inoculum is added, respectively. Final volumes are, 500 L (18 cm deep) in raceways, 100 L (61 cm deep) in VTR and 20 L (95 cm deep) in polybags.

Example 19

Generating an ATB1 Construct Containing *Chlamydomonas* Control Elements

Disclosed is a method for generating an expression vector pCE2 (plasmid for *Chlamydomonas* Expression 2). Also disclosed is a method for putting the ATB1 gene under the control of elements present in this vector pCE2, thus creating construct pCE3-ATB1 (FIG. 54, SEQ ID NO: 43). Control elements used are a *C. reinhardtii* Rubisco small subunit (RbcS2) promoter and a *C. reinhardtii* RbcS2 terminator.

An interim vector pCE1 is first constructed. The *C. reinhardtii* RbcS2 terminator is amplified from pSP124S using PCR, and is ligated back into pSP124S at the polylinker to generate the interim vector pCE1. The *C. reinhardtii* RbcS2 terminator is amplified from pSP124S using PCR, and is ligated into pCE1 at the polylinker upstream of the terminator to generate expression vector pCE2.

Stepwise, firstly the RbcS2 terminator is amplified from pSP124S using forward primer RbcS2-termforw (5'-GAGTACGCGGCCGCCCCGCTCCGTGTAAAT-3'; FIG. 55, SEQ ID NO: 44), which contains a NotI restriction site, and reverse primer RbcS2-termrev (5'-GCACTCGAATTCGCTTCAAATACGCCCAGC-3'; FIG. 56, SEQ ID NO: 45), which contains an EcoRI restriction site. The polymerase used is Promega (Madison, Wis., USA) GoTaq. All conditions used of GoTaq enzyme activity are within the manufacturer's instructions (dNTPs concentration 0.1 mM, $MgCl_2$ concentration 1 mM, primer concentration 0.4 pmol/μl, template concentration 1 pg/μl, 1× manufacturer's buffer) and the PCR cycle conditions used are 94° C. for 3 min, then 40 cycles of: 94° C. for 30 s, 55° C. for 30 s, 72° C. for 1 min, and a final extension of 72° C. for 7 min. The amplicon generated is 260 bp long and is purified in a Promega Wizard PCR purification column, then cut with NotI and EcoRI for 1 hr at 37° C., and subsequently heat treated for 10 minutes at 65° C. to denature enzymes, before purifying again through a Wizard PCR purification column.

The amplified and restricted terminator is then ligated into vector pSP124S that has been prepared as follows: the vector is cut with NotI and EcoRI by incubating with these enzymes for 1 hr at 37° C., and the vector is then purified through a Wizard PCR purification column; the cut and purified vector is treated with Promega Calf Intestinal Alkaline Phosphatase according to the manufacturer's instructions, in order to prevent self ligation; the phosphatase-treated vector is purified through a Wizard PCR purification column. Ligation of the restriction-cut terminator amplicon and phosphatase treated pSP124S is accomplished with Promega T4 ligase according to the manufacturer's instructions. The ligation mix is transformed into DH10α electrocompetent *E. coli* cells, using a Biorad (Hercules, Calif. USA) Gene Pulser II electroporator set at 2.5 kV, together with a Molecular Bioproducts (San Diego, Calif., USA) electroporation cuvette with a 2 mm gap width.

Transformants are screened by plating the transformation mix onto Oxoid (Basingstoke, Hampsire, UK) nutrient agar (1 g/L Lab-Lemco powder, 2 g/L yeast extract, 5 g/L peptone, 5 g/L NaCl, 15 g/L agar) plates, containing 100 μg/ml (final concentration in agar) of sterile-filtered ampicillin. Colonies are picked and grown overnight in LB medium (nutrient broth), and their plasmid DNA extracted the following day. These plasmids are screened by PCR using forward primer pSP124S-preSacI (5'-CACTAAAGGGAACAAAAGCTG-3'; FIG. 57, SEQ ID NO: 46) and reverse primer RbcS2-termrev (5'-GCACTCGAATTCGCTTCAAATACGCCCAGC-3'; FIG. 56, SEQ ID NO: 45), and those plasmids which yield a PCR amplicon of 291 bp are considered positive. Positive plasmids are sequenced by the Australian Genomic Research Facility (AGRF) using a T3 primer (5'-GCAATTAACCCTCACTAAAGGGA-3'; FIG. 58, SEQ ID NO: 47) and dye-terminator chemistry to confirm the RbcS2 terminator sequence. This interim vector that contains a *C. reinhardtii* RbcS2 terminator in the polylinker is named pCE1.

Similarly, in making pCE2, the RbcS2 promoter is first amplified from pSP124S using forward primer RbcS2-promforw (5'-GAGTGCGAGCTCTAAATGCCAGAAGGAGCG-3'; FIG. 59, SEQ ID NO: 48), which contains a SacI restriction site, and reverse primer RbcS2-promrev (5'-GTCACTGCGGCCGCTTTAAGATGTTGA-3'; FIG. 60, SEQ ID NO: 49), which contains a NotI restriction site. The polymerase used is Promega GoTaq. All conditions used of GoTaq enzyme activity are within the manufacturer's instructions (dNTPs concentration 0.1 mM, $MgCl_2$ concentration 1 mM, primer concentration 0.4 pmol/µl, template concentration 1 pg/µl, 1× manufacturer's buffer) and the PCR cycle conditions used are 94° C. for 3 min, then 40 cycles of: 94° C. for 30 s, 52° C. for 30 s, 72° C. for 1 min, and a final extension of 72° C. for 7 min. The amplicon generated is 239 bp long and is purified in a Wizard PCR purification column, then cut with SacI and NotI for 1 hr at 37° C., and subsequently heat treated for 10 minutes at 65° C. to denature enzymes, before purifying again through a Wizard PCR purification column. The amplified and restricted promoter is then ligated into vector pCE1 that has been prepared as follows: the vector is cut with SacI and NotI, by incubating with these enzymes for 1 hr at 37° C., and the vector is then purified through a Wizard PCR purification column. The cut and purified vector is treated with Promega Calf Intestinal Alkaline Phosphatase according to the manufacturer's instructions in order to prevent self ligation. The phosphatase-treated vector is purified through a Wizard PCR purification column.

Ligation of the restriction-cut promoter amplicon and phosphatase treated pCE1 is accomplished with Promega T4 ligase according to the manufacturer's instructions. The ligation mix is transformed into DH10α electrocompetent *E. coli* cells, using a Biorad Gene Pulser II electroporator, together with a Molecular Bioproducts electroporation cuvette with a 2 mm gap width. Transformants are screened by plating the transformation mix onto Oxoid nutrient agar plates, containing 100 µg/ml (final concentration in agar) sterile-filtered ampicillin. Colonies are picked and grown overnight in LB medium (nutrient broth), and their plasmid DNA extracted the following day. These plasmids are screened by PCR using forward primer pSP124S-preSacI (5'-CACTAAAGGGAACAAAAGCTG-3'; FIG. 57, SEQ ID NO: 46) and reverse primer RbcS2-termrev (5'-GCACTCGAATTCGCTTCAAATACGCCCAGC-3'; FIG. 56, SEQ ID NO: 45), and those plasmids which yield a PCR amplicon of 494 bp are considered positive. Positive plasmids are sequenced by the AGRF using a T3 primer (5'-GCAATTAACCCTCACTAAAGGGA-3'; FIG. 58, SEQ ID NO: 47) and dye-terminator chemistry, to confirm the RbcS2 promoter sequence.

This novel expression vector that contains a *C. reinhardtii* RbcS2 terminator and a *C. reinhardtii* RbcS2 promoter, both present in the polylinker, is named pCE2. It contains a NotI site in between the RbcS2 promoter and the RbcS2 terminator. For greater expression, a hybrid *C. reinhardtii* Hsp70A/Rbcs2 promoter may be used instead of the RbcS2 promoter (Schroda et al. *The Plant Journal*, 2000, 21, 121-131 and Schroda et al., *The Plant Journal*, 2002, 31, 445-455).

As a further example, the ATB1 gene is ligated into vector pCE2 at the NotI site between the RbcS2 promoter and terminator, to create an expression construct pCE3-ATB1. Specifically, in generating the expression construct pCE3-ATB1, the ATB1 gene is amplified from construct pUC57/ATB1 that was manufactured at Genscript (Piscataway, N.J., USA). Construct pUC57/ATB1 contains the inferred cDNA of the *Botryococcus braunii* Ayamé ATB1 gene, that was shown to function in *E. coli* in the form of subcloned version pET11/ATB1 (Example 15). Amplification of the ATB1 gene from construct pUC57/ATB1 is accomplished using forward primer ATB1forw (5'-GTCACTGCGGCCGCGTCACTTTGTAGGGCT-3'; FIG. 61, SEQ ID NO: 50) that contains a NotI restriction site, and reverse primer ATB1rev (5'-GAGTACGCGGCCGCAAAATGAGTATGCACC-3'; FIG. 62, SEQ ID NO: 51) that also contains a NotI restriction site. The polymerase used is Phusion (Finnzymes, Espoo, Finland). All conditions used for Phusion enzyme activity are within the manufacturer's instructions (dNTPs concentration 0.7 mM, primer concentration 0.4 pmol/µl, template concentration 1 pg/µl, 1× manufacturer's buffer) and the PCR cycle conditions used are 94° C. for 2 min, then 40 cycles of: 94° C. for 10 s, 53° C. for 30 s, 72° C. for 1 min, and a final extension of 72° C. for 7 min. The amplicon generated is 1244 bp long and is purified in a Wizard PCR purification column, then cut with NotI for 1 hr at 37° C., and subsequently heat treated for 10 minutes at 65° C. to denature the NotI enzyme, before purifying again through a Wizard PCR purification column.

The amplified and restricted ATB1 gene is then ligated into vector pCE2 that has been prepared as follows: the vector is cut with NotI, by incubating with these enzymes for 1 hr at 37° C., and the vector is then purified through a Wizard PCR purification column; the cut and purified vector is treated with Promega Calf Intestinal Alkaline Phosphatase according to the manufacturer's instructions to prevent self ligation; the phosphatase-treated vector is purified through a Wizard PCR purification column. Ligation of the restriction-cut ATB1 gene and phosphatase treated pCE2 is accomplished with Promega T4 ligase according to the manufacturer's instructions. The ligation mix is transformed into DH10α electrocompetent *E. coli* cells, using a Biorad Gene Pulser II set at 2.5 kV, using a Molecular Bioproducts electroporation cuvette with a 2 mm gap width. Transformants are screened by plating the transformation mix onto Oxoid nutrient agar plates, containing 100 µg/ml (final concentration in agar) of sterile-filtered ampicillin. Colonies are picked and grown overnight in LB medium (nutrient broth), and their plasmid DNA extracted the following day. These plasmids are screened by PCR using forward primer pSP124S-preSacI (5'-CACTAAAGGGAACAAAAGCTG-3'; FIG. 57, SEQ ID NO: 46) and reverse primer RbcS2-termrev (5'-GCACTCGAATTCGCTTCAAATACGCCCAGC-3'; FIG. 56, SEQ ID NO: 45), and those plasmids which yield a PCR amplicon of 1718 bp are considered positive. Positive plasmids are sequenced by the AGRF using a T3 primer (5'-GCAATTAACCCTCACTAAAGGGA-3'; FIG. 58, SEQ ID NO: 47) and dye-terminator chemistry, to confirm the ATB1 gene sequence, as well as the RbcS2 promoter sequence and RbcsS2 terminator sequence. This novel construct that contains the *B. braunii* ATB1 gene under the control of the *C. reinhardtii* RbcS2 promoter and the *C. reinhardtii* RbcS2 terminator, is named pCE3-ATB1.

Example 20

Transforming pCE3-ATB1 into *C. reinhardtii* CC503 to Generate Transgenic Organism Construct pCE3-ATB1 is transformed into *C. reinhardtii* cells (cell-wall deficient strain CC503) by the method of vortexing the DNA and cells together in the presence of glass beads. To prepare the *C. reinhardtii* cells, CC503 culture is grown to log phase in Tris Acetate Phosphate (TAP) medium (Gorman and Levine 1965), then 50 ml are centrifuged and the pellet aseptically resuspended in 0.5 ml of TAP medium. To a sterile glass tube containing 300 mg of autoclaved Biospec (Bartlesville, Okla., USA) glass beads (0.5 mm diameter), 500 µl of this thick cell suspension is added together with 2 µg of DNA that has been linearised by cutting with SacI site at 37° C. for 1 hr. Prior to adding to the cells and beads, the DNA is heat treated at 65° C. for 10 mins, cooled and purified with a Wizard PCR purification column, and resuspended in 45 µl of water. The cells, DNA, and beads mix is vortexed on a Ratek Instruments (Boronia, Victoria, Australia) vortexer at top speed for 30 seconds, thus transforming the *C. reinhardtii* cells with the pCE3-ATB1 construct. Following vortexing the transformed cells are spread on a TAP-agar plate that contains 3 μg per ml (final concentration in agar) of Invitrogen Zeocin (Carlsbad, Calif., USA). After two weeks growth at 25° C. in a constant light, or a light-dark cycle of 16 hr light, 8 hours dark, the TAP agar plate containing transformed cells shows colonies of transformed C. reinhardtii, that have been positively selected on the basis of Zeocin resistance. Zeocin is a form of bleomycin. A bleomycin resistance gene is present in pSP124S and in pCE3-ATB1. The bleomycin gene also functions to confer resistance to zeocin.

Zeocin resistant colonies of C. reinhardtii are picked individually into individual 1 ml aliquots of fresh TAP liquid medium using a sterile wire loop to transfer them. The isolates are then each grown at 25° C. in a constant light, or a light-dark cycle of 16 hr light, 8 hours dark, for up to 1 week, and then DNA is extracted from each by the procedure of Example 2. Isolates are screened by PCR to ascertain presence absence of the ATB1 gene. Primers used for PCR screening to identify transgenic C. reinhardtii are the forward primer RbcS2-promforw (5'-GAGTGCGAGCTCTAAAT-GCCAGAAGGAGCG-3'; FIG. 59, SEQ ID NO: 48) and reverse primer RbcS2-termrev (5'-GCACTCGAATTCGCT-TCAAATACGCCCAGC-3'; FIG. 60, SEQ ID NO: 56, SEQ ID NO: 45). Zeomycin resistant isolates from which an amplicon of 1703 bp is obtained are considered positive, i.e. contain the ATB1 gene. The 1703 bp amplicon from five of these isolates is purified from an agarose electrophoresis gel, using a Wizard PCR and Gel purification kit, sequenced directly at AGRF, using either one of the PCR primers that were used to generate the amplicon. The sequence of the 1703 bp amplicon is compared to the ATB1 sequence as well as to its flanking RbcS2 promoter and RbcS2 terminator. Isolates which have identical sequence as the ATB1 gene source DNA and as the Rbcs2 control element source DNAs, are named as specific cases of transgenic organism CC503-ATB1, as follows: CC503-ATB1A, CC503-ATB1B, CC503-ATB1C, CC503-ATB1D, CC503-ATB1E.

Example 21

Assaying Triterpenoids in Transgenic Alga CC503

C. reinhardtii cells are assayed for levels of triterpenoids, and identities of triterpenoids, using GC-MS. Transgenic C. reinhardtii grown using standard media, temperatures, and light regimes, is centrifuged at 1,000 to 20,000 rpm to pellet the cells, the supernatant is decanted and discarded, and cells are resuspended in lysis buffer (50 mM 3-morpholinopropane-1-sulfonic acid pH7.3, 25 mM β-mercaptoethanol, 20 mM MgCl$_2$, 1 mM Phenylmethylsulfonylfluoride) then subjected to a French Press or similar, multiple times, to burst cells. The lysate is then extracted with heptane or hexane, for example as described in Example 15, and analysed by GC-MS as described in Example 17. Both the untransformed CC503, and the transformed CC503 are assayed for hydrocarbon content by identical methods, and the GC-MS data are compared to detect any hydrocarbons that are present in the transformed cells but not present in the untransformed cells. Any such novel hydrocarbon peaks that are indicated by mass spectrometry to be triterpenoids are concluded to have been derived from the action of the transgene. Five separate transformants are assayed for triterpenoid content, to allow for differences in the chromosomal location of integration events. Integration in euchromatin is expected to facilitate greater expression of the ATB1 gene than integration in heterochromatin, however it is not necessary to know which type of chromatin the gene integrated in, rather it is simply necessary to screen multiple isolates. The isolate which produces the greatest level of triterpenoid (such as squalene, dehydrosqualene, botryococcene, dehydrobotryococcene, or other triterpenoid) compared with non-transgenic control is chosen over the other isolates that were assayed.

Example 22

Structure-Function Analysis

Functional units (motifs) in triterpenoid synthetic polypeptides have been identified. Prosite accession number PDO000802 discloses two squalene and phytoene synthase signatures (PS01044 signature 1 and PS01045 signature 2). PS01044 signature 1 provides the consensus pattern:
  Y-[CSAM]-x(2)-[VSG]-A-[GSA]-[LIVAT]-[IV]-G-x(2)-[LMSC]-x(2)-[LIV].

PS01045 signature 2 provides the consensus pattern:
  [LIVM]-G-x(3)-Q-x(2,3)-[ND]-[IFL]-x-[RE]-D-[LIVMFY]-x(2)-[DE]-x(4,7)-R-x-[FY]-x-P.

These consensus signatures are used to find homologous signatures in the triterpenoid hydrocarbon synthetic polypeptide, thereby identifying one or more amino acids, and the corresponding codon(s), to be mutated. Alternatively, the consensus sequence of FIG. 53 is used to identify one or more amino acids, and the corresponding codon(s), to be mutated.

Oligonucleotide primers for site directed mutagenesis are designed to mutate the one or more codons selected for mutation in a plasmid encoding ATB1. The mutated triterpenoid hydrocarbon synthetic polypeptide is then expressed and its function assayed according to Examples 15 to 17 or Examples 20 and 21 for its triterpenoid hydrocarbon synthetic activity. The function of the mutated polypeptide is then correlated with the structure of the mutated polypeptide to ascertain amino acid residues that contribute to triterpenoid hydrocarbon synthetic activity.

The invention claimed is:

1. An isolated nucleic acid molecule encoding a polypeptide capable of producing a triterpenoid hydrocarbon, the polypeptide comprising SEQ ID NO: 29.

2. The nucleic acid molecule of claim 1, comprising SEQ ID NOs: 30.

3. A recombinant non-human organism capable of producing a triterpenoid hydrocarbon, the organism comprising an isolated nucleic acid molecule encoding a polypeptide capable of producing a triterpenoid hydrocarbon, the polypeptide comprising SEQ ID NO: 29.

4. The recombinant organism of claim 3, wherein the organism is a microorganism.

5. The recombinant organism of claim 3, wherein the organism is an alga or a bacterium.

6. The recombinant organism of claim 3, wherein the organism is selected from the group consisting of: *Escherichia coli*; *Chlamydomonas reinhardtii*; *Saccharomyces cerevisiae*; and *Pichia* sp.

7. A method for producing a triterpenoid hydrocarbon, comprising expressing an isolated nucleic acid molecule encoding a polypeptide capable of producing a triterpenoid hydrocarbon, the polypeptide comprising SEQ ID NO: 29.

8. The method of claim 7, wherein the triterpenoid hydrocarbon is squalene.

9. The method of claim 7, wherein the triterpenoid hydrocarbon is dehydrosqualene.

10. The nucleic acid molecule of claim 1, wherein the triterpenoid hydrocarbon is produced from FPP or PSPP.

11. The nucleic acid molecule or claim 1, wherein the triterpenoid hydrocarbon is squalene.

12. The recombinant organism of claim 3, wherein the nucleic acid molecule comprises SEQ ID NO: 30.

13. The recombinant organism of claim 3, wherein the triterpenoid hydrocarbon is produced from FPP or PSPP.

14. The recombinant organism of claim 3, wherein the triterpenoid hydrocarbon is squalene.

15. The recombinant organism of claim 3, wherein the triterpenoid hydrocarbon is dehydrosqualene.

16. The method of claim 7, wherein the nucleic acid molecule comprises SEQ ID NO: 30.

17. The method of claim 7, wherein the triterpenoid hydrocarbon is produced from FPP or PSPP.

18. The nucleic acid molecule of claim 1, wherein the triterpenoid hydrocarbon is dehydrosqualene.

* * * * *

UNITED STATES PATENT AND TRADEMARK OFFICE
CERTIFICATE OF CORRECTION

PATENT NO. : 8,034,603 B2
APPLICATION NO. : 12/882927
DATED : October 11, 2011
INVENTOR(S) : Ball et al.

Page 1 of 1

It is certified that error appears in the above-identified patent and that said Letters Patent is hereby corrected as shown below:

Column 99, Claim 2, Line 36, replace "NOs: 30" with --NO: 30--.

Column 100, Claim 11, Line 37, replace "molecule or claim" with --molecule of claim--.

Signed and Sealed this
Thirty-first Day of July, 2012

David J. Kappos
*Director of the United States Patent and Trademark Office*